(12) United States Patent
Greaves et al.

(10) Patent No.: US 7,727,287 B2
(45) Date of Patent: Jun. 1, 2010

(54) HEMICYANIN STYRYL THIOL/DISULFIDE DYE, COMPOSITION COMPRISING HEMICYANIN STYRYL THOIL/DISULFIDE DYE, AND METHOD FOR LIGHTENING KERATIN MATERIALS USING HEMICYANIN STYRYL THIOL/DISULFIDE DYE

(75) Inventors: Andrew Greaves, Montevrain (FR); Nicolas Daubresse, La Celles St. Cloud (FR)

(73) Assignee: L'Oreal S.A., Paris (FR)

( * ) Notice: Subject to any disclaimer, the term of this patent is extended or adjusted under 35 U.S.C. 154(b) by 52 days.

(21) Appl. No.: 12/233,955

(22) Filed: Sep. 19, 2008

(65) Prior Publication Data

US 2009/0211038 A1 Aug. 27, 2009

Related U.S. Application Data

(60) Provisional application No. 60/960,611, filed on Oct. 5, 2007.

(30) Foreign Application Priority Data

Sep. 21, 2007 (FR) .................. 07 57778

(51) Int. Cl.
A61Q 5/10 (2006.01)
C07C 321/00 (2006.01)

(52) U.S. Cl. .............. 8/405; 8/431; 8/465; 8/570; 8/587; 8/648; 562/426

(58) Field of Classification Search ............. 8/405, 8/431, 465, 570, 587, 648; 562/426
See application file for complete search history.

(56) References Cited

U.S. PATENT DOCUMENTS

| | | |
|---|---|---|
| 2,904,385 A | 9/1959 | Roger et al. |
| 4,823,985 A | 4/1989 | Grollier et al. |
| 5,944,360 A | 8/1999 | Crapart et al. |
| 7,147,673 B2 | 12/2006 | Plos et al. |
| 7,150,764 B2 | 12/2006 | Plos et al. |
| 7,186,278 B2 | 3/2007 | Plos et al. |
| 7,192,454 B2 | 3/2007 | Plos et al. |
| 7,195,650 B2 | 3/2007 | Plos et al. |
| 7,195,651 B2 | 3/2007 | Plos et al. |
| 7,198,650 B2 | 4/2007 | Pourille-Grethen et al. |
| 7,204,860 B2 | 4/2007 | Plos et al. |
| 7,208,018 B2 | 4/2007 | Gourlaouen et al. |
| 7,217,296 B2 | 5/2007 | Pastore et al. |
| 7,250,064 B2 | 7/2007 | Plos et al. |
| 7,261,744 B2 | 8/2007 | Gourlaouen et al. |
| 7,276,086 B2 | 10/2007 | Gourlaouen |
| 7,303,589 B2 | 12/2007 | Greaves et al. |
| 7,377,946 B2 | 5/2008 | Gourlaouen et al. |
| 7,488,354 B2 | 2/2009 | Daubress et al. |
| 7,531,008 B2 | 5/2009 | Lagrange |
| 7,544,215 B2 | 6/2009 | Speckbacher et al. |
| 2003/0176316 A1 | 9/2003 | Whitehead et al. |
| 2004/0253757 A1 | 12/2004 | Gourlaouen et al. |
| 2005/0031563 A1 | 2/2005 | Gourlaouen et al. |
| 2007/0231940 A1 | 10/2007 | Gourlaouen et al. |
| 2009/0049621 A1 | 2/2009 | Greaves et al. |
| 2009/0089939 A1 | 4/2009 | Greaves et al. |
| 2009/0126125 A1 | 5/2009 | Greaves et al. |
| 2009/0126755 A1 | 5/2009 | Guerin et al. |

FOREIGN PATENT DOCUMENTS

| | | |
|---|---|---|
| BE | 669 934 | 1/1966 |
| EP | 0 860 636 | 8/1998 |
| EP | 1 464 321 | 10/2004 |
| EP | 1 464 323 | 10/2004 |
| EP | 1 464 324 | 10/2004 |
| EP | 1 647 580 | 4/2006 |
| EP | 1 792 605 | 6/2007 |
| EP | 2 001 960 | 12/2008 |
| EP | 2 004 757 | 12/2008 |
| EP | 2 018 847 | 1/2009 |
| EP | 2 062 945 | 5/2009 |
| FR | 1 156 407 | 5/1958 |
| FR | 2 586 913 | 3/1987 |
| FR | 2 830 189 | 4/2003 |
| FR | 2 830 194 | 4/2003 |
| FR | 2 850 271 | 7/2004 |
| FR | 2 921 381 | 3/2009 |
| FR | 2 921 377 | 6/2009 |

Curves of reflectance of TH4 locks treated with dye 1

| | | |
|---|---|---|
| GB | 2 143 541 | 2/1985 |
| GB | 2 180 215 | 3/1987 |
| WO | WO 96/41173 | 12/1996 |
| WO | WO 99/51194 | 10/1999 |
| WO | WO 03/028685 | 4/2003 |
| WO | WO 2004/091473 | 10/2004 |
| WO | WO 2004/091556 | 10/2004 |
| WO | WO 2005/004822 | 1/2005 |
| WO | WO 2005/075574 | 8/2005 |
| WO | WO 2005/097051 | 10/2005 |
| WO | WO 2006/060533 | 6/2006 |
| WO | WO 2006/134043 | 12/2006 |
| WO | WO 2006/134043 A2 * | 12/2006 |
| WO | WO 2006/136617 | 12/2006 |
| WO | WO 2007/025889 | 3/2007 |
| WO | WO 2007/039527 | 4/2007 |
| WO | WO 2007/110537 | 10/2007 |
| WO | WO 2007/110539 | 10/2007 |
| WO | WO 2007/110542 | 10/2007 |
| WO | WO 2009/037324 | 3/2009 |
| WO | WO 2009/037348 | 3/2009 |
| WO | WO 2009/037350 | 3/2009 |
| WO | WO 2009/037385 | 3/2009 |
| WO | WO 2009/040354 | 4/2009 |
| WO | WO 2009/040355 | 4/2009 |

OTHER PUBLICATIONS

STIC Search Report dated Dec. 9, 2009.*
French Search Report for FR 07/57778, dated Aug. 20, 2008.
Ashwell, G. et al., "Improved Molecular Rectification from Self-Assembled Monolayers of a Sterically Hindered Dye," Journal of the American Chemical Society, vol. 127, No. 46, (2005), pp. 16238-16244.
Ashwell, G. et al., "Induced Rectification from Self-Assembled Monolayers of Sterically Hindered-Bridged Chromophores," Journal of Materials Chemistry, vol. 15, No. 11, (2005), pp. 1160-1166.
Ashwell, G. et al., "Molecular Rectification: Self-Assembled Monolayers of a Donor Acceptor Chromophore Connected via a Truncated Bridge," Journal of Materials Chemistry, vol. 13, No. 12, (2003), pp. 2855-2857.
Copending U.S. Appl. No. 12/234,001, filed Sep. 19, 2008.
Copending U.S. Appl. No. 12/234,072, filed Sep. 19, 2008.
Copending U.S. Appl. No. 12/234,135, filed Sep. 19, 2008.
Copending U.S. Appl. No. 12/282,586, filed Sep. 11, 2008.
Copending U.S. Appl. No. 12/293,684, filed Sep. 19, 2008.
Copending U.S. Appl. No. 12/293,723, filed Sep. 19, 2008.
Copending U.S. Appl. No. 12/293,955, filed Sep. 22, 2008.
English language Abstract of EP 1 464 323, dated Oct. 6, 2004.
English language Abstract of EP 2 001 960, dated Dec. 17, 2008.
English language Abstract of EP 2 004 757, dated Dec. 24, 2008.
English language Abstract of EP 2 018 847, dated Jan. 28, 2009.
English language Abstract of EP 2 062 945, dated May 27, 2009.
English language Abstract of FR 2 921 377, dated Jun. 17, 2009.
English language Abstract of FR 2 921 381, dated Mar. 27, 2009.
English language Abstract of WO 2007/110537, dated Oct. 4, 2007.
English language Abstract of WO 2007/110539, dated Oct. 4, 2007.
English language Abstract of WO 2007/110542, dated Oct. 4, 2007.
European Search Report for EP 08 16 4735, dated May 19, 2009.
French Search Report for FR 07/57753, dated Aug. 4, 2008.
French Search Report for FR 07/57755, dated Jul. 30, 2008.
French Search Report for FR 07/57773, dated Jul. 7, 2008.
International Search Report for PCT/FR2007/050997, dated Jun. 19, 2008.
International Search Report for PCT/FR2007/051003, dated Feb. 19, 2008.
International Search Report for PCT/FR2007/051005, dated May 6, 2008.
International Search Report for PCT/FR2007/051008, dated Feb. 5, 2008.
IP.com document dated Oct. 13, 2005.

Kajikawa, K. et al., "Preparation and Optical Characterization of Hemicyanine Self-Assembled Monolayer on Au Substrate," Molecular Crystals and Liquid Crystals Science and Technology, vol. 370, (2001), pp. 277-283.
Naraokaa, R. et al., "Nonlinear Optical Property of Hemicyanine Self-Assembled Monolayers on Gold and its Absorption Kinetics Probed by Optical Second-Harmonic Generation and Surface Plasmon Resonance Spectroscopy," Chemical Physics Letters, vol. 362, No. 1-2, (2002), pp. 26-30.
Notice of Allowance mailed May 4, 2009, in co-pending U.S. Appl. No. 12/234,135.
Notice of Allowance mailed Sep. 3, 2009, in co-pending U.S. Appl. No. 12/234,135.
Office Action mailed Apr. 28, 2009, in co-pending U.S. Appl. No. 12/234,072.
Okawa, H. et al., "Synthesis and Characterization of an Alkanethiol Thin Film Containing a Hemicyanine Dye," Molecular Crystals and Liquid Crystals, vol. 377, (2002), pp. 137-140.
STIC Search Report for U.S. Appl. No. 12/234,072, dated Apr. 23, 2009.
STIC Search Report dated Apr. 27, 2009, for U.S. Appl. No. 12/234,135.
Tsuboi, K. et al., "Formation of Merocyanine Self-Assembled Monolayer and its Nonlinear Optical Properties Probed by Second-Harmonic Generation and Surface Plasmon Resonance," Japanese Journal of Applied Physics, vol. 42, No. 2A, (2003), pp. 607-613.
Wang, Y. et al., "Synthesis and Fluorescence Properties of Triad Compounds with Aromatic Sulfur Bridges," Dyes and Pigments, vol. 51, No. 2-3, (2001), pp. 127-136.
Wang, Y. et al., "Synthesis and Luminescence Properties of Triad Compounds with a Disulfide Bridge," vol. 54, No. 3, (2002), pp. 265-274.

* cited by examiner

*Primary Examiner*—Eisa B Elhilo
(74) *Attorney, Agent, or Firm*—Finnegan, Henderson, Farabow, Garrett & Dunner

(57) ABSTRACT

The present disclosure relates to a novel dye composition for the dyeing and/or lightening of keratin materials, such dye comprising a hemicyanin styryl chromophore thiol or disulfide dye of formula (I) or (II):

the organic or mineral acid salts thereof, optical isomers and geometric isomers thereof, and the solvates thereof such as hydrates. The present disclosure further relates to a dyeing process with a lightening effect on keratin materials, in particular keratin fibers, including human keratin fibers such as the hair, using said composition.

This composition makes it possible to obtain a coloring with a lightening effect which is particularly resistant and visible on dark keratin fibers.

15 Claims, 1 Drawing Sheet

HEMICYANIN STYRYL THIOL/DISULFIDE DYE, COMPOSITION COMPRISING HEMICYANIN STYRYL THOIL/DISULFIDE DYE, AND METHOD FOR LIGHTENING KERATIN MATERIALS USING HEMICYANIN STYRYL THIOL/DISULFIDE DYE

This application claims benefit of U.S. Provisional Application No. 60/960,611, filed Oct. 5, 2007, the contents of which are incorporated herein by reference. This application also claims benefit of priority under 35 U.S.C. §119 to French Patent Application No. FR 0757778, filed Sep. 21, 2007, the contents of which are also incorporated herein by reference.

Disclosed herein is the dyeing of keratin materials using hemicyanin styryl thiol and disulfide fluorescent dyes.

It is known practice to dye keratin fibers, such as human keratin fibers, by direct dyeing. The process conventionally used in direct dyeing comprises applying to the keratin fibers direct dyes which are colored or coloring molecules having an affinity for the fibers, allowing them to diffuse and then rinsing the fibers.

The direct dyes which are conventionally used are, for example, dyes of the nitrobenzene type, anthraquinone dyes, nitropyridine dyes, or dyes of the azo, xanthene, acridine, azine, or triarylmethane type.

It is also known practice to use hemicyanin styryl direct dyes to powerfully dye keratin fibers. These benzothiazolium or benzoimidazolium heteroaryl-group dyes are disclosed, for example, in European Patent Application Nos. EP 1 166 753 and 1 166 757.

The coloring of keratin fibers using these conventional direct dyes does not make it possible to significantly lighten keratin fibers.

Lightening the color of dark keratin fibers to lighter shades, by optionally modifying the shade thereof, constitutes an important need.

Conventionally, in order to obtain a lighter coloring, a chemical bleaching process is used. This process comprises treating the keratin fibers, such as the hair, with a strong oxidizing system, composed for example of hydrogen peroxide, possibly in combination with persalts, which may be in an alkaline medium.

This bleaching system has the drawback of damaging the keratin fibers and of detrimentally affecting their cosmetic properties. The fibers in fact have a tendency to become rough, more difficult to disentangle, and more brittle. Finally, the lightening or the bleaching of keratin fibers with oxidizing agents is incompatible with the treatments for modifying the shape of said fibers, for example in hair straightening treatments.

Another lightening technique comprises applying fluorescent direct dyes to dark hair. This technique, disclosed for example in International Patent Application Nos. WO 03/028685 and WO 2004/091473, makes it possible to retain the quality of the keratin fiber during the treatment. However, these fluorescent direct dyes do not exhibit satisfactory fastness with respect to outside agents.

In order to increase the fastness of direct colorings, it is known practice to use disulfide dyes, for instance azaimidazolium chromophore dyes disclosed in International Patent Application No. WO 2005/097051 or European Patent Application No. 1 647 580, and pyridinium/indolinium styryl chromophore dyes disclosed in International Patent Application Nos. WO 2006/134043 and WO 2006/136617. International Patent Application No. WO 2007/039527 discloses particular styrylthiol dyes for dyeing hair bearing an indole moiety substituted on the 1,2-position of the indole group. None of these patent applications disclose the lightening of keratin fibers without the use of chemical oxidation agents.

One aspect of the present disclosure is to provide new systems for dyeing keratin materials, for example human keratin fibers, including dark hair, which do not have the drawbacks of the existing bleaching processes.

Another aspect of the present disclosure is to provide direct dyeing systems for obtaining lightening effects, including on naturally or artificially dark keratin fibers, which are resistant to successive shampooing operations, which do not damage the keratin fibers and which do not detrimentally affect their cosmetic properties.

Another aspect of the present disclosure is to dye keratin materials chromatically and in a manner which is persistent with respect to outside attacks.

Another aspect of the present disclosure is to be able to extend the dye range available for use on keratin fibers, for exampler on light hair and on dark hair, and to be able to strip the colorings obtained by means of treatments, while not damaging said fibers.

This aspect is achieved with the present disclosure, a subject of which is a process for dyeing keratin materials, such as keratin fibers, for example human keratin fibers such as the hair, including dark hair, comprising applying, to the keratin materials, a dye composition comprising, in a suitable cosmetic medium, at least one hemicyanin styryl disulfide or thiol fluorescent dye, chosen from the dyes of formulae (I) and (II) below:

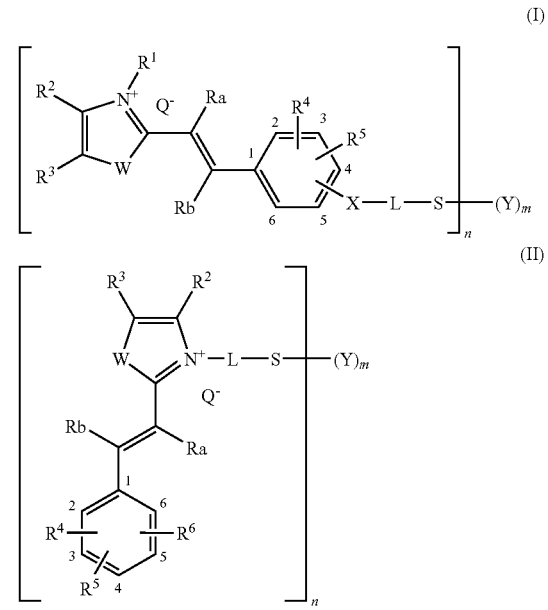

the organic or mineral acid salts, optical isomers and geometric isomers thereof, and the solvates such as hydrates:

wherein:
  n is an integer ranging from 1 to 2;
  m is an integer ranging from 0 to 1;
  Ra and Rb, which may be identical or different, are chosen from a hydrogen atom and a $C_1$-$C_4$ alkyl group; for example, Rb may be a hydrogen atom and, further for example, Ra and Rb may be a hydrogen atom;

$R^1$ is chosen from a hydrogen atom and a ($C_1$-$C_6$)alkyl group, optionally substituted with a group chosen from halogen, $C_1$-$C_4$ alkoxy, $C_1$-$C_4$ (di)(alkyl)amino, phenyl, tolyl and methoxyphenyl;

or else $R^1$ and Ra together form a ($C_3$-$C_6$)alkylene chain, such as ethylene or propylene, or a ($C_3$-$C_7$)alkenylene chain such as —CH=CH—;

$R^2$ and $R^3$, which may be identical or different, are chosen from a hydrogen atom, a halogen atom, an optionally substituted ($C_1$-$C_6$)alkyl group, a ($C_1$-$C_6$)alkoxy group and a ($C_1$-$C_6$)alkylthio group; or else $R^2$ and $R^3$ form, together with the carbon atoms which bear them, an optionally substituted benzo ring;

$R^4$, $R^5$ and $R^6$, which may be identical or different, are chosen from:
  a hydrogen atom;
  a $C_1$-$C_6$, for example $C_1$-$C_2$, alkyl radical optionally substituted with at least one radical chosen from the radicals hydroxyl, $C_1$-$C_2$ alkoxy, $C_2$-$C_4$ (poly)hydroxyalkoxy, acylamino and amino substituted with two $C_1$-$C_4$ alkyl radicals, which may be identical or different;
  a halogen atom such as chlorine, fluorine or bromine;
  a hydroxyl group;
  a $C_1$-$C_2$ alkoxy radical;
  a $C_1$-$C_2$ alkylthio radical;
  an amino radical;
  a 5- or 6-membered heterocycloalkyl radical which may be substituted with 1 to 3 groups, which may be identical or different, chosen from hydroxyl, amino, (di)alkylamino and $C_1$-$C_4$ hydroxyalkyl, such as morpholino, (hydroxyethyl)piperazino, (di)(hydroxy)pyrrolidino, (di)(hydroxy)piperidino;
  an amino radical substituted with one or two $C_1$-$C_6$ alkyl radicals, which may be identical or different, optionally bearing at least:
    i) a hydroxyl group,
    ii) an amino group optionally substituted with one or two $C_1$-$C_3$ alkyl radicals, it being possible for said alkyl radicals to form, with the nitrogen atom to which they are attached, a saturated or unsaturated, optionally substituted heterocycle comprising from 5 to 7 members, optionally comprising at least one other heteroatom which may or may not be different from nitrogen,
  —N(R)—C(O)—R' wherein the R radical is chosen from a hydrogen atom and a $C_1$-$C_4$ alkyl radical optionally bearing at least one hydroxyl group, and the R' radical is a $C_1$-$C_2$ alkyl radical;
  a carboxylic radical in acid or salified form (for example with an alkali metal or an ammonium, substituted or unsubstituted);
  a polyhaloalkyl group comprising from 1 to 6 carbons and from 1 to 6 halogen atoms, which may be identical or different, the polyhaloalkyl group being, for example, trifluoromethyl;
  $R_4$ and $R_5$ may, for example, be hydrogen atoms and $R^6$ may, for example, be positioned on carbon atom 4 of the phenyl ring, $R^6$ may, for example, be a substituted amino group;

or else two contiguous radicals $R^4$ with $R^5$ and/or $R^5$ with $R^6$ form, together with the carbon atoms which bear them, a benzo ring or a heterocycle, optionally substituted, fused to the phenyl group, for example a heterocycle chosen from morpholinyl, piperazinyl, piperidinyl and indolyl, the latter being fused to the phenyl group of formula (I) or (II) for example at b-[3,4], or $R^4$ and $R^5$ form, for example together with the phenyl group of formula (I) or (II) which bears them, a carbazol group;

or else $R^4$, $R^5$ and $R^6$ form, together with the phenyl group of formula (II), a tricyclic unit of julolidine type:

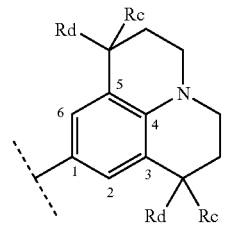

wherein Rc and Rd are chosen from a hydrogen atom and a $C_1$-$C_4$ alkyl group;

L is a $C_1$-$C_{20}$ divalent hydrocarbon-based chain, which is optionally substituted, optionally interrupted and/or optionally terminated at one or the other of its ends i) with at least one divalent group or combinations thereof chosen from: —N(R)—; —N$^+$(R)(R°)—, An$^-$, —O—, —S—, —CO—, and —SO$_2$— with R and R°, which may be identical or different, chosen from a hydrogen, and a $C_1$-$C_4$ alkyl, hydroxyalkyl, or aminoalkyl radical, and An$^-$ is an anionic counterion, or ii) with a cationic heterocycle or cationic heteroaryl Het$^+$, An$^-$, wherein An$^-$ is defined as above and Het$^+$ is chosen from a saturated or unsaturated heterocycle comprising from 5 to 10 members, and a heteroaryl comprising from 5 to 10 members, such as imidazolium, pyridinium, piperazinium, piperidinium, pyrrolidinium or benzoimidazolium; for instance, L may be a ($C_1$-$C_6$)alkylene chain such as methylene, ethylene, propylene or butylene;

X is an oxygen or sulfur atom or an NR group wherein R is chosen from a hydrogen atom and a ($C_1$-$C_6$)alkyl group;

Y is chosen from: i) a hydrogen atom; ii) an alkali metal; iii) an alkaline earth metal; iv) an ammonium group: N$^+$R$^\alpha$R$^\beta$R$^\gamma$R$^\delta$, An''$^-$ or a phosphonium group P$^+$R$^\alpha$R$^\beta$R$^\gamma$R$^\delta$, An''$^-$ with R$^\alpha$, R$^\beta$, R$^\gamma$ and R$^\delta$, which may be identical or different, chosen from a hydrogen atom and a ($C_1$-$C_4$)alkyl group and An''$^-$ an anionic counterion; and v) a thiol-function-protecting group;

W is chosen from an oxygen atom, a sulfur atom, and an NR' group wherein R' is chosen from a hydrogen atom and a ($C_1$-$C_4$)alkyl group;

Q$^-$ is an anionic counterion;

it being understood that, when n is 2, then m is zero, and when n is 1, then m is 1.

Another subject of the present disclosure is a dye composition for dyeing keratin fibers with a lightening effect, comprising, in a suitable cosmetic medium, at least one hemicyanin styryl disulfide or thiol fluorescent dye of formula (I) or (II) as defined above, and optionally a reducing agent.

A subject of the present disclosure is also novel hemicyanin styryl disulfide or thiol fluorescent dyes of formula (I) or (II) as defined above.

Another subject of the present disclosure is a multicompartment device wherein a first compartment contains a dye composition comprising at least one fluorescent dye of formula (I) or (II) as defined above and a second compartment contains a reducing agent, and optionally a third compartment contains an oxidizing agent.

The dyeing process according to the present disclosure makes it possible to visibly color dark keratin materials, for example dark human keratin fibers, including dark hair. Furthermore, the process of the present disclosure makes it possible to obtain a coloring of the hair, without damaging it, which is persistent with respect to shampooing operations, common attacks (for example sunlight or perspiration) and hair treatments. The process of the present disclosure also makes it possible to obtain lightening of keratin materials such as keratin fibers, including dark keratin fibers, and further including dark hair.

Moreover, the new dyes according to the present disclosure have very satisfactory photostability and chemical stability. These dyes may be soluble in the cosmetic media suitable for hair dyes, for example in water/ethanol mixtures. These dyes make it possible to extend the accessible color range (yellow, orange, red, violet, and blue dyes) while allowing stripping of the colorings obtained without damaging the fiber. This process also makes it possible to dye bleached keratin fibers in a powerful and chromatic manner.

The dye range obtained using the dyes of the present disclosure also covers the basic shades most in demand in hair dyeing.

Figure 1:
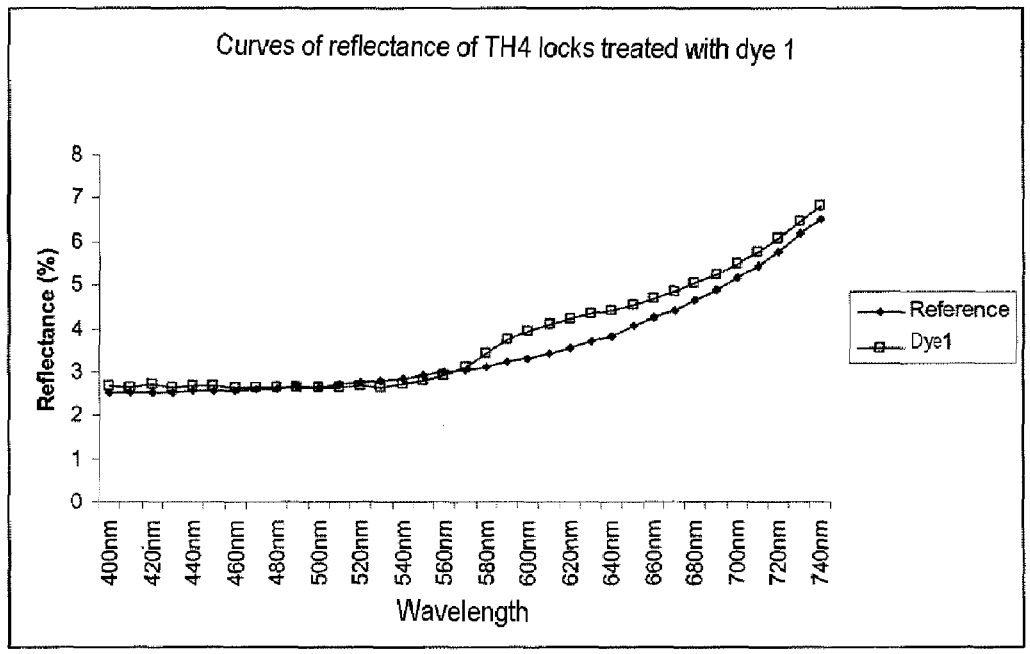
FIG. 1 shows the reflectance values of a reference lock (a lock of untreated hair of tone height TH4) and the reflectance values of a TH4 lock treated with dye [1].

As used herein, "dark keratin material" means that which exhibits a lightness $L^*$ measured in the C.I.E. $L^*a^*b^*$ system of less than or equal to 45, for example less than or equal to 40, given that, $L^*=0$ is equivalent to black and $L^*=100$ is equivalent to white.

As used herein, "naturally or artificially dark hair" means hair whose tone height is less than or equal to 6 (dark blond) and for example less than or equal to 4 (chestnut-brown).

The lightening of the hair is evaluated by the variation in "tone height" before and after application of the compound of formula (I) or (II). It is understood that "tone" is based on the classification of the natural shades, one tone separating each shade from the shade immediately following or preceding it. This definition and the classification of the natural shades are well known to hair styling professionals and are published in the book "Science des traitements capillaires" [Hair Treatment Sciences], Charles Zviak 1988, Masson, pp. 215 and 278.

The tone heights range from 1 (black) to 10 (very light blond), one unit corresponding to one tone; the higher the figure, the lighter the shade.

An artificially colored hair is a hair whose color has been modified by a dyeing treatment, for example dyeing with direct dyes or oxidation dyes.

As used herein, "bleached hair" means hair whose tone height is greater than 6 and for example greater than 8.

As used herein, "stripping" the coloring of keratin fibers means a process which involves the application of a chemical or physical stimulus capable of returning the hair to its original color. By way of non-limiting example, the stripping can be obtained by application of an oxidizing composition based on hydrogen peroxide, on sodium persulfate, on potassium persulfate, or on ammonium persulfate, at a moderately alkaline pH, i.e. between 7 and 12, for example between 8 and 10.5.

One means for measuring the lightening effect given to the hair after application of the fluorescent dyes of the present disclosure is to use the phenomenon of hair reflectance.

In at least one embodiment, the composition should, after application to dark hair, lead to at least one of the results below:

Interest is focused on the hair reflectance performance levels when said hair is irradiated with visible light in the wavelength range from 400 to 700 nanometers.

The curves of reflectance as a function of wavelength, of the hair treated with the composition of the present disclosure and of untreated hair, are then compared.

The curve corresponding to the treated hair should show a reflectance in the wavelength range from 500 to 700 nanometers which is higher than the curve corresponding to the untreated hair.

This means that, in the wavelength range from 540 to 700 nanometers, there is at least one range where the reflectance curve corresponding to the treated hair is higher than the reflectance curve corresponding to the untreated hair. As used herein, "higher" is intended to mean a difference of at least 0.05% in reflectance, and in at least one embodiment of at least 0.1%. All the same, there may be, in the wavelength range from 540 to 700 nanometers, at least one range where the reflectance curve corresponding to the treated hair is superimposable on or lower than the reflectance curve corresponding to the untreated hair.

In at least one embodiment, the wavelength where the difference is at a maximum between the reflectance curve of the treated hair and that of the untreated hair is within the wavelength range from 500 to 650 nanometers, and for example within the wavelength range from 550 to 620 nanometers.

For the purpose of the present disclosure, and unless otherwise indicated, the "aryl" or "heteroaryl" radicals or the aryl or heteroaryl part of a radical may be substituted with at least one substituent, chosen from:

a $C_1$-$C_{16}$, for example $C_1$-$C_8$, alkyl radical optionally substituted with at least one radical chosen from the radicals: hydroxyl, $C_1$-$C_2$ alkoxy, $C_2$-$C_4$(poly)hydroxyalkoxy, acylamino and amino substituted with two $C_1$-$C_4$ alkyl radicals, which may be identical or different, optionally bearing at least one hydroxyl group, or the two radicals possibly forming, with the nitrogen atom to which they are attached, a heterocycle comprising from 5 to 7 members, for example 5 or 6 members, which is saturated or unsaturated, which is optionally substituted, and which optionally comprises another heteroatom which may be identical or different from the nitrogen;

a halogen atom such as chlorine, fluorine or bromine;

a hydroxyl group;

a $C_1$-$C_2$ alkoxy radical;

a $C_1$-$C_2$ alkylthio radical;

a $C_2$-$C_4$ (poly)hydroxyalkoxy radical;

an amino radical;

a 5- or 6-membered heterocycloalkyl radical;

an optionally cationic 5- or 6-membered heteroaryl radical, such as imidazolium, optionally substituted with a $C_1$-$C_4$ alkyl radical, such as methyl;

an amino radical substituted with one or two $C_1$-$C_6$ alkyl radicals, which may be identical or different, optionally bearing at least:

i) one hydroxyl group, and/or ii) one amino group optionally substituted with one or two optionally substituted $C_1$-$C_3$ alkyl radicals, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen, —N(R)—C(O)—R' wherein the R radical is chosen from a hydrogen atom and a $C_1$-$C_4$ alkyl radical optionally bearing at least one hydroxyl group, and the R' radical is a $C_1$-$C_2$ alkyl radical;

$(R)_2N$—C(O)— wherein the R radicals, which may or may not be identical, are chosen from a hydrogen atom and a $C_1$-$C_4$ alkyl radical optionally bearing at least one hydroxyl group;

$R'S(O)_2$—N(R)— wherein the R radical is chosen from a hydrogen atom and a $C_1$-$C_4$ alkyl radical optionally bearing at least one hydroxyl group, and the R' radical is chosen from a $C_1$-$C_4$ alkyl radical and a phenyl radical;

$(R)_2N$—$S(O)_2$— wherein the R radicals, which may or may not be identical, are chosen from a hydrogen atom and a $C_1$-$C_4$ alkyl radical optionally bearing at least one hydroxyl group, a carboxylic radical in acid or salified form (for example with an alkali metal or an ammonium, which is substituted or unsubstituted);

a cyano group; and a polyhaloalkyl group containing from 1 to 6 carbon atoms and from 1 to 6 halogen atoms, which may be identical or different; the polyhaloalkyl group may be, for example, trifluoromethyl.

For the purpose of the present disclosure, and unless otherwise indicated, the cyclic or heterocyclic part of a nonaromatic radical may be substituted with at least one substituent, chosen from the groups:

hydroxyl;

$C_1$-$C_4$ alkoxy;

$C_1$-$C_4$ alkyl;

$C_2$-$C_4$ (poly)hydroxyalkoxy;

a $C_1$-$C_2$ alkylthio radical;

RC(O)—N(R')— wherein the R' radical is chosen from a hydrogen atom and a $C_1$-$C_4$ alkyl radical optionally bearing at least one hydroxyl group, and the R radical is chosen from a $C_1$-$C_2$ alkyl radical and an amino radical substituted with two $C_1$-$C_4$ alkyl groups, which may be identical or different, optionally bearing at least one hydroxyl group;

RC(O)—O— wherein the R radical is chosen from a $C_1$-$C_4$ alkyl radical and an amino radical substituted with one or two $C_1$-$C_4$ alkyl groups, which may be identical or different, optionally bearing at least one hydroxyl group, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen; and RO—C(O)— wherein the R radical is a $C_1$-$C_4$ alkyl radical optionally bearing at least one hydroxyl group.

For the purpose of the present disclosure, and unless otherwise indicated, a cyclic or heterocyclic radical or a nonaromatic part of an aryl or heteroaryl radical may also be substituted with at least one oxo or thioxo group.

For the purpose of the present disclosure, and unless otherwise indicated, an "aryl" radical is a condensed or noncondensed, $C_6$-$C_{22}$ monocyclic or polycyclic group, and at least one ring of which is aromatic; for example, the aryl radical may be a phenyl, biphenyl, naphthyl, indenyl, anthracenyl or tetrahydronaphthyl.

For the purpose of the present disclosure, and unless otherwise indicated, a "diarylalkyl" radical is a group comprising, on the same carbon atom of an alkyl group, two aryl groups, which may be identical or different, such as diphenylmethyl or 1,1-diphenylethyl.

For the purpose of the present disclosure, and unless otherwise indicated, a "heteroaryl radical" is an optionally cationic, condensed or noncondensed, monocyclic or polycyclic group comprising from 5 to 22 members and from 1 to 6 heteroatoms chosen from a nitrogen, oxygen, sulfur, and selenium atom, and at least one ring of which is aromatic; for example, a heteroaryl radical may be chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl, and its ammonium salt.

For the purpose of the present disclosure, and unless otherwise indicated, a "diheteroarylalkyl" radical is a group comprising, on the same carbon atom of an alkyl group, two heteroaryl groups, which may be identical or different, such as difurylmethyl, 1,1-difurylethyl, dipyrrolylmethyl or dithienylmethyl.

For the purpose of the present disclosure, and unless otherwise indicated, a "cyclic radical" is a condensed or noncondensed, monocyclic or polycyclic, $C_5$-$C_{22}$ nonaromatic cycloalkyl radical, possibly comprising at least one unsaturation for example, the cyclic radical may be a cyclohexyl.

For the purpose of the present disclosure, and unless otherwise indicated, a "sterically hindered cyclic" radical is a substituted or unsubstituted, aromatic or nonaromatic, cyclic radical hindered by steric effect or constraint, comprising from 6 to 14 members, which may be bridged; by way of sterically hindered radicals, non-limiting mention may be made of bicyclo[1.1.0]butane, mesityls such as 1,3,5-trimethylphenyl, 1,3,5-tri-tert-butylphenyl, 1,3,5-isobutylphenyl, 1,3,5-trimethylsilylphenyl, and adamantyl.

For the purpose of the present disclosure, and unless otherwise indicated, a "heterocyclic radical or heterocycle" is a condensed or noncondensed, monocyclic or polycyclic, nonaromatic radical comprising from 5 to 22 members, comprising from 1 to 6 heteroatoms chosen from nitrogen, oxygen, sulfur, and selenium.

For the purpose of the present disclosure, and unless otherwise indicated, an "alkyl radical" is a linear or branched, $C_1$-$C_{16}$, such as $C_1$-$C_8$, hydrocarbon-based radical.

For the purpose of the present disclosure, and unless otherwise indicated, an "alkylene" radical is a divalent alkyl radical as defined above.

For the purpose of the present disclosure, and unless otherwise indicated, an "alkenylene" radical is a divalent hydrocarbon-based radical comprising from one to three carbon-carbon double bonds, the double bonds may be conjugated, such as —CH=CH—, —CH=CH—CH=CH—, —CH=CH—CH=CH—CH=CH—.

As used herein, "optionally substituted" assigned to the alkyl radical implies that said alkyl radical may be substituted with at least one radical chosen from the radicals: i) hydroxyl; ii) $C_1$-$C_4$ alkoxy; iii) acylamino; iv) amino optionally substituted with one or two $C_1$-$C_4$ alkyl radicals, which may be identical or different, said alkyl radicals possibly forming, with the nitrogen atom which bears them, a heterocycle comprising from 5 to 7 members, optionally comprising another heteroatom which may or may not be different from nitrogen; v) or a quaternary ammonium group —N+R'R"R'", M⁻ for which R', R", R'", which may be identical or different, are chosen from a hydrogen atom and a $C_1$-$C_4$ alkyl group, or else —N⁺R'R"R'" forms a heteroaryl such as imidazolium optionally substituted with a $C_1$-$C_4$ alkyl group, and M⁻ is the counterion of the corresponding organic acid, mineral acid or halide.

For the purpose of the present disclosure, and unless otherwise indicated, an "alkoxy radical" is an alkyloxy or alkyl-O-radical for which the alkyl radical is a linear or branched, $C_1$-$C_{16}$, for example $C_1$-$C_8$, hydrocarbon-based radical.

For the purpose of the present disclosure, and unless otherwise indicated, an "alkylthio radical" is an alkyl-S— radical for which the alkyl radical is a linear or branched, $C_1$-$C_{16}$, for example $C_1$-$C_8$, hydrocarbon-based radical; and when the alkylthio group is optionally substituted, this implies that the alkyl group is optionally substituted as defined above.

For the purpose of the present disclosure, and unless otherwise indicated, the limits delimiting the extent of the range of values are included in this range of values.

For the purpose of the present disclosure, and unless otherwise indicated, an "organic or mineral acid salt" may be chosen from a salt derived: i) from hydrochloric acid HCl; ii) from hydrobromic acid HBr; iii) from sulfuric acid $H_2SO_4$; iv) from alkylsulfonic acids: Alk-S(O)$_2$OH such as methylsulfonic acid and ethylsulfonic acid; v) from arylsulfonic acids: Ar—S(O)$_2$OH such as from benzenesulfonic acid and from toluenesulfonic acid; vi) from citric acid; vii) from succinic acid; viii) from tartaric acid; ix) from lactic acid; x) from alkoxysulfinic acids: Alk-O—S(O)OH such as from methoxysulfinic acid and from ethoxysulfinic acid; xi) from aryloxysulfinic acids such as from tolueneoxysulfinic acid and from phenoxysulfinic acid; xii) from phosphoric acid $H_3PO_4$; xiii) from acetic acid $CH_3C(O)OH$; xiv) from triflic acid $CF_3SO_3H$; and xv) from tetrafluoroboric acid $HBF_4$.

For the purpose of the present disclosure, and unless otherwise indicated, an "anionic counterion" is an anion or an anionic group associated with the cationic charge of the dye; for example, the anionic counterion may be chosen from: i) halides such as chloride or bromide; ii) nitrates; iii) sulfonates, among which are $C_1$-$C_6$ alkyl sulfonates: Alk-S(O)$_2$O⁻ such as methyl sulfonate or mesylate and ethyl sulfonate; iv) aryl sulfonates: Ar—S(O)$_2$O⁻ such as benzene sulfonate and toluenesulfonate or tosylate; v) citrate; vi) succinate; vii) tartrate; viii) lactate; ix) alkyl sulfates: Alk-O—S(O)O⁻ such as methyl sulfate and ethyl sulfate; x) arylsulfates: Ar—O—S(O)O⁻ such as benzenesulfate and toluenesulfate; xi) alkoxysulfates: Alk-O—S(O)$_2$O— such as methoxy sulfate and ethoxy sulfate; xii) aryloxysulfates: Ar—O—S(O)$_2$O⁻; xiii) phosphate; xiv) acetate; xv) triflate; and xvi) borates such as tetrafluoroborate.

For the purpose of the present disclosure, and unless otherwise indicated, the "solvates" are the hydrates and also the association with linear or branched $C_1$-$C_4$ alcohols such as ethanol, isopropanol, or n-propanol.

The hemicyanin styryl disulfide or thiol dyes of formula (I) or (II) as defined above, are fluorescent dyes, i.e. are capable of absorbing in the UV range or visible range at a wavelength $\gamma_{abs}$ ranging from 250 to 800 nm and capable of re-emitting in the visible range at an emission wavelength $\gamma_{em}$ ranging from 400 to 800 nm.

Non-limiting examples of the fluorescent compounds of formula (I) or (II) of the present disclosure are dyes capable of absorbing in the visible range $\gamma_{abs}$ ranging from 400 to 800 nm and of re-emitting in the visible range $\gamma_{em}$ ranging from 400 to 800 nm. In at least one embodiment, the dyes of formula (I) or (II) are dyes capable of absorbing at a $\gamma_{abs}$ ranging from 420 to 550 nm and of re-emitting in the visible range at a $\gamma_{em}$ ranging from 470 to 600 nm.

The compounds of the present disclosure of formula (I) or (II) when n and m are 1 comprise an SY function which may be in the covalent form —S—Y or ionic form —S⁻Y⁺ depending on the nature of Y and on the pH of the medium.

At least one embodiment relates to the hemicyanin styryl disulfide or thiol fluorescent dyes of formula (I) or (II) where n and m are 1, and Y is chosen from a hydrogen atom and an alkali metal. In at least one embodiment, Y is a hydrogen atom.

In accordance with another specific embodiment of the present disclosure, in the abovementioned formula (I) or (II), Y is a protecting group known to those skilled in the art, for instance those described in the books "*Protective Groups in Organic Synthesis*", T. W. Greene, John Wiley & Sons Ed., NY, 1981, pp. 193-217; "*Protecting Groups*", P. Kocienski, Thieme, 3rd Ed., 2005, Chap. 5. It being understood that Y as protective group cannot constitute with the sulphur atom on which it is linked a disulfide dye i.e. cannot constitute a formula (I) or (II) wherein n and m both are 1. Y as protective group cannot be a group directly linked to the sulphur atom of formula (I) and (II) via another non oxidized sulphur atom.

In at least one embodiment, when Y is a thiol-function-protecting group, Y is chosen from the following radicals:
($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$)(alkyl)aminocarbonyl;
(di)($C_1$-$C_4$)(alkyl)aminothiocarbonyl;
arylcarbonyl such as phenylcarbonyl;
aryloxycarbonyl;
aryl($C_1$-$C_4$)alkoxycarbonyl;
(di)($C_1$-$C_4$)(alkyl)aminocarbonyl such as dimethylaminocarbonyl;
($C_1$-$C_4$)(alkyl)arylaminocarbonyl;
carboxyl;
$SO_3^-$, M⁺ wherein M⁺ is an alkali metal such as sodium or potassium, or else Q⁻ or An'⁻ of formula (I) or (II) and M⁺ are absent;
optionally substituted aryl such as phenyl, dibenzosuberyl or 1,3,5-cycloheptatrienyl,
optionally substituted heteroaryl; including the cationic or noncationic heteroaryl comprising from 1 to 4 heteroatoms below:
  i) monocyclic comprising 5, 6 or 7 members, such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;

ii) bicyclic comprising 8 to 11 members, such as indolyl, indolinium, benzoimidazolyl, benzoimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with at least one group such as $(C_1$-$C_4)$ alkyl, for instance methyl, or polyhalo$(C_1$-$C_4)$alkyl, for instance trifluoromethyl;

iii) or tricyclic ABC below:

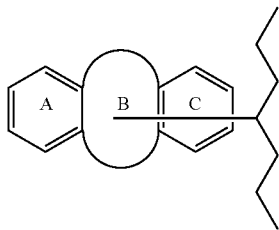

wherein the two rings A, C optionally comprise a heteroatom, and the ring B is a 5-, 6- or 7-membered, for instance 6-membered ring and comprises at least one heteroatom, for instance piperidyl or pyranyl;

optionally cationic, optionally substituted heterocycloalkyl, the heterocycloalkyl group may be for example a saturated or partially saturated, 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidinyl, morpholinyl, di/tetra/hexahydroazepinyl, or di/tetrahydropyrimidinyl, these groups being optionally substituted with at least one group such as $(C_1$-$C_4)$ alkyl, oxo or thioxo; or the heterocycle is the following group:

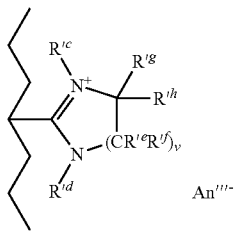

wherein $R'^c$, $R'^d$, $R'^e$, $R'^f$, $R'^g$ and $R'^h$, which may be identical or different, are chosen from a hydrogen atom and a $(C_1$-$C_4)$ alkyl group, or else two groups $R'^g$ with $R'^h$, and/or $R'^e$ with $R'^f$, form an oxo or thioxo group, or else $R'^g$ with $R'^e$ together form a cycloalkyl; and v is an integer ranging from 1 to 3; in at least one embodiment, $R'^c$ to $R'^h$ are a hydrogen atom; and $An''''^-$ is a counterion;

isothiouronium —$C(NR'^cR'^d)$=$N^+R'^eR'^f$; $An''''^-$ wherein $R'^c$, $R'^d$, $R'^e$ and $R'^f$, which may be identical or different, are chosen from a hydrogen atom and a $(C_1$-$C_4)$alkyl group; in at least one embodiment, $R'^c$ to $R'^f$ are a hydrogen atom; and $An''''^-$ is a counterion;

isothiourea —$C(NR'^cR'^d)$=$NR'^e$; wherein $R'^c$, $R'^d$ and $R'^e$ are defined as above;

optionally substituted (di)aryl$(C_1$-$C_4)$alkyl, such as 9-anthracenylmethyl, phenylmethyl or diphenylmethyl optionally substituted with at least one group for example chosen from $(C_1$-$C_4)$ alkyl, $(C_1$-$C_4)$ alkoxy such as methoxy, hydroxyl, alkylcarbonyl, and (di)$(C_1$-$C_4)$(alkyl)amino such as dimethylamino;

optionally substituted (di)heteroaryl$(C_1$-$C_4)$alkyl, the heteroaryl group is for example cationic or noncationic, and monocyclic, comprising 5 or 6 members and from 1 to 4 heteroatoms chosen from nitrogen, oxygen, and sulfur, such as the groups pyrrolyl, furanyl, thiophenyl, pyridyl, pyridyl N-oxide such as 4-pyridyl or 2-pyridyl N-oxide, pyrylium, pyridinium, or triazinyl, optionally substituted with at least one group such as alkyl, including methyl, in at least one embodiment the (di)heteroaryl$(C_1$-$C_4)$alkyl is (di)heteroarylmethyl or (di)heteroarylethyl;

$CR^1$, $R^2R^3$ wherein $R^1$, $R^2$, and $R^3$, which may be identical or different, are chosen from a halogen atom and a group chosen from:

—$(C_1$-$C_4)$alkyl;

—$(C_1$-$C_4)$alkoxy;

optionally substituted aryl, such as phenyl optionally substituted with at least one group such as $(C_1$-$C_4)$ alkyl, $(C_1$-$C_4)$alkoxy, or hydroxyl;

optionally substituted heteroaryl, such as thiophenyl, furanyl, pyrrolyl, pyranyl, or pyridyl, optionally substituted with a $(C_1$-$C_4)$alkyl group;

$P(Z^1)R'^1R'^2R'^3$ wherein $R'^1$ and $R'^2$, which may be identical or different, are chosen from a hydroxyl, $(C_1$-$C_4)$ alkoxy, and alkyl group, $R'^3$ is chosen from a hydroxyl and $(C_1$-$C_4)$alkoxy group and $Z^1$ is chosen from an oxygen atom and a sulfur atom;

a sterically hindered cyclic; and optionally substituted alkoxyalkyl, such as methoxymethyl (MOM), ethoxyethyl (EOM) or isobutoxymethyl.

According to at least one embodiment, the protected thiol fluorescent dyes of formula (I) or (II) for which m and n are 1 comprising a group Y i) which is a cationic, aromatic 5- or 6-membered monocyclic heteroaryl group comprising from 1 to 4 heteroatoms chosen from oxygen, sulfur, and nitrogen, such as oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinyl, pyrazinium, pyridazinium, triazinium, tetrazinium, oxazepinium, thiepinyl, thiepinium, or imidazolium; ii) cationic 8- to 11-membered bicyclic heteroaryl group, such as indolinium, benzoimidazolium, benzoxazolium, or benzothiazolium, these monocyclic or bicyclic heteroaryl groups being optionally substituted with at least one group such as alkyl, for instance methyl, or polyhalo$(C_1$-$C_4)$alkyl, for instance trifluoromethyl; iii) or heterocyclic group below:

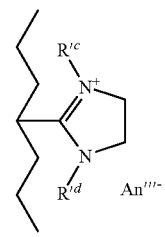

wherein $R'^c$ and $R'^d$, which may be identical or different, are chosen from a hydrogen atom and a $(C_1$-$C_4)$alkyl group; in at least one embodiment, $R'^c$ to $R'^d$ are a $(C_1$-$C_4)$alkyl group such as methyl; and $An''''^-$ is an anionic counterion.

In at least one embodiment, Y is a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium, and imidazolium, benzoimidazolium, benzoxazolium, benzothiazolium, these groups being optionally substituted with at least one (C$_1$-C$_4$)alkyl groups, for example methyl.

In at least one embodiment, Y is an alkali metal or a protecting group chosen from:
- (C$_1$-C$_4$)alkylcarbonyl, such as methylcarbonyl or ethylcarbonyl;
- arylcarbonyl such as phenylcarbonyl;
- (C$_1$-C$_4$)alkoxycarbonyl;
- aryloxycarbonyl;
- aryl(C$_1$-C$_4$)alkoxycarbonyl;
- (di)(C$_1$-C$_4$)(alkyl)aminocarbonyl such as dimethylaminocarbonyl;
- (C$_1$-C$_4$)(alkyl)arylaminocarbonyl;
- optionally substituted aryl, such as phenyl;
- 5- or 6-membered monocyclic heteroaryl, such as imidazolyl or pyridyl;
- 5- or 6-membered cationic monocyclic heteroaryl, such as pyrylium, pyridinium, pyrimidinium, pyrazinium, pyridazinium, triazinium, or imidazolium; these groups being optionally substituted with at least one identical or different (C$_1$-C$_4$)alkyl group, such as methyl;
- 8- to 11-membered cationic bicyclic heteroaryl, such as benzoimidazolium or benzoxazolium; these groups being optionally substituted with at least one identical or different (C$_1$-C$_4$)alkyl group, such as methyl;

cationic heterocycle of the following formula:

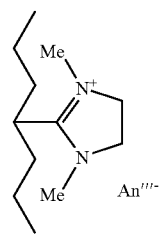

wherein An'''$^-$ is an anionic counterion
isothiouronium —C(NH$_2$)=N$^+$H$_2$; An''''$^-$;
isothiourea —C(NH$_2$)=NH; and
SO$_3^-$, M$^+$ wherein M$^+$ is an alkali metal such as sodium or potassium, or else Q$^-$ or An'$^-$ of formula (I) or (II) and M$^+$ are absent.

According to at least one embodiment of the present disclosure, the fluorescent dyes of formula (I) or (II) are disulfide dyes wherein n is 2 and m is 0.

Non-limiting examples of the disulfide fluorescent dyes of formula (I) of the present disclosure are chosen from those of formulae (I$_a$), (II$_a$), (I$_b$) and (II$_b$):

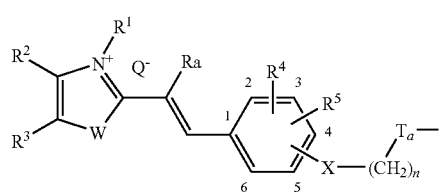 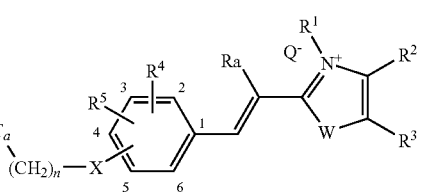

(I$_a$)

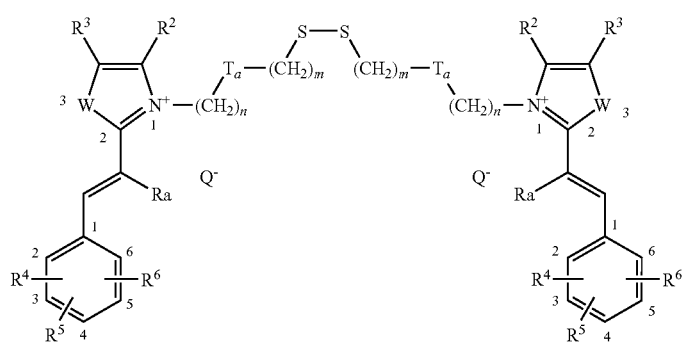

(II$_a$)

-continued

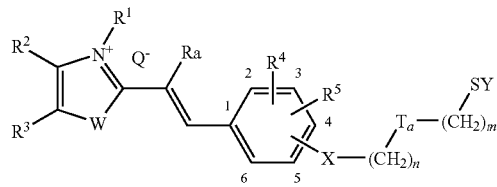
(I_b)

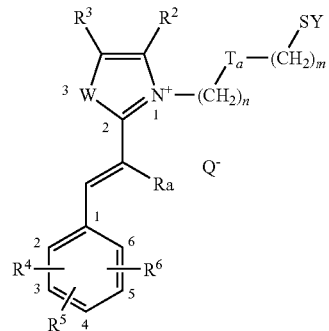
(II_b)

wherein:
  $R_a$, $R^1$ to $R^6$, B, Y and $Q^-$ are defined as above;
  n and m, which may be identical or different, are an integer ranging from 1 to 6, with the sum of n+m ranging from 2 to 4, for example 2 or 3 for (II_a);
  X is a radical chosen from: -G-, -G'-C(G)- and —C(G)-G'-, wherein G and G', which may be identical or different, are chosen from an oxygen atom, a sulfur atom, and NR, wherein R is chosen from a hydrogen atom and a $(C_1$-$C_6)$alkyl group; for example X is a group —NR—, —NR—CO—, —C(O)—NR—, —S(O)$_2$—, —S(O)$_2$—NR—, or —NR—S(O)$_2$—, or —NR—; further for example, X of formula (I_a) is linked at the 4-position on the phenyl group which is unsubstituted or substituted with the groups $R^4$ and $R^5$;
  $T_a$ is chosen from a σ covalent bond, a group —N(R'_a)—; —N$^+$(R'_a)(R'_b)—, An$^-$; —C(O)—N(R'_a)— or —N(R'_a)—C(O)—, and a divalent cationic heteroaryl comprising from 5 to 7 members, such as imidazolium, wherein R'_a, R'_b, which may be identical or different, are chosen from a hydrogen atom and a $(C_1$-$C_4)$alkyl radical, An$^-$ is an anionic counterion; for instance, $T_a$ may be —C(O)—N(R'_a)— and —N(R'_a)—C(O)—.

In at least one embodiment, the dyes of the present disclosure have radicals X which comprise an NR group at position 4 on the phenyl, $R^4$ and $R^5$ are a hydrogen atom or else forming, together, a benzo or morpholinyl group optionally substituted with an alkyl group, $R^2$ and $R^3$ are chosen from a hydrogen and a halogen atom, or else forming, together, a benzo group optionally substituted with from 1 to 3 halogen atoms, L for example may be an ethylene, propylene, or butylene group, and in at least one embodiment an ethylene group.

By way of non-limiting example, mention may be made of the following dyes of formula (I) or (II)

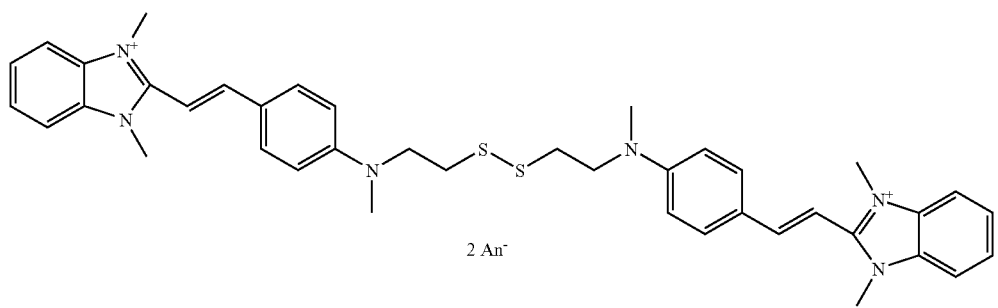

1

2 An$^-$

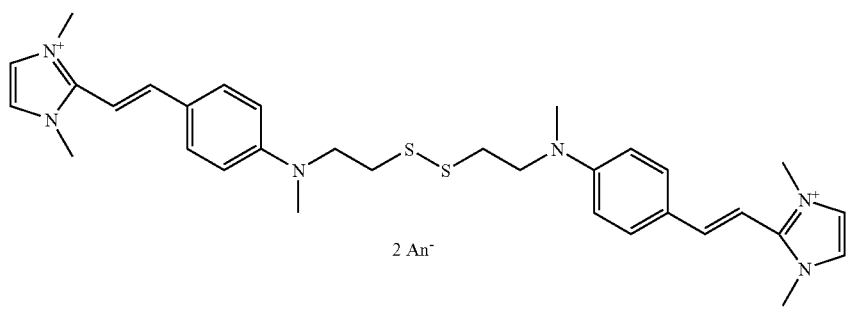

2

2 An$^-$

-continued
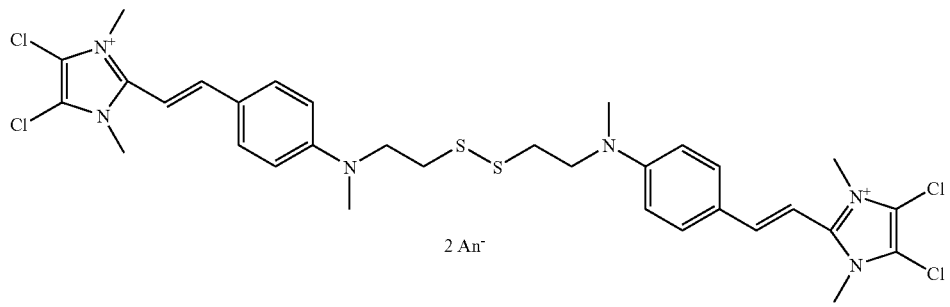
3
2 An⁻
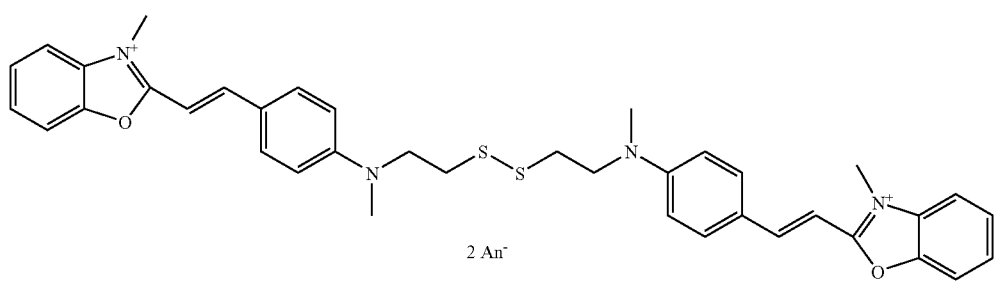
4
2 An⁻
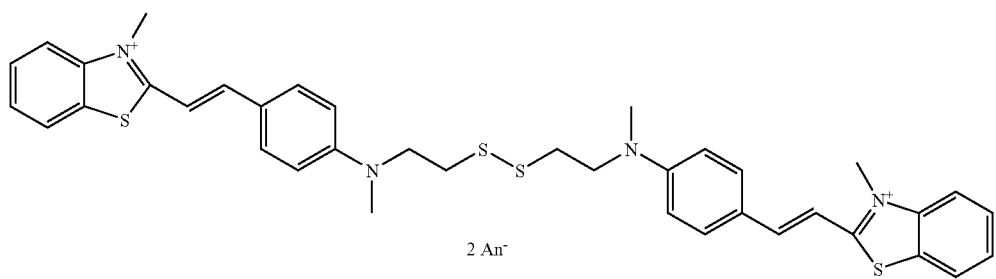
5
2 An⁻
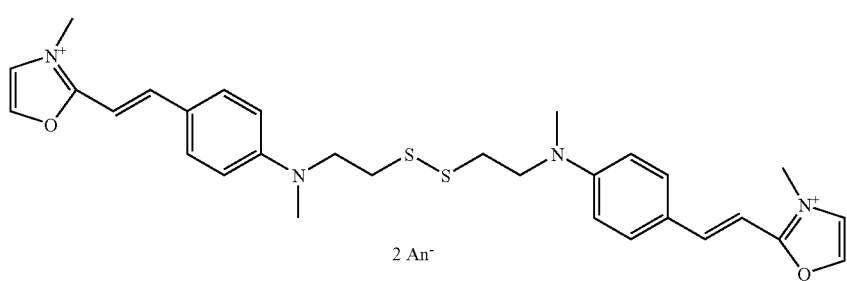
6
2 An⁻

-continued
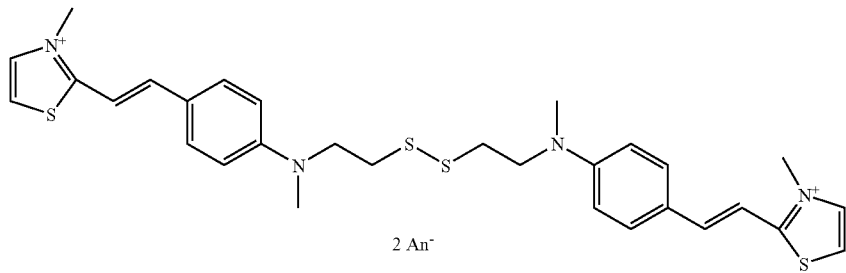
7
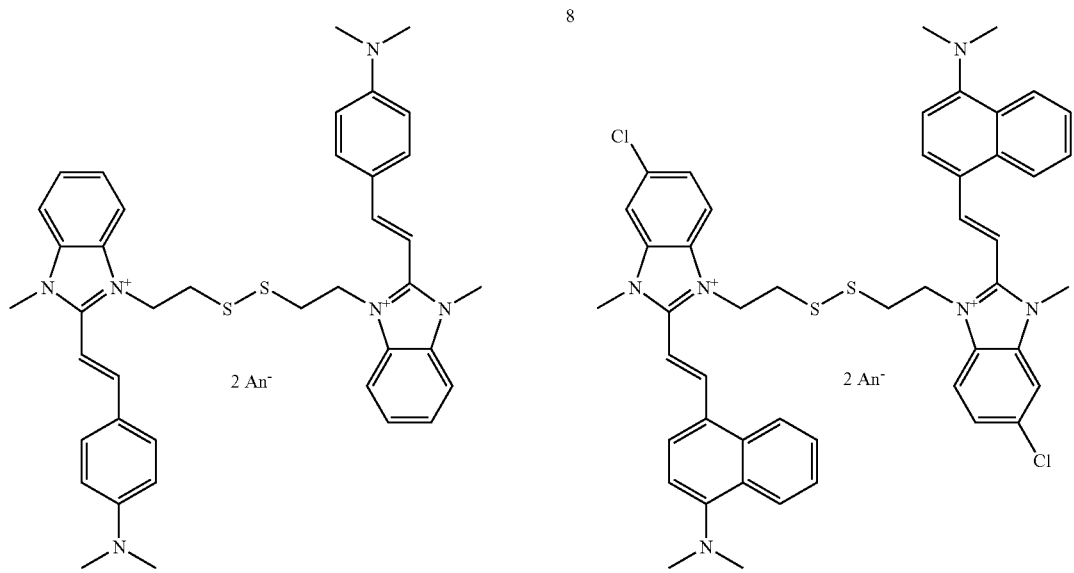
8
9
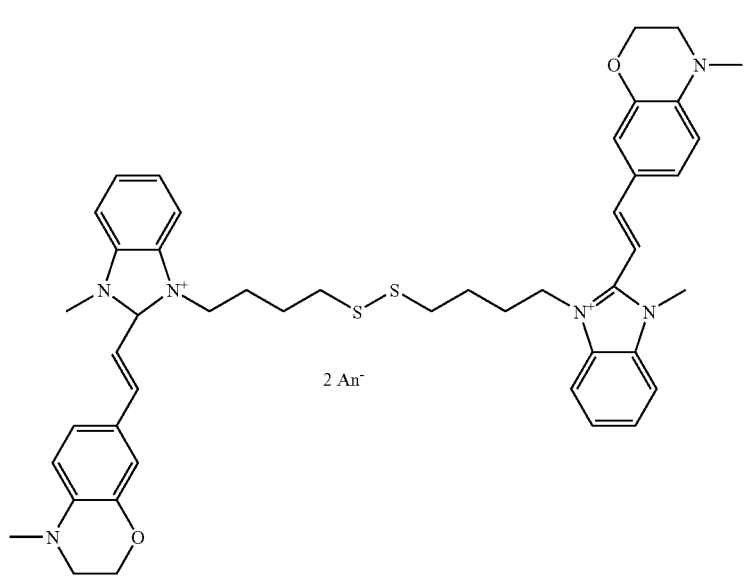
10

-continued
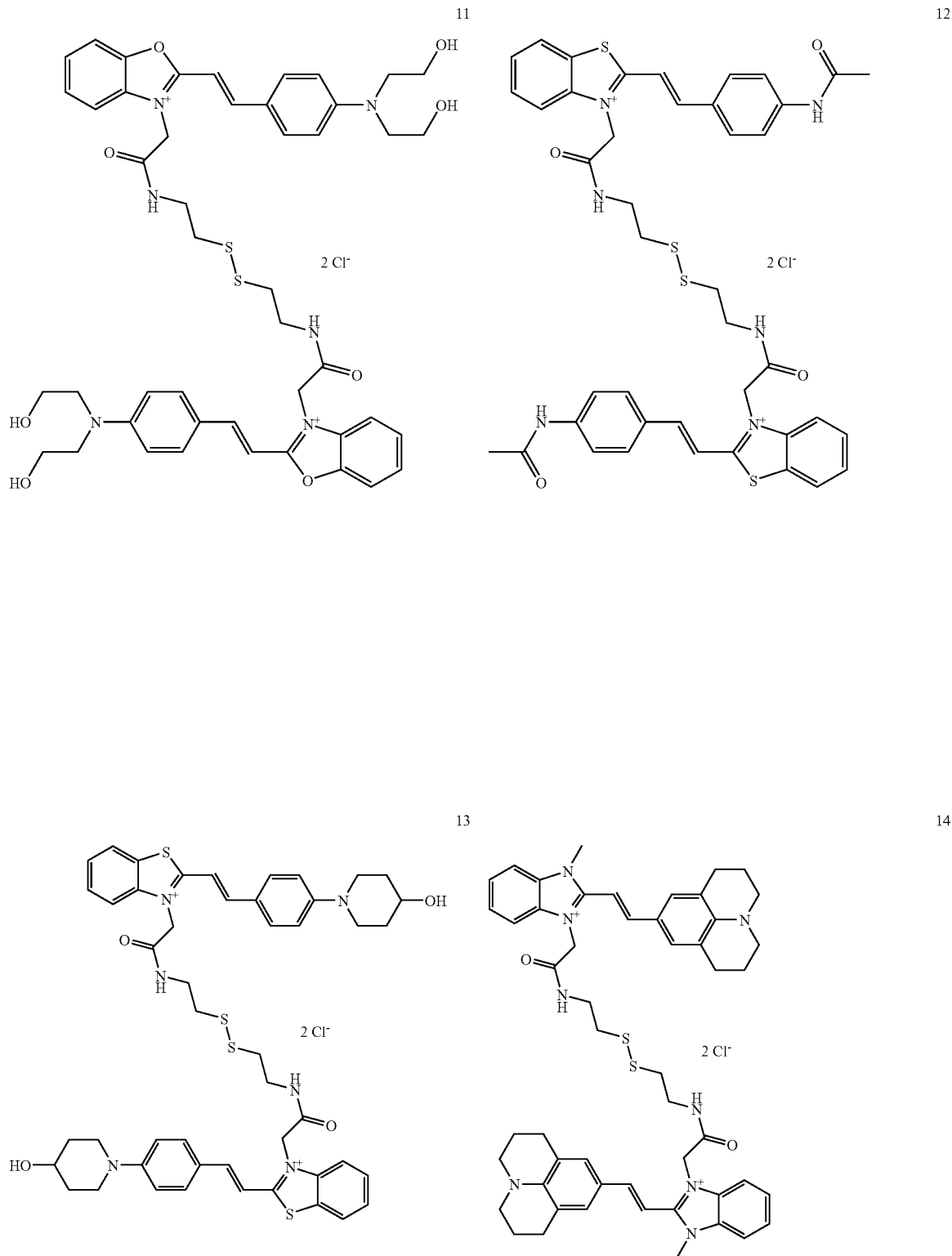

-continued
15
16
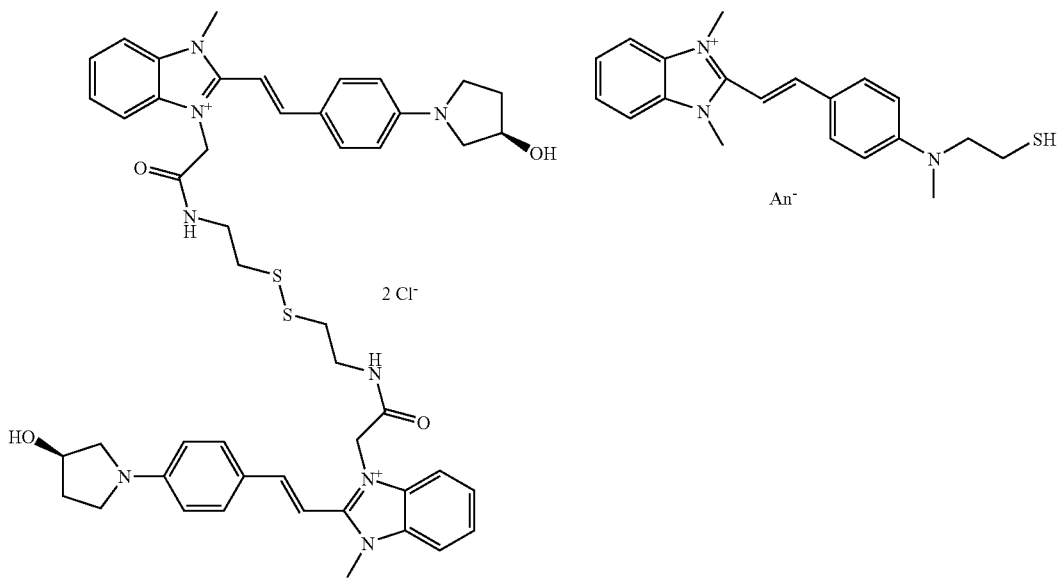
17
18
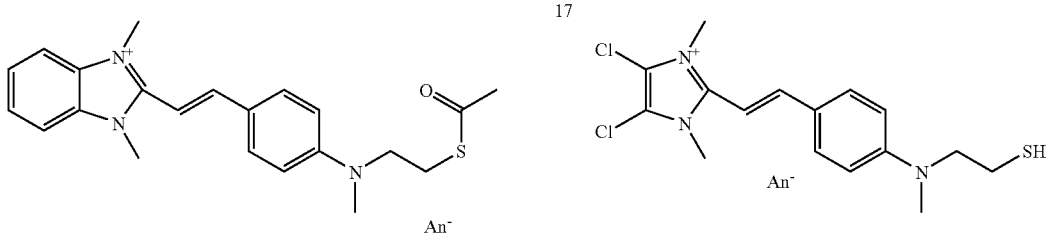
19
20
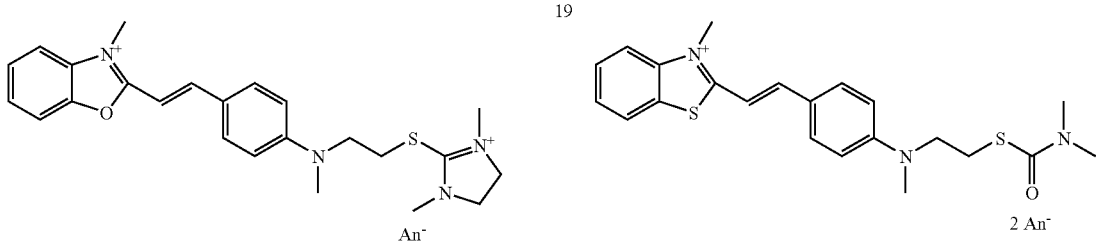
21
22
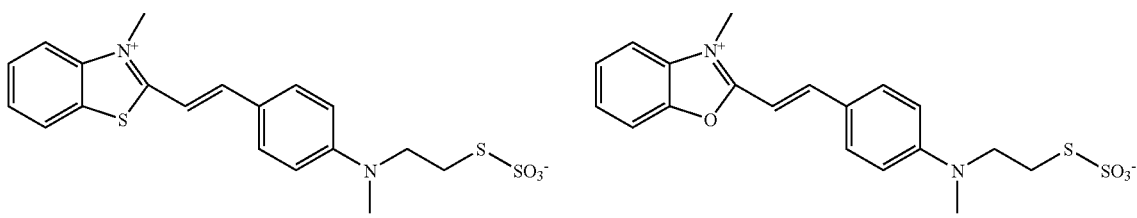

-continued
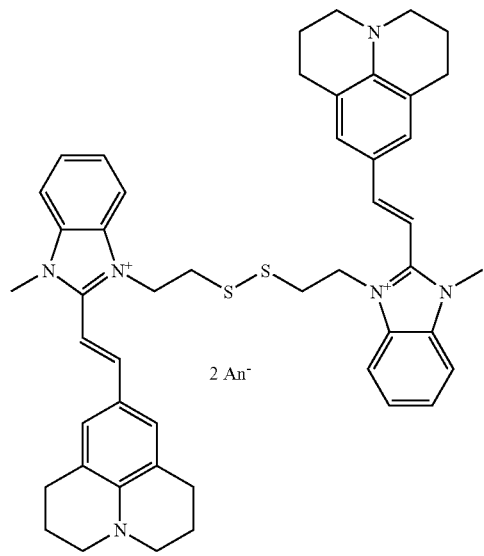
23
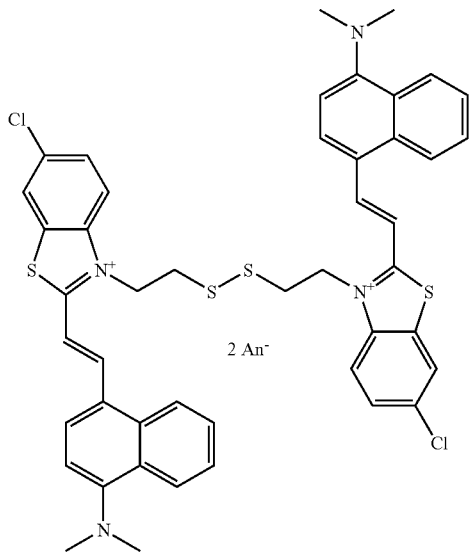
24
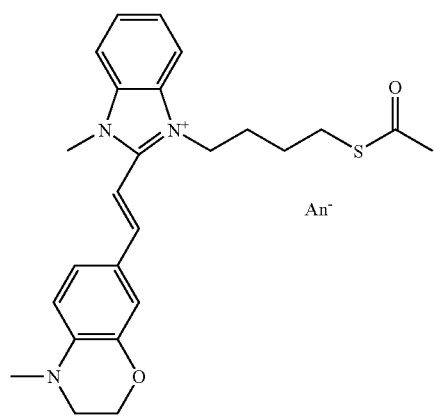
25
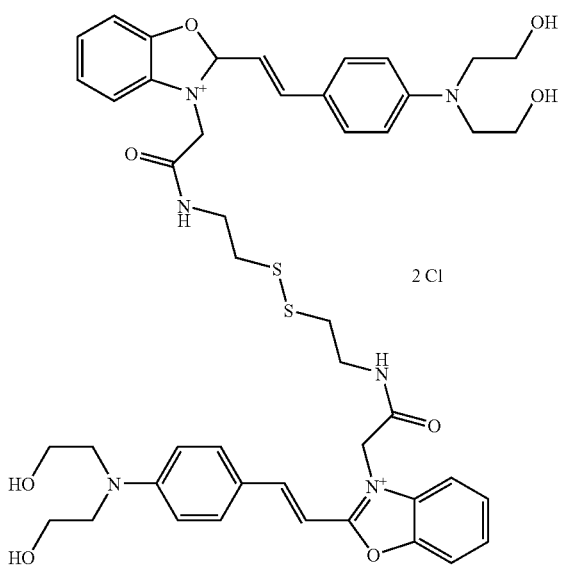
26
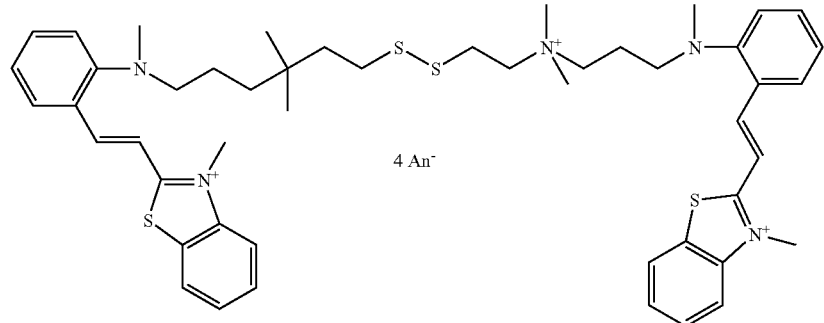
27

-continued
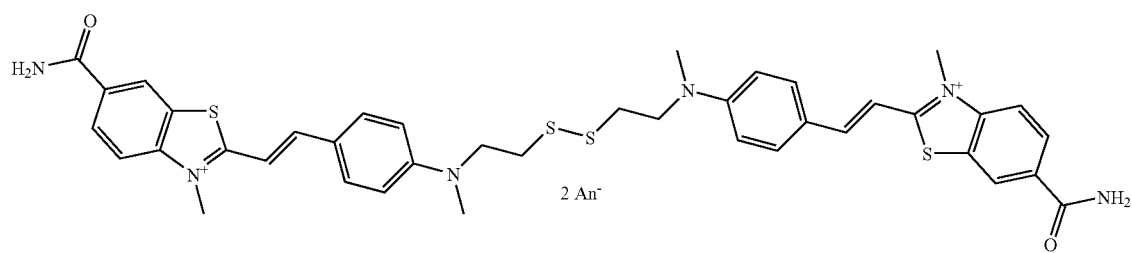
28
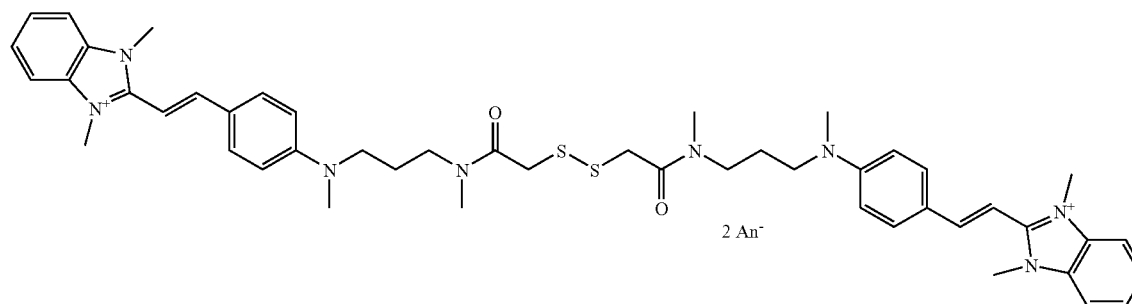
29
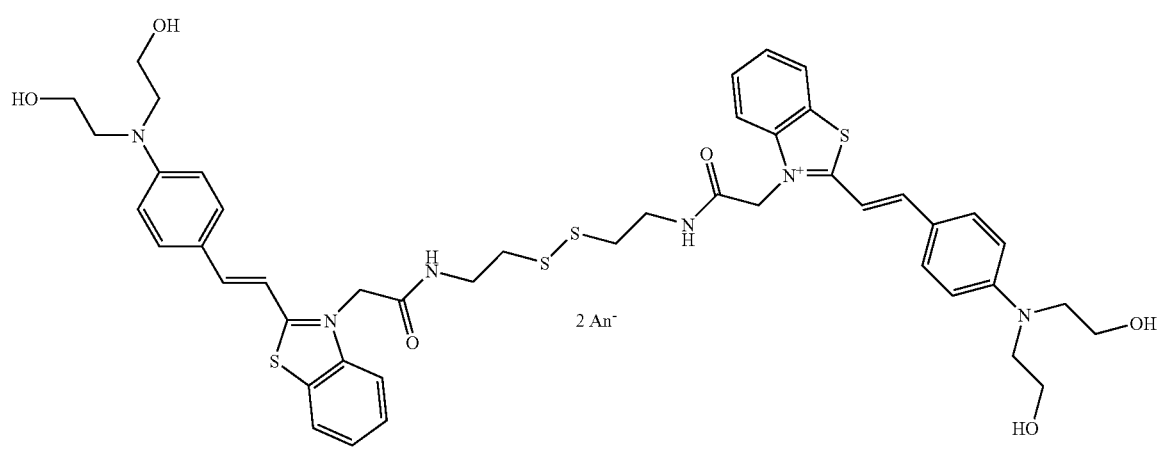
30
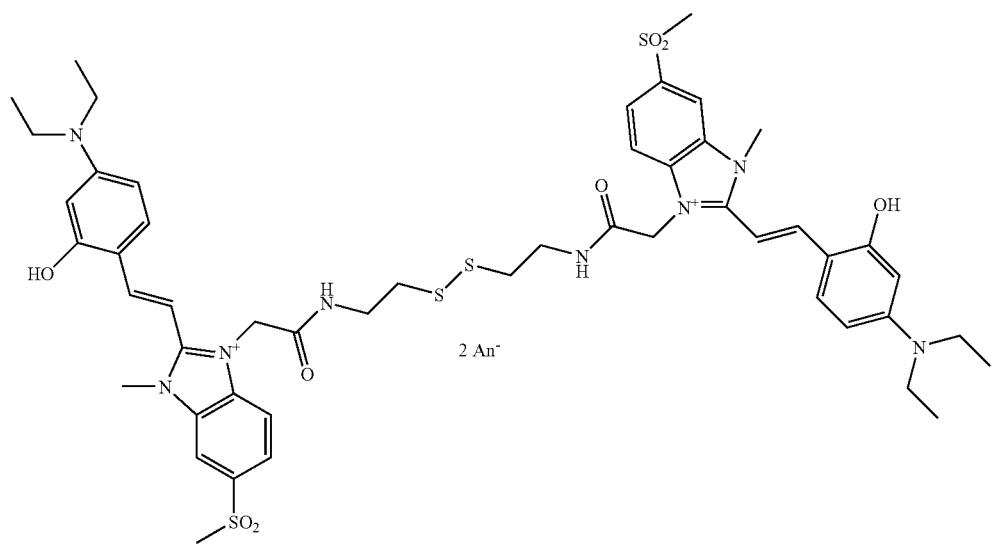
31

-continued
32
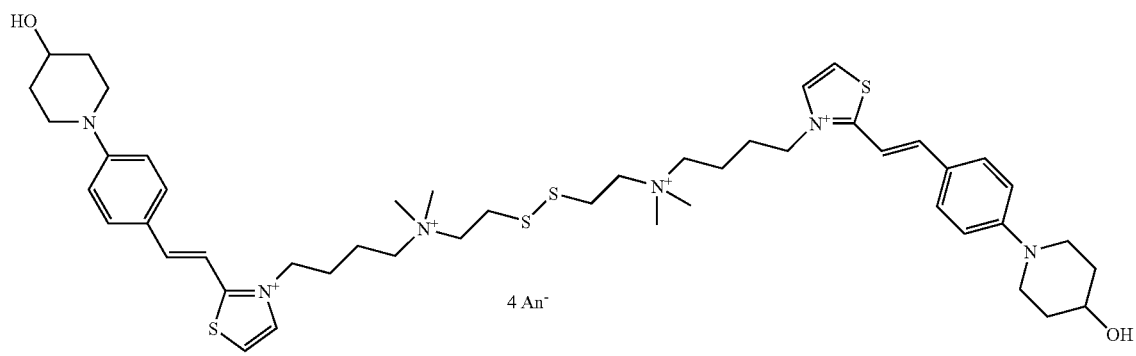
33
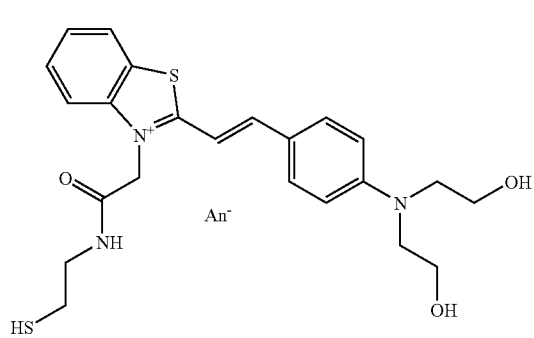
34
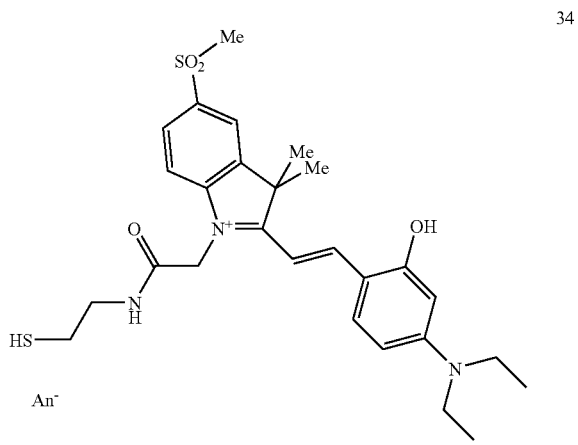
35
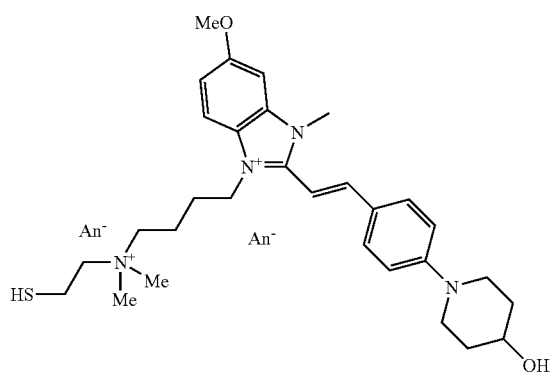
36
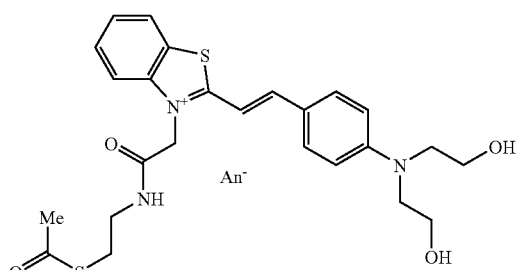
37
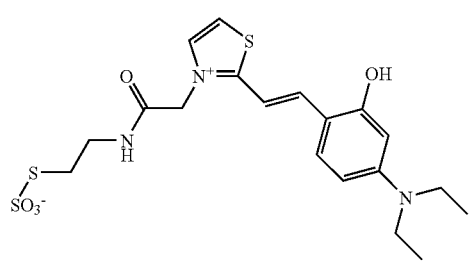
38
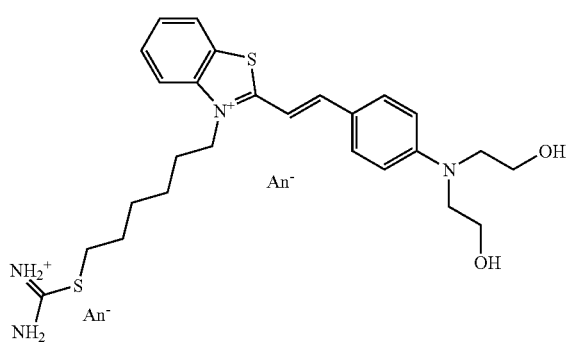

39

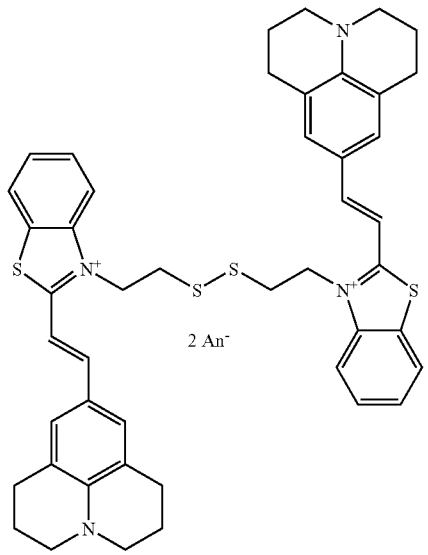

40

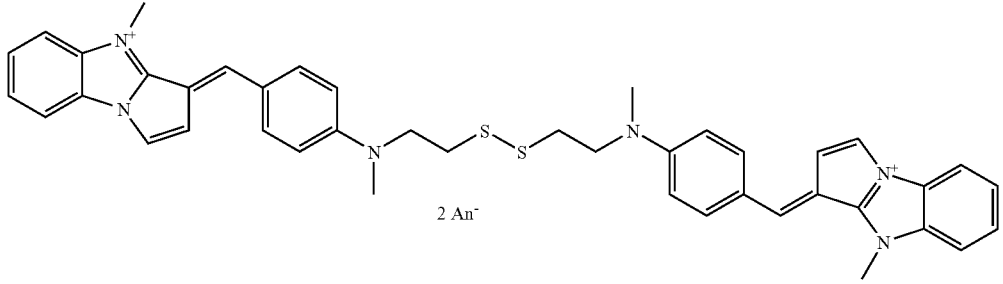

41

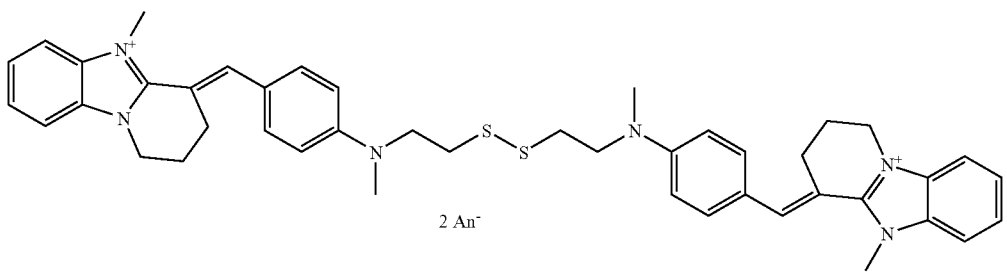

42

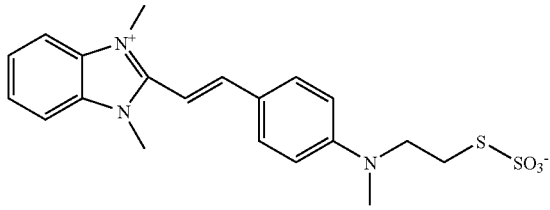

wherein An⁻, which may be identical or different, is an anionic counterion.

For all the following exemplary embodiments for preparing the new thiol and disulfide hemicyanin styryl fluorescent dyes of formula (I) and (II), it is known by those skilled in the art how to pre-protect the reactive functions, such as ketone functions, of the chromophore and then to deprotect them for the needs of the synthesis reaction, by the known conventional protection/deprotection methods such as those described in the books "Protective Groups in Organic Synthesis", T. W. Greene, John Wiley & Sons Publishers, NY, 1981, and "*Protecting Groups*", P. Kocienski, Thieme, 3rd ed., 2005.

Non-limiting example of the protected thiol dyes of formula (I-Y) or (II-Y) for which m and n are 1 can be synthesized in two stages. The first stage consists in preparing the nonprotected thiol dye (I-H) or (II-H) according to the methods known to those skilled in the art, for instance those methods described in "*Thiols and organic sulfides*", "*Thiocyanates and isothiocyanates, organic*", Ullmann's Encyclopedia, Wiley-VCH, Weinheim, 2005. In addition, the second step consists in protecting the thiol function according to the conventional methods known to those skilled in the art in order to produce the protected thiol dyes of formula (I-Y) or (II-Y). By way of non-limiting example, for protecting the thiol function —SH of the thiol dye, use may be made of the methods in the books "*Protective Groups in Organic Synthesis*", T. W. Greene, John Wiley & Sons Ed., NY, 1981, pp. 193-217 and "*Protecting Groups*", P. Kocienski, Thieme, 3rd Ed., 2005, Chap. 5. This method can be illustrated by means of the method comprising i) in generating hemicyanin styryl thiol dyes of formula (I-H) or (II-H) by reduction of a hemicyanic styryl two-chromophore dye bearing a disulfide function —S—S— such as (I-S) or (II-S) and ii) in protecting said thiol function of (I-H) or (II-H), according to the conventional methods, with the reactant 7 Y'R in order to obtain the protected hemicyanin styryl thiol dyes of formula (I-Y) or (II-Y). The thiol compound (I-H) or (II-H) may also be metallated with an alkali metal or alkaline earth metal Met* so as to produce the thiolate fluorescent dye of formula (I-Met) or (II-Met).

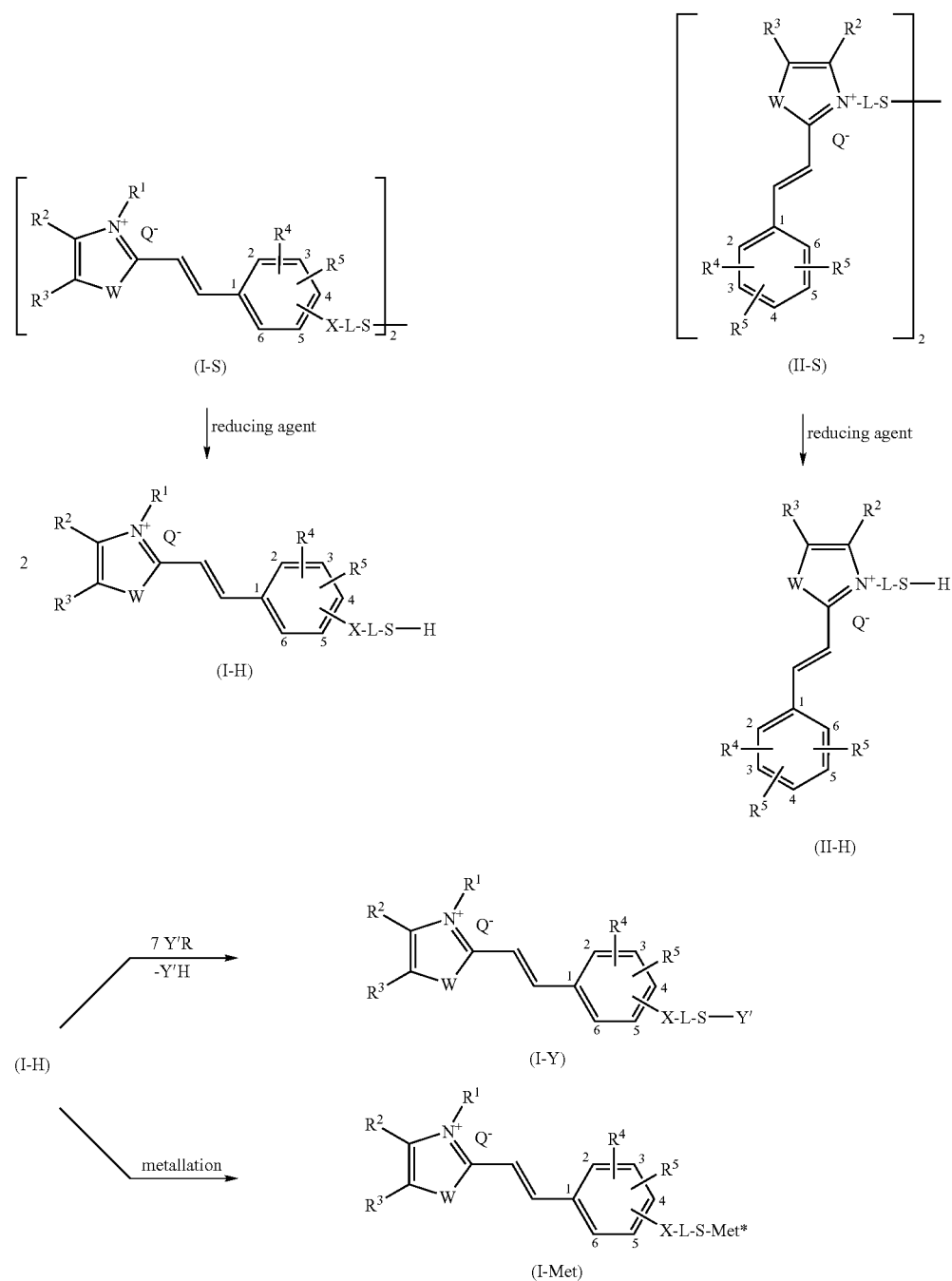

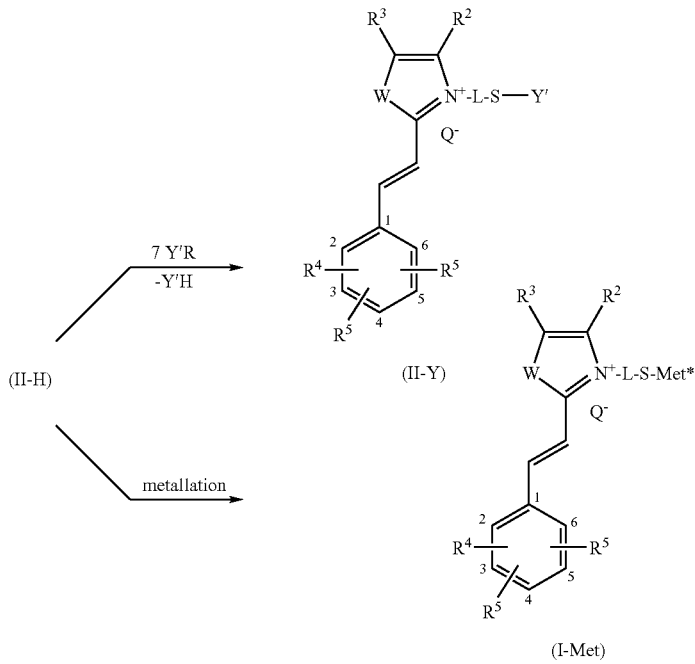

wherein Y' is a thiol-function-protecting group; Met* is chosen from an alkali metal and an alkaline earth metal, for example sodium or potassium, it being understood that, when the metal is an alkaline earth metal, 2 chromophores comprising a thiolate —S⁻ function can be associated with 1 Metal$^{2+}$; and wherein $R^1$ to $R^6$, W, X, Q⁻ and L are defined as above; Y' is a thiol-function-protecting group; and R is a nucleofuge leaving group, for instance mesylate, tosylate, triflate, or halide.

In a further non-limiting example, a protected thiol compound (b) protected with a protecting group Y' as defined above, prepared according to one of the procedures described in the books described above, said protected thiol compound comprising at least one nucleophilic function, can be reacted with a sufficient, for example equimolar, amount of a hemicyanin styryl chromophore (a) or (a₁), and which comprises an electrophilic function in order to form a covalent bond in a Σ linking group, see below, the preparation of dyes of formulae (I'-Y) and (I'-Y):

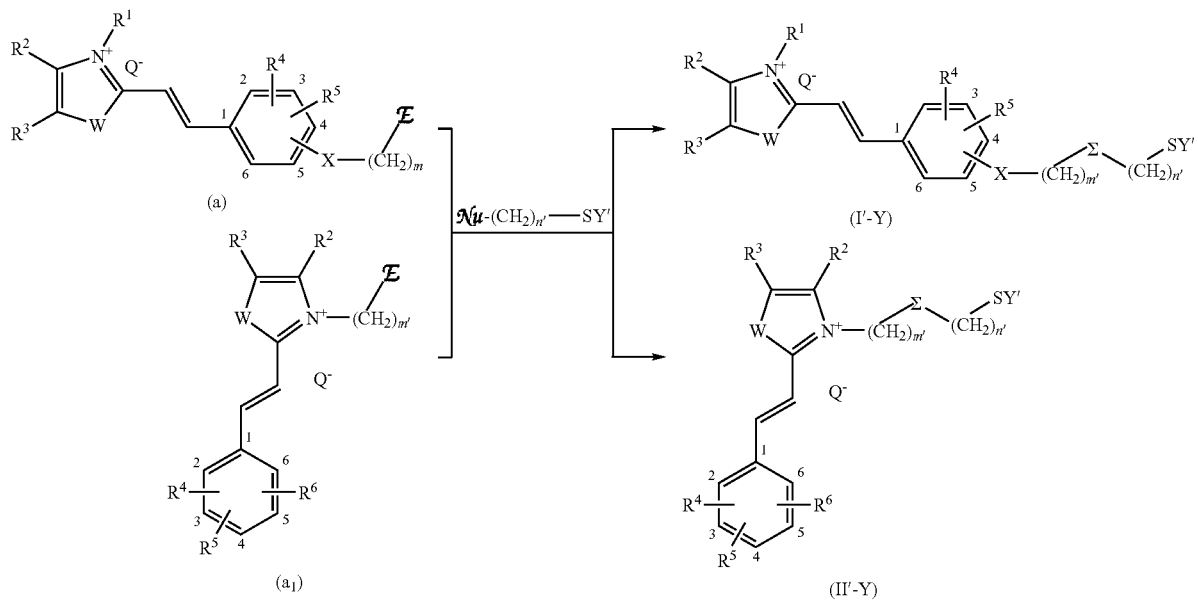

wherein $R^1$ to $R^6$, W, X, $Q^-$ are defined as above; m' and n' are integers ranging from 1 to 6 with m'+n' being an integer ranging from 2 to 6, $Nu$ is a nucleophilic group; $E$ is an electrophilic group; and $\Sigma$ is the linking group generated after attack by the nucleophile on the electrophile.

By way of non-limiting example, the $\Sigma$ covalent bonds that can be generated are listed in the table below based on condensation of electrophiles with nucleophiles:

| Electrophiles E | Nucleophiles Nu | $\Sigma$ Covalent bonds |
| --- | --- | --- |
| Activated esters* | Amines | Carboxamides |
| Acyl nitrides** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |
| Sulfonic acids and salts thereof | Thiols | Thioethers |
| Sulfonic acids and salts thereof | Carboxylic acids | Esters |
| Sulfonic acids and salts thereof | Alcohols | Ethers |
| Anhydrides | Alcohols | Esters |
| Anhydrides | Amines | Carboxamides |
| Aryl halides | Thiols | Thioethers |

-continued

| Electrophiles E | Nucleophiles Nu | $\Sigma$ Covalent bonds |
| --- | --- | --- |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulfonic esters | Amines | Alkylamines |
| Sulfonic esters | Thiols | Thioethers |
| Sulfonic esters | Carboxylic acids | Esters |
| Sulfonic esters | Alcohols | Ethers |
| Sulfonyl halides | Amines | Sulfonamides |

*the activated esters of general formula —CO-Part wherein Part is a leaving group such as oxysuccinimidyl, oxybenzotriazolyl, aryloxy which is optionally substituted;
**the acyl nitrides may rearrange to give isocyanates.

By way of further non-limiting example, this process may be varied to use a hemicyanin styryl chromophore having an electrophilic acrylate function (—OCO—C═C—) on which is carried out an addition reaction that will generate a $\Sigma$ bond.

By way of further non-limiting example, it is also possible to use a thiol reactant ($\alpha$): Y'—SH comprising a Y' group as defined above, the nucleophilic SH function of which can react with the carbon atom of the radical L in the $\alpha$-position with respect to the halogen atom borne by a hemicyanin styryl chromophore of (a') or ($a_1$') styryl, so as to give the protected thiol (I-Y) or (II-Y) dye of formula as defined above:

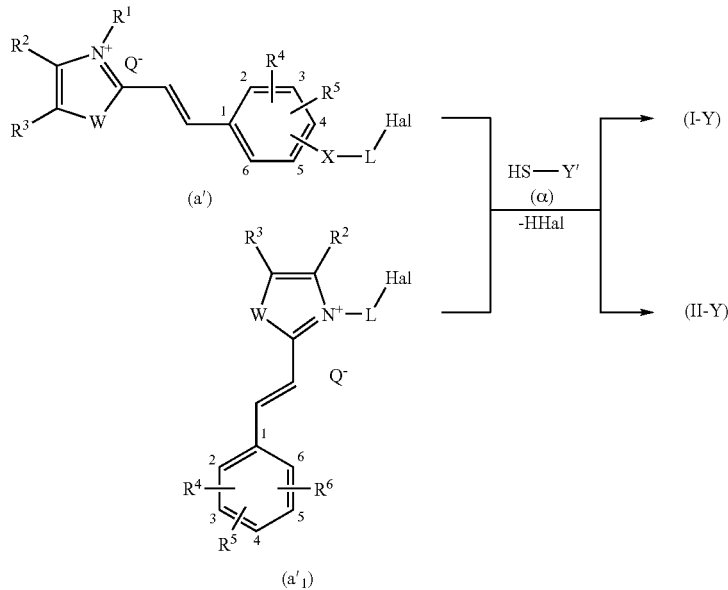

wherein $R^1$ to $R^6$, W, X, L, $Q^-$, (I-Y) and (II-Y) are defined as above, and Hal is a nucleofuge halogen atom such as bromine, iodine, or chlorine.

In at least one embodiment, a nucleofuge leaving group may be replaced with a derivative of thioureas (S═C(NRR)NRR), or thiourea, so as to generate isothiouroniums; for example, based on chromophores (a') or ($a'_1$) as defined above if the thiourea group is an imidazoline thione ($\beta$) (or its thiodehydroimidazolium tautomeric form), so as to give the dye which is S-protected with an imidazolinium group (I"-Y) or (II"-Y):

-continued

| Electrophiles E | Nucleophiles Nu | $\Sigma$ Covalent bonds |
| --- | --- | --- |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-acylureas or anhydrides |
| Diazoalkanes | Carboxylic acids | Esters |
| Epoxides | Thiols | Thioethers |
| Haloacetamides | Thiols | Thioethers |

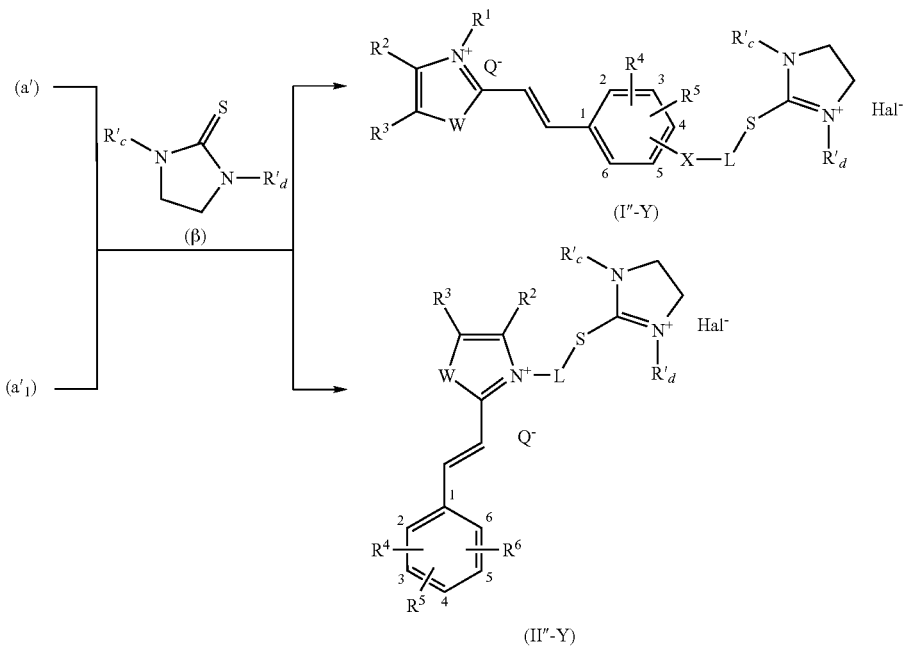
wherein (a'), (a₁'), R'_c, R'_d, R¹ to R⁶, W, X, L, Q⁻, and Hal⁻ are defined as above.
In at least one embodiment, the compound (I"-Y') or (II"-Y') may be obtained using a cyclic thiourea derivative of thioimidazole type (b'), followed by alkylation of said imidazole using R'_d-Lg, with Lg being a leaving group such as chloride, bromide, tosylate or mesylate:

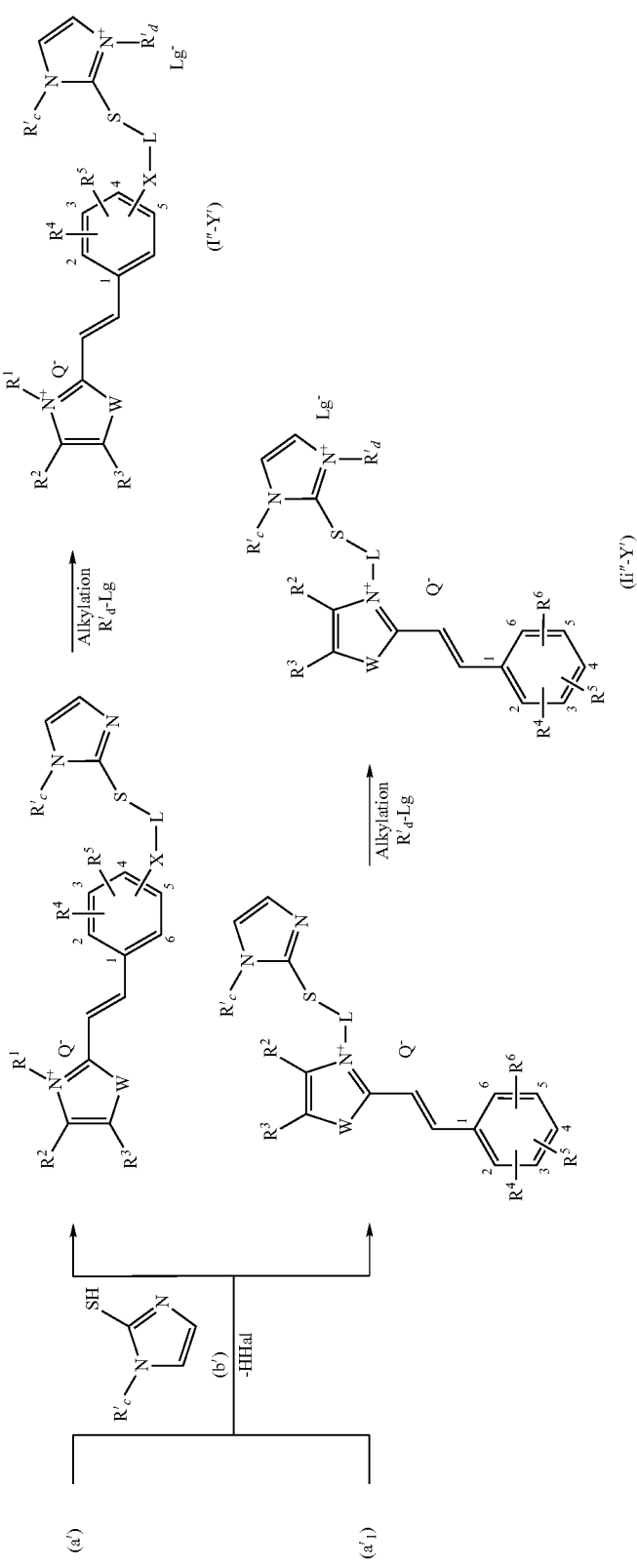

wherein $R^1$ to $R^6$, X, L, (a'), (a'$_1$), Q$^-$, Hal, Lg, R'$_c$, and R'$_d$ are defined as above.

In at least one embodiment, in place of the halide comprising the fluorescent chromophore (a') or (a'$_1$), a chromophore comprising another type of nucleofuge such as tosylate or mesylate is used.

In at least one embodiment, certain protected thiol dyes (I'-Y) or (II'-Y) can be obtained by reacting a protected thiol compound with a compound bearing two carboxylic acid functions that are activated, according to the conventional methods (for example, reaction with a carbodiimide or with thionyl chloride). The resulting product (d) is subsequently reacted with a hemicyanin styryl chromophore (c) or (c$_1$) bearing a nucleophilic function, for example of primary or secondary amine type, or of aliphatic alcohol type.

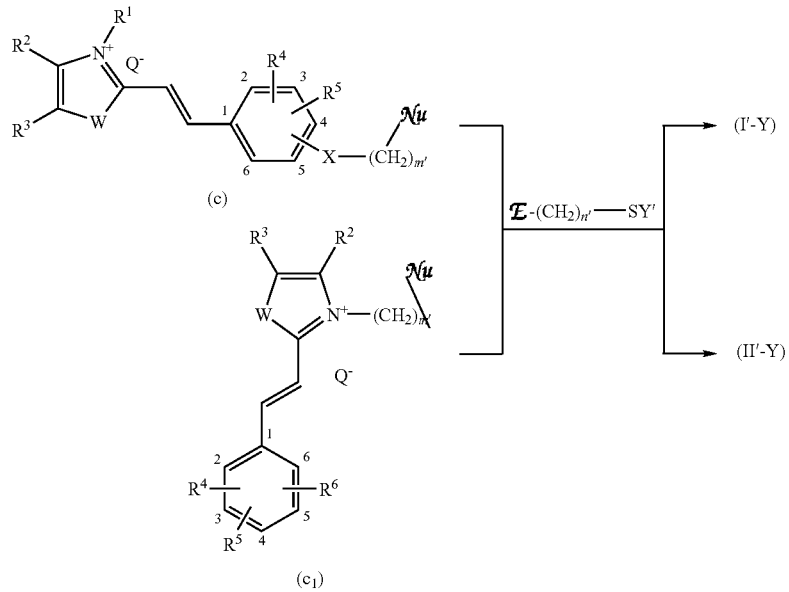

wherein $R^1$ to $R^6$, m', n', W, X, Q$^-$, $\mathcal{E}$, $\mathcal{N}u$, Y', (I'-Y), and (II'-Y) are defined as above.

By way of non-limiting example, another variant is to use a thiolactone derivative based on particular nucleophilic chromophores (c') and (c'$_1$) so as to give the derivatives (I'-H) or (II'-H) comprising a linker L interrupted with an amide function as represented by the scheme below:

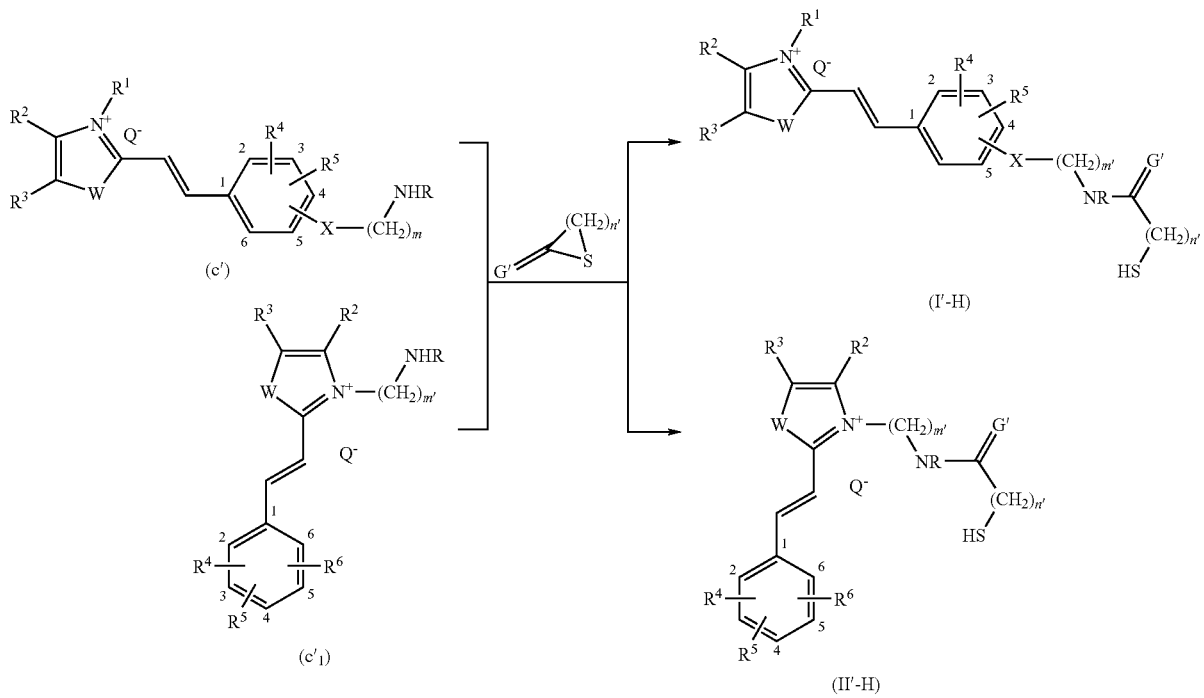

wherein $R^1$ to $R^6$, R, W, X, $Q^-$, n' and m' are defined as above, G' is chosen from an oxygen atom, a sulfur atom, and an NR' group wherein R' is chosen from a hydrogen atom and a alkyl radical, and R is chosen from a hydrogen atom, a $C_1$-$C_4$ alkyl radical, a $C_1$-$C_4$ hydroxyalkyl radical, and an aryl($C_1$-$C_4$) alkyl. In at least one embodiment, the thiolactone derivative is chosen wherein n' is 3 and G' is an oxygen atom.

The derivatives (I'-H) or (II'-H) comprising a free SH function can subsequently be protected or metallated as seen above.

In accordance with another non-limiting possibility, the protected thiol dyes of formula (I'''-Y) and (II'''-Y) can be obtained by reaction of a compound (d') comprising a thiol group protected with a Y' group, and a nucleofuge leaving group Lg, for instance mesylate, tosylate, triflate, or halide, with a hemicyanin styryl chromophore (c') or (c").

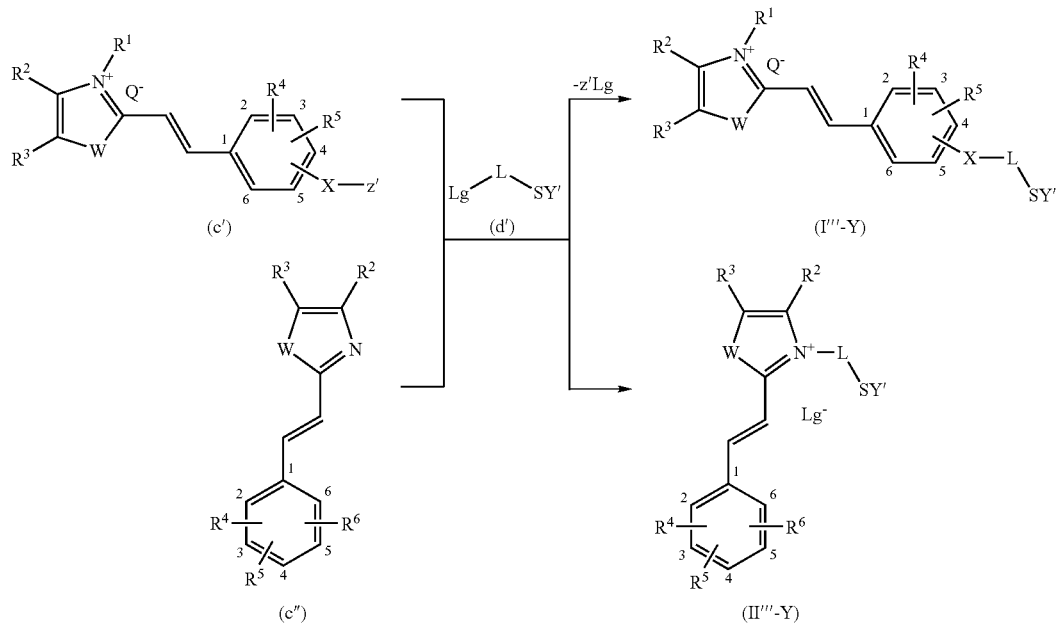

wherein $R^1$ to $R^6$, p', W, X, L and $Q^-$ are defined as above and z' is chosen from a hydrogen atom and a group activating the nucleophilicity of X. In formula c', Z' may also be a tertiary amine group or a nitrogenous heterocycle group, associated with X, capable of substituting the leaving group Lg; in this case, the compound (I'''-Y) will comprise, as counterion that is additional to $Q^-$, the group $Lg^-$.

By way of non-limiting example, a compound comprising a protected thiol group (I'''-Y) or (II'''-Y) comprises a nucleofuge leaving group R, for instance mesylate, tosylate, or triflate, which can undergo nucleophilic attack from the amine of the hemicyanin styryl chromophore (c') or (c") as follows:

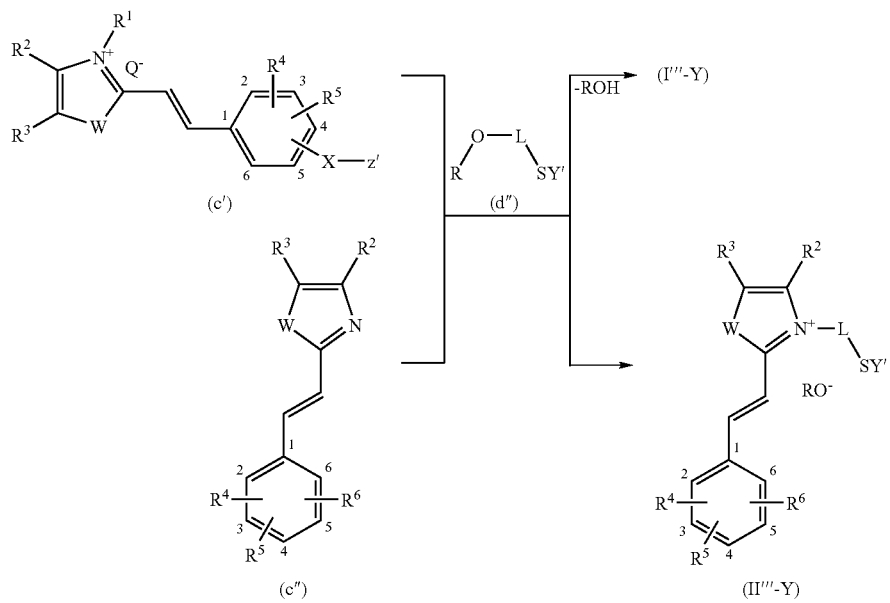

wherein $R^1$ to $R^6$, L, and W are defined as above.

For further details on the operating conditions used for the processes mentioned above, reference may be made to the book *Advanced Organic Chemistry*, "Reactions, Mechanisms and Structures", J. March, 4th Ed., John Wiley & Sons, 1992 or "*Protective Groups in Organic Synthesis*" T. W. Greene, John Wiley & Sons Ed., NY, 1981.

The hemicyanin styryl thiol dyes formed can be converted to —SY' protected thiol fluorescent dyes by protection of the —SH thiol using the conventional protecting groups. The thiol fluorescent dyes are metallated by also using the conventional methods known to those skilled in the art, such as those described in *Advanced Organic Chemistry*, "Reactions, Mechanisms and Structures", J. March, 4th Ed., John Wiley & Sons, NY, 1992.

The protected hemicyanin styryl thiol dyes can be deprotected by conventional pathways such as those described in the books "*Protective Groups in Organic Synthesis*", T. W. Greene, John Wiley & Sons Ed., NY, 1981; "*Protecting Groups*", or P. Kocienski, Thieme, 3rd Ed., 2005.

The starting reactants are commercially available or accessible by conventional methods known to those skilled in the art.

The fluorescent disulfide dyes of formula (I) and (II) can be synthesized by oxidation of the fluorescent thiol dyes.

This method can be illustrated by means of the method consisting in generating hemicyanin styryl disulfide dyes of formula (I-S) or (II-S) by oxidation of a hemicyanin styryl thiol dye, such as (I-H) or (II-H).

The oxidation can be carried out with an oxidizing agent optionally associated with an alkaline agent. Any oxidizing agent that is conventional in the field may be used, for example hydrogen peroxide, urea peroxide, alkali metal bromates, persalts such as perborates and persulfates, and also enzymes, among which non-limiting mention may be made of peroxidases, 2-electron oxidoreductases such as uricases, and 4-electron oxygenases such as laccases. In at least one embodiment, hydrogen peroxide is used. The alkaline agent is, for example, chosen from aqueous ammonia, amines including ethanolamine, carbonate salts, or hydrogen carbonate salts.

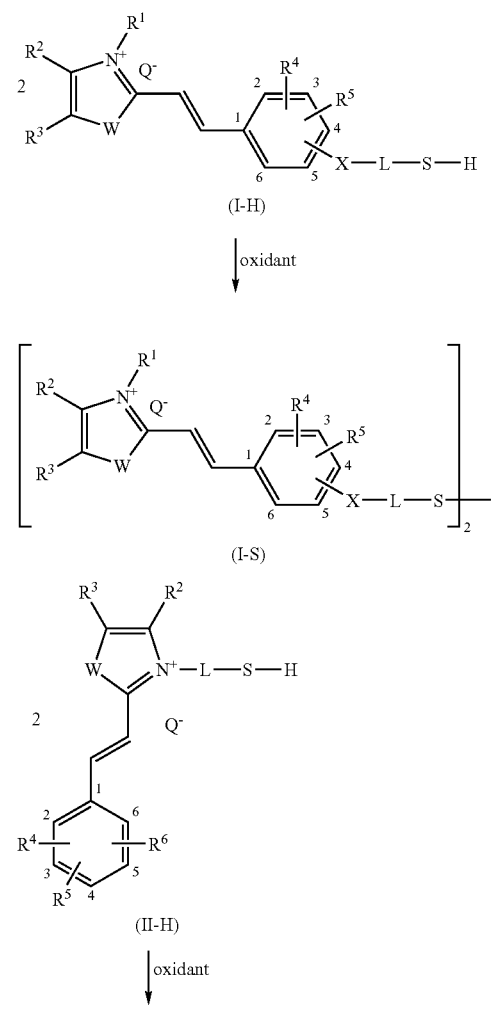

-continued

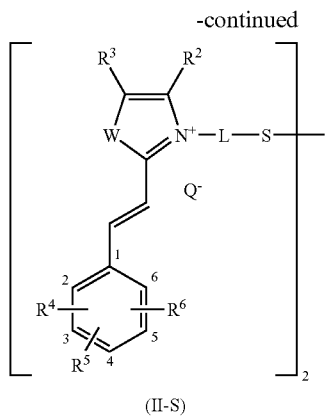

(II-S)

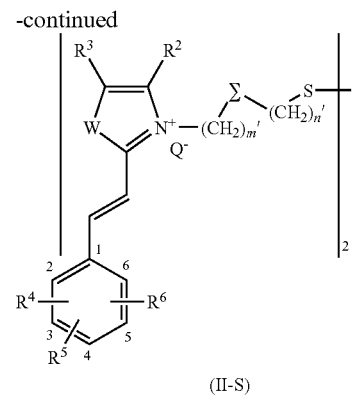

(II-S)

wherein $R^1$ to $R^6$, L, W, X, and $Q^-$ are defined as above.

By way of further non-limiting example, a disulfide compound (b1), said disulfide compound comprising two nucleophilic functions, can be reacted with a sufficient amount, for example two equivalents, of a hemicyanin styryl chromophore (a) or ($a_1$), and which comprises an electrophilic function so as to form a Σ covalent linking group; it being understood that $(CH_2)_m$——$(CH_2)_n$ is a subset of L according to the definition given for formulae I and II; see below, the preparation of dyes of formulae (I-S) and (II-S):

wherein $R^1$ to $R^6$, m', n', W, X, $Q^-$, Σ, $\mathcal{E}$ and $\mathcal{N}u$ as defined above.

One non-limiting variant of this process is to use a hemicyanin styryl chromophore having an electrophilic acrylate function (—OCO—C=C—) on which is carried out an addition reaction that will generate a covalent bond in a Σ linking group.

According to another non-limiting possibility, a disulfide compound (b2), said disulfide compound comprising two electrophilic functions, can be reacted with a sufficient amount, for example two equivalents, of a hemicyanin styryl chromophore (c2) or (c3), and which comprises a nucleophilic function, so as to form a Σ linking group; see below, the preparation of dyes of formulae (I-S) and (II-S):

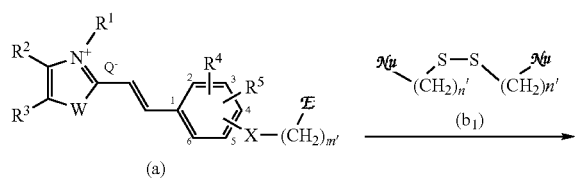

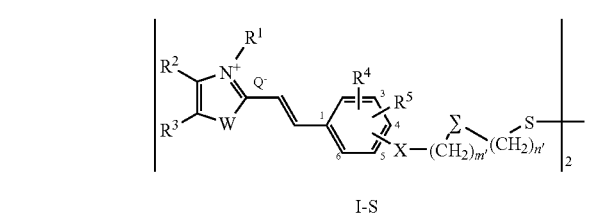

I-S

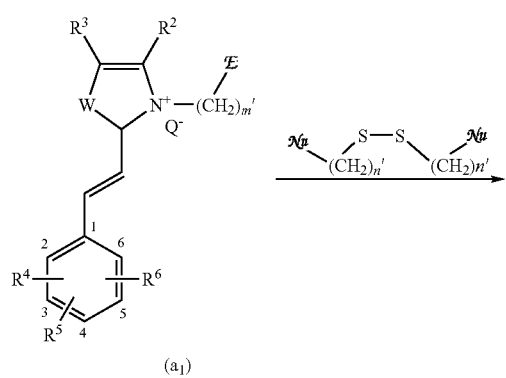

($a_1$)

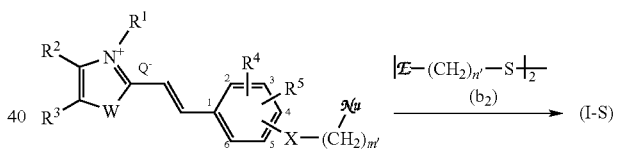

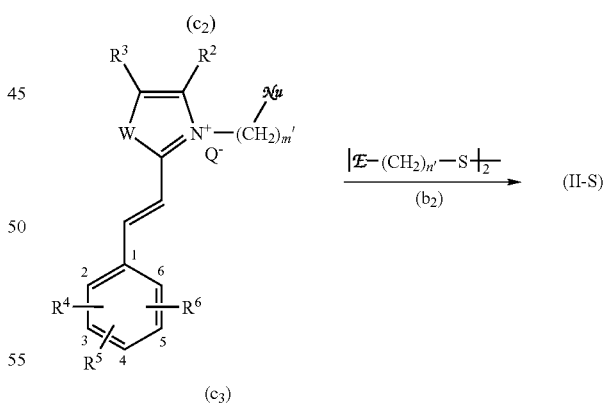

wherein $R^1$ to $R^6$, m', n', W, X, $Q^-$, $\mathcal{E}$, $\mathcal{N}u$, (I'-Y), and (II'-Y) are defined as above.

By way of further non-limiting example, the disulfide dyes of formula (I-S) and (II-S) can be obtained by reaction of a compound (d") comprising a disulfide group and two nucleofuge leaving groups Lg, for instance mesylate, tosylate, triflate, or halide, with a hemicyanin styryl chromophore (c4) or (c5).

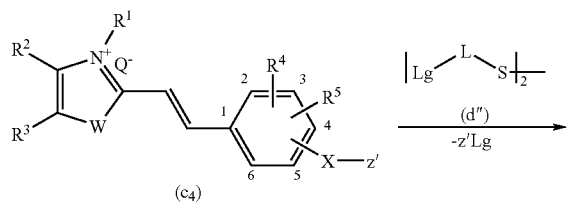

(c4)

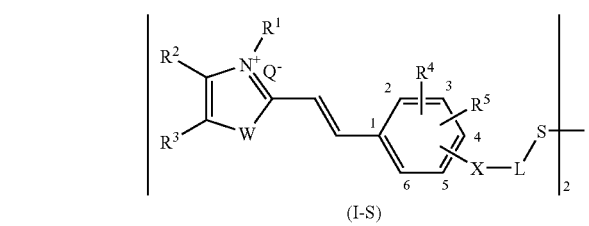

(I-S)

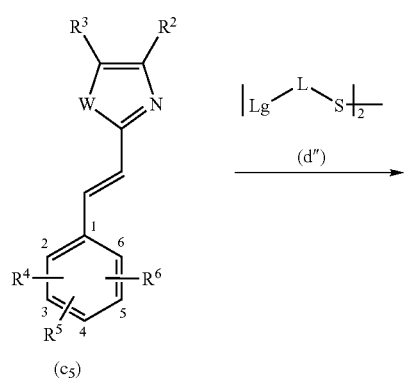

(c5)

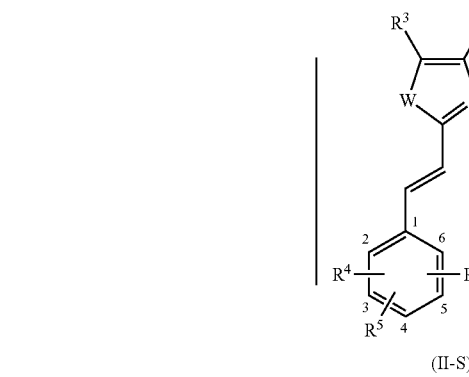

(II-S)

wherein $R^1$ to $R^6$, p', W, X, L, z', and $Q^-$ are defined as above.

In accordance with another non-limiting possibility, the disulfide dyes of formula (I) or (II) according to the present disclosure can be obtained by reaction of a compound comprising a disulfide group and an electrophilic group (f), with a heterocyclic compound comprising a nucleophilic group. By way of non-limiting example, an aldehyde or a thioaldehyde when G' is chosen from an oxygen atom and a sulfur atom may be condensed with an "activated methylene" such as the cationic heteroaryl derivative (e) or (e') so as to generate an ethylene bond >C=C<. This reaction is commonly referred to as "Knoevenagel" condensation:

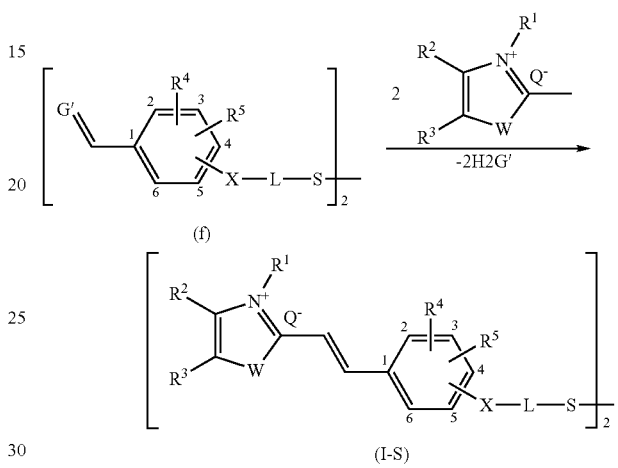

wherein $R^1$ to $R^6$, W, X, L and $Q^-$ are defined as above. G' is chosen from an oxygen atom and a sulfur atom.

For further details on the operating conditions used for the processes mentioned above, reference may be made to the book *Advanced Organic Chemistry*, "Reactions, Mechanisms and Structures", J. March, 4th Ed., John Wiley & Sons, 1992.

The starting reactants are commercially available or accessible by conventional methods known to those skilled in the art.

By way of non-limiting example, mention may be made of the synthesis of the dye (I), and subsequently the reactants (I') or (I"), using two equivalents of derivative (g) and one equivalent of disulfide reactant 2 comprising two aryls or heteroaryls B, comprising an electrophilic function, such as aldehyde or thioaldehyde, or a disulfide reactant comprising an activated methylene 3 comprising with two equivalents of electrophilic reactant derived from aryl or heteroaryl (g'), so as to give, by double Knoevenagel condensation, the styryl disulfide derivatives (I).

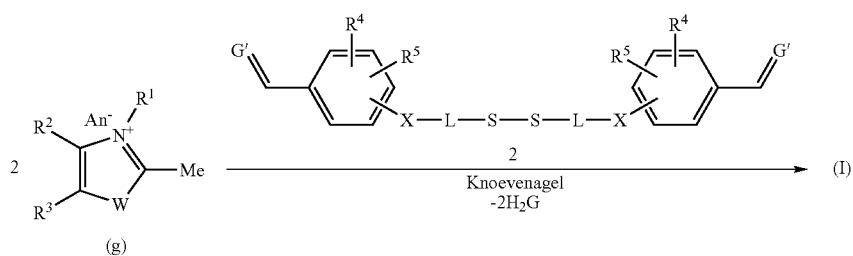

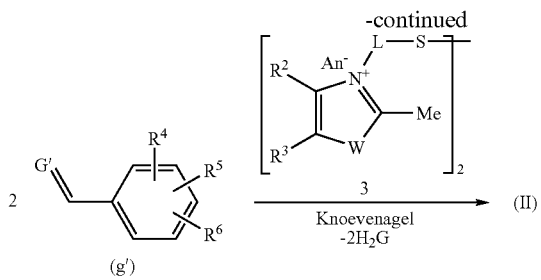

wherein $R^1$ to $R^6$, $An^-$, L, X, G', W, and (I) and (II) are defined as above.

The composition of the present disclosure contains at least one disulfide, thiol, or protected-thiol hemicyanin styryl fluorescent dye of formula (I) or (II). In addition to the presence of at least one fluorescent dye of formula (I) or (II), the composition of the present disclosure may also contain a reducing agent.

Suitable non-limiting examples of this reducing agent may be chosen from thiols, for example cysteine, homocysteine, or thiolactic acid, the salts of these thiols, phosphines, bisulfite, sulfites, thioglycolic acid, and also its esters, including glyceryl monothioglycolate, and thioglycerol. This reducing agent may also be chosen from borohydrides and derivatives thereof, for instance the salts of borohydride, of cyanoborohydride, of triacetoxyborohydride, or of trimethoxyborohydride: sodium salts, lithium salts, potassium salts, calcium salts, quaternary ammonium (tetramethylammonium, tetraethylammonium, tetra-n-butylammonium or benzyltriethylammonium) salts; and catechol borane.

A non-limiting example of the dye composition that can be used in the present disclosure comprises an amount of dye of formula (I) or (II) ranging from 0.001% to 50% relative to the total weight of the composition. For example, this amount may range from 0.005% to 20% by weight, and further for example may range from 0.01% to 5% by weight, relative to the total weight of the composition.

The dye composition may also contain additional direct dyes. These direct dyes are, for example, chosen from neutral, acidic, or cationic nitrobenzene direct dyes, neutral, acidic, or cationic azo direct dyes, tetraazapentamethine dyes, neutral, acidic, or cationic quinone, such as anthraquinone dyes, azine direct dyes, triarylmethane direct dyes, indoamine direct dyes, and natural direct dyes.

Non-limiting examples of the natural direct dyes include lawsone, juglone, alizarin, purpurin, carminic acid, kermesic acid, purpurogallin, protocatechaldehyde, indigo, isatin, curcumin, spinulosin, and apigenindin. Extracts or decoctions containing these natural dyes, including poultices or henna-based extracts, may also be used.

The dye composition may contain at least one oxidation base and/or at least one coupler conventionally used for dyeing keratin fibers.

Non-limiting examples of the at least one oxidation base, include para-phenylenediamines, bisphenylalkylenediamines, para-aminophenols, bis-para-aminophenols, ortho-aminophenols, heterocyclic bases, and addition salts thereof.

Non-limiting examples of the at least one coupler, include meta-phenylenediamines, meta-aminophenols, meta-diphenols, naphthalene couplers, heterocyclic couplers, and addition salts thereof.

The at least one coupler may be present in an amount ranging from 0.001% to 10% by weight of the total weight of the dye composition, and in at least one embodiment ranging from 0.005% to 6%.

The at least one oxidation base present in the dye composition may be present in an amount ranging from 0.001% to 10% by weight of the total weight of the dye composition, and in at least one embodiment ranging from 0.005% to 6% by weight.

By way of non-limiting example, the addition salts of the at least one oxidation base and of the at least one coupler that can be used in the context of the present disclosure may be chosen from addition salts with an acid, such as hydrochlorides, hydrobromides, sulfates, citrates, succinates, tartrates, lactates, tosylates, benzenesulfonates, phosphates, and acetates, and addition salts with a base, such as hydroxides of an alkali metal such as sodium or potassium, aqueous ammonia, amines, or alkanolamines.

The medium suitable for dyeing, also called dye support, is a cosmetic medium comprising water or a mixture of water and at least one organic solvent. By way of organic solvent, non-limiting mention may, for example, be made of $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether, and diethylene glycol monomethyl ether, and also aromatic alcohols such as benzyl alcohol or phenoxyethanol, and mixtures thereof.

The solvents, when they are present, may for example be present in proportions approximately between 1% and 40% by weight, relative to the total weight of the dye composition, and further for example approximately between 5% and 30% by weight.

By way of non-limiting example, the dye composition may also contain other adjuvants conventionally used in hair-dyeing compositions, such as anionic, cationic, nonionic, amphoteric, or zwitterionic surfactants or mixtures thereof, anionic, cationic, nonionic, amphoteric, or zwitterionic polymers, or blends thereof, mineral or organic thickeners, anionic, cationic, nonionic, and amphoteric associative polymer thickeners, antioxidants, penetrating agents, sequestering agents, fragrances, buffers, dispersing agents, conditioning agents such as, for example, modified or unmodified, volatile or nonvolatile silicones, such as amino silicones, film-forming agents, ceramides, preservatives, opacifiers, or conductive polymers.

The above adjuvants may, for example, be present in an amount, for each of them, ranging from 0.01% to 20% by weight relative to the weight of the composition.

Those skilled in the art will take care to select the at least one possible additional compound in such a way that the advantageous properties intrinsically associated with the dye composition in accordance with the present disclosure are not, or are not substantially, impaired by the at least one addition envisaged.

The pH of the dye composition may be in the range from approximately 3 to 14, and in at least one embodiment may be in the range from approximately 5 to 11. It may be adjusted to the desired value by means of acidifying or basifying agents normally used in the dyeing of keratin fibers or else by means of conventional buffer systems.

Suitable non-limiting examples of the acidifying agents include mineral or organic acids, such as hydrochloric acid, orthophosphoric acid, sulfuric acid, carboxylic acids, for instance acetic acid, tartaric acid, citric acid or lactic acid, or sulfonic acids.

Suitable non-limiting examples of the basifying agents include aqueous ammonia, alkali carbonates, alkanolamines such as mono-, di- and triethanolamines, and also derivatives thereof, sodium hydroxide or potassium hydroxide, and the compounds of formula (γ) below:

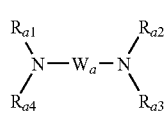

wherein $W_a$ is chosen from a propylene residue optionally substituted with a hydroxyl group and a $C_1$-$C_4$ alkyl radical; $R_{a1}$, $R_{a2}$, $R_{a3}$ and $R_{a4}$, which may be identical or different, are chosen from a hydrogen atom, a $C_1$-$C_4$ alkyl radical, and a $C_1$-$C_4$ hydroxyalkyl radical.

The dye composition may be in other forms, such as in the form of a liquid, a cream, or a gel, or in any other form suitable for dyeing keratin fibers, including the hair.

The process for dyeing keratin materials, such as dark keratin materials, according to the present disclosure, consists in applying, to the keratin materials, a dye composition coupling, in a suitable cosmetic medium, at least one hemicyanin styryl disulfide or thiol fluorescent dye chosen from the dyes of formulae (I) and (II).

According to at least one embodiment, in the process of the present disclosure, the reducing agent may also be applied as a pretreatment before the application of the composition containing at least one hemicyanin styryl fluorescent dye of formula (I) or (II).

This pretreatment may be of short duration, for example from 1 second to 30 minutes, further for example from 1 minute to 15 minutes, with a reducing agent as mentioned above.

According to at least one embodiment, the composition comprising at least one hemicyanin styryl fluorescent dye of formula (I) or (II) also comprises at least one reducing agent as defined above. This composition is then applied to the hair.

When the hemicyanin styryl thiol fluorescent dye of formula (I) or (II) for which m and n are 1 comprises a thiol-function-protecting group Y, the process of the present disclosure may be preceded by a deprotection step aimed at restoring the SH function in situ.

By way of non-limiting example, it is possible to deprotect the S—Y function with a Y protecting group by adjusting the pH as follows:

| Y: Protecting group | Deprotection |
|---|---|
| alkylcarbonyl | pH > 9 |
| arylcarbonyl | pH > 9 |
| alkoxycarbonyl | pH > 9 |
| aryloxycarbonyl | pH > 9 |
| arylalkoxycarbonyl | pH > 9 |
| (di)(alkyl)aminocarbonyl | pH > 9 |
| (alkyl)arylaminocarbonyl | pH > 9 |
| optionally substituted aryl, such as phenyl | pH > 9 |
| 5-, 6- or 7-membered monocyclic heteroaryl, such as oxazolium | pH > 9 |
| 8- to 11-membered bicyclic heteroaryl, such as benzoimidazolium or benzoxazolium | pH > 9 |

The deprotection step can also be carried out during a hair pretreatment step, for instance reducing pretreatment of the hair.

According to at least one embodiment, the reducing agent is added to the dye composition containing at least one hemicyanin styryl fluorescent dye of formula (I) or (II) at the time of use.

According to at least one embodiment, the composition comprising at least one hemicyanin styryl fluorescent dye of formula (I) or (II) also contains at least one reducing agent as defined above. This composition is then applied to the hair.

According to at least one embodiment, the reducing agent is applied as a post-treatment, after the application of the composition containing at least one hemicyanin styryl fluorescent dye of formula (I) or (II). The duration of the post-treatment with the reducing agent may be short, for example from 1 second to 30 minutes, further for example 1 minute to 15 minutes, with a reducing agent as described above.

According to at least one embodiment, the reducing agent is an agent of thiol or borohydride type as described above.

At least one embodiment of the present disclosure relates to a process wherein the hemicyanin styryl fluorescent dye of formula (I) or (II) can be applied directly to the hair without reducing agents, free of reducing pretreatment or reducing post-treatment.

A treatment with an oxidizing agent may optionally be combined. For example, the process of dyeing according to the present disclosure comprises an additional step consisting in applying an oxidizing agent to the keratin fibers. Any type of oxidizing agent conventional in the field may be used, including hydrogen peroxide, urea peroxide, alkali metal bromates, persalts such as perborates and persulfates, and also enzymes, among which non-limiting mention may be made of peroxidases, 2-electron oxidoreductases such as uricases and 4-electron oxygenases such as laccases. In at least one embodiment, hydrogen peroxide is used. The duration of such a treatment is between 1 second and 40 minutes, for example between 15 seconds and 15 minutes.

The application of the dye composition according to the present disclosure may be carried out at ambient temperature. It may, however, be carried out at temperatures ranging from 20 to 180° C.

A subject of the present disclosure is also a multicompartment dyeing device or dyeing "kit" wherein a first compartment contains a dye composition comprising at least one hemicyanin styryl fluorescent dye of formula (I) or (II) and a second compartment contains a reducing agent capable of reducing the disulfide functions of keratin materials and/or of the hemicyanin styryl disulfide fluorescent dye of formula (I) or (II).

One of these compartments may also contain at least one other dye of direct dye or oxidation dye type.

The present disclosure also relates to a multicompartment device wherein a first compartment contains a dye composition comprising at least one hemicyanin styryl fluorescent dye of formula (I) or (II); a second compartment contains a reducing agent capable of reducing the disulfide bond of keratin materials and/or of the hemicyanin styryl disulfide fluorescent dye of formula (I) or (II); and a third compartment contains an oxidizing agent.

In one embodiment, the dyeing device contains a first compartment containing a dye composition which comprises at least one hemicyanin styryl protected thiol fluorescent dye of formula (I) or (II) where m and n are 1, a second compartment containing an agent capable of deprotecting the protected thiol so as to free the thiol, and optionally a third compartment comprising an oxidizing agent.

Each of the devices mentioned above may be equipped with a means for delivering the desired mixture to the hair, for example such as the devices disclosed in French Patent No. 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

EXAMPLES

Synthesis Examples

Example 1

Synthesis of 2,2'-{disulfanediylbis[ethane-2,1-diyl (methylimino)-4,1-phenyleneethene-2,1-diyl]}bis(3-ethyl-1,3-benzothiazol-3-ium) diiodide [1]

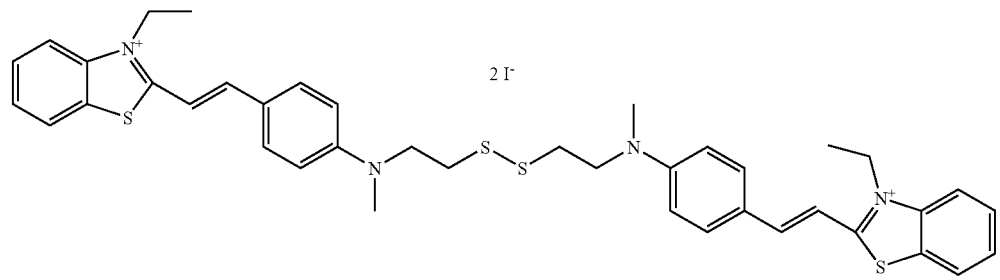

Synthesis Scheme:

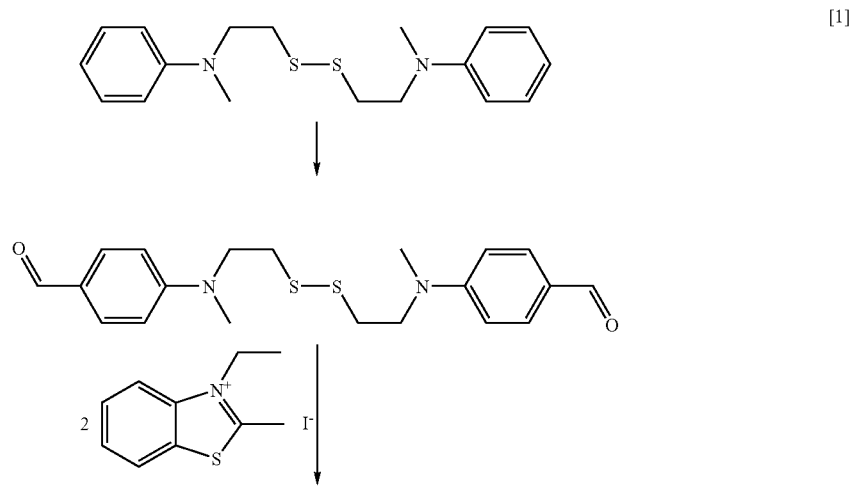

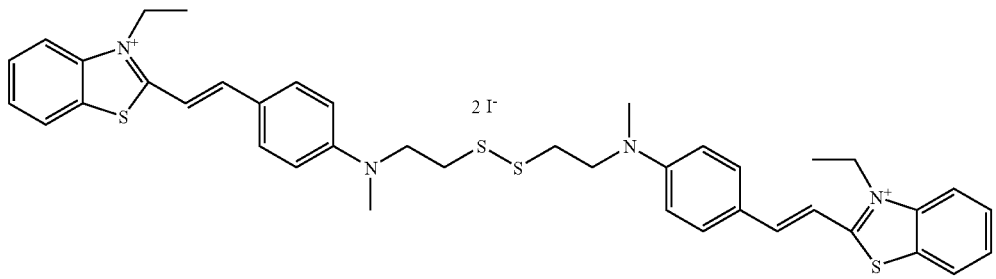

Procedure:

Stage 1: 4,4'-{disulfanediylbis[ethane-2,1-diyl(methylimino)]}dibenzaldehyde 82.3 g of phosphorus oxychloride were added to 500 ml of DMF at 0° C. After stirring for 30 min at 0° C., a solution of 47 g of N,N'-(disulfanediyldiethane-2,1-diyl)bis(N-methylaniline) was added dropwise. The mixture was stirred for 90 min at 0° C. and then for 75 min at 10° C. and 105 min at 40° C. It was then poured into 2.5 l of ice-cold water and 700 ml of 5N sodium hydroxide were added. The yellow precipitate obtained was filtered off over celite and solubilized in 200 ml of dichloromethane, and the solution obtained was washed with 200 ml of a saturated aqueous solution of sodium chloride. After drying over magnesium sulfate and evaporation of the dichloromethane, the yellow residue (80 g) was purified by silica gel chromatography. After drying, a light yellow powder was recovered. The analyses showed that the product was in conformity with the expected structure.

Stage 2: 2,2'-{disulfanediylbis[ethane-2,1-diyl(methylimino)-4,1-phenyleneethene-2,1-diyl]}bis(3-ethyl-1,3-benzothiazol-3-ium) diiodide [1]

1.9 g of N-ethylbenzothiazolium iodide in solution in 2 ml of dichloromethane were added to 1.2 g of 4,4'-{disulfanediylbis[ethane-2,1-diyl(methylimino)]}dibenzaldehyde in suspension in 9 ml of ethanol at 79° C. The mixture was refluxed for 72 h with stirring. After cooling, the violet suspension was filtered. After drying, 1.5 g of black powder were recovered. The analyses indicated that the product was in conformity with compound [1] and pure.

$^1$H NMR (400 MHz, MeOH-d$_4$)-1.42 (t, 6H), 3.04 (t, 4H), 3.13 (s, 6H), 3.82 (t, 4H), 4.84 (q, 4H), 6.90 (d, 4H), 7.64 (d, 2H), 7.68 (dd, 2H), 7.78 (dd, 2H), 7.95 (d, 4H), 8.08 (d, 2 H), 8.15 (d, 2H), 8.30 (d, 2H).

Example 2

Synthesis of 2-(2-{4-[[2-({2-[{4-[-2-(1,3-dimethyl-1H-benzimidazol-3-ium-2-yl)vinyl]phenyl}(methyl)amino]ethyl}disulfanyl)ethyl](methyl)amino]phenyl}vinyl)-1,3-dimethyl-1H-3,1-benzimidazol-3-ium) dimethyl sulfate [2]

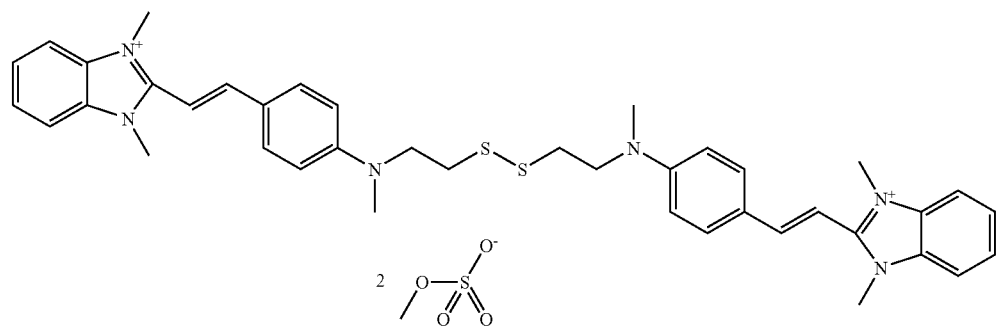

Synthesis Scheme:

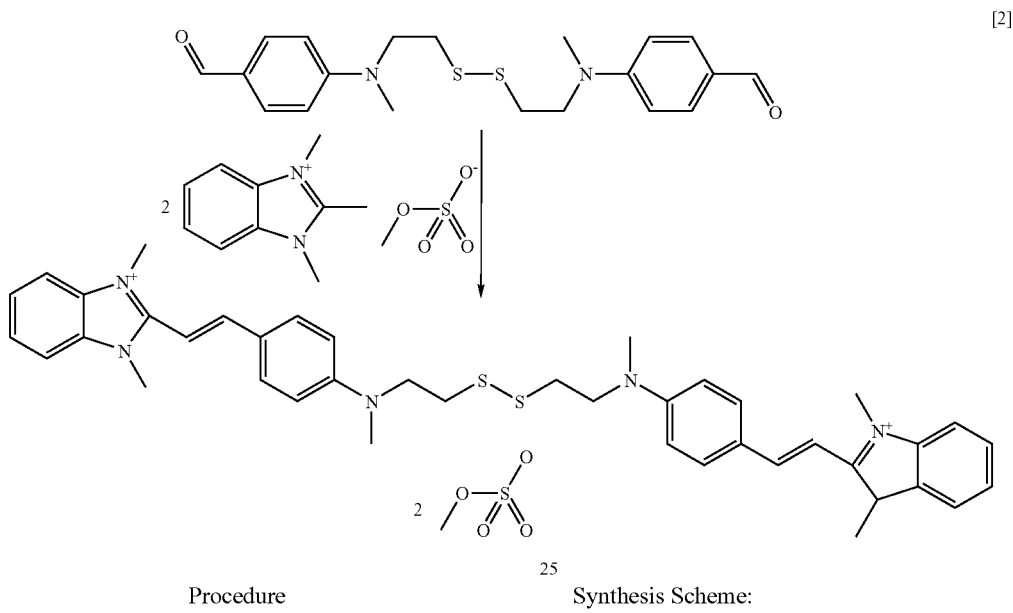

Procedure

Synthesis of 2-(-2-{4-[[2-({2-[{4-[2-(1,3-dimethyl-1H-benzimidazol-3-ium-2-yl)vinyl]phenyl}(methyl)amino]ethyl}disulfanyl)ethyl](methyl)amino]phenyl}vinyl)-1,3-dimethyl-1H-3,1-benzimidazol-3-ium) dimethyl sulfate [2]

0.5 g of 1,2,3-trimethyl-1H-benzimidazol-3-ium methyl sulfate in solution in 2 ml of dichloromethane was added to 0.36 g of 4,4'-{disulfanediylbis[ethane-2,1-diyl(methylimino)]}dibenzaldehyde in suspension in 8 ml of ethanol at 79° C. and 0.15 ml of pyrrolidine. The mixture was kept at 80° C. for 7 h with stirring. After cooling, the suspension was poured into 25 ml of cold ethyl acetate. The precipitate obtained was filtered off, washed with ethyl acetate and dried. 0.3 g of orange powder was recovered. The analyses indicated that the product was in conformity with compound [2].

Example 3

Synthesis of 3,3'-(disulfanediyldiethane-2,1-diyl)bis(6-chloro-2-{-2-[4-(dimethylamino)-1-naphthyl]vinyl}-1-methyl-1H-benzimidazol-3-ium) dibromide [3]

Synthesis Scheme:

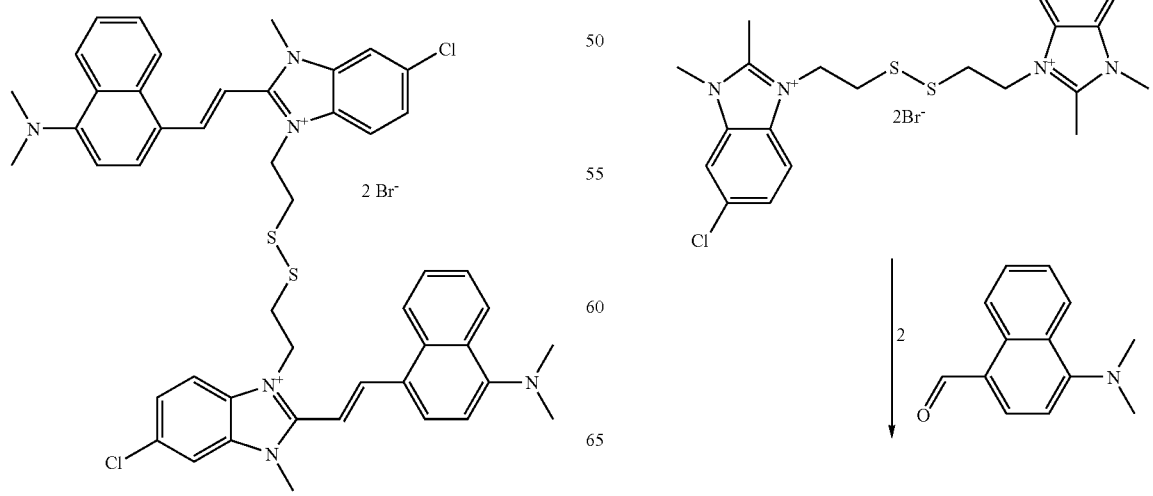

-continued

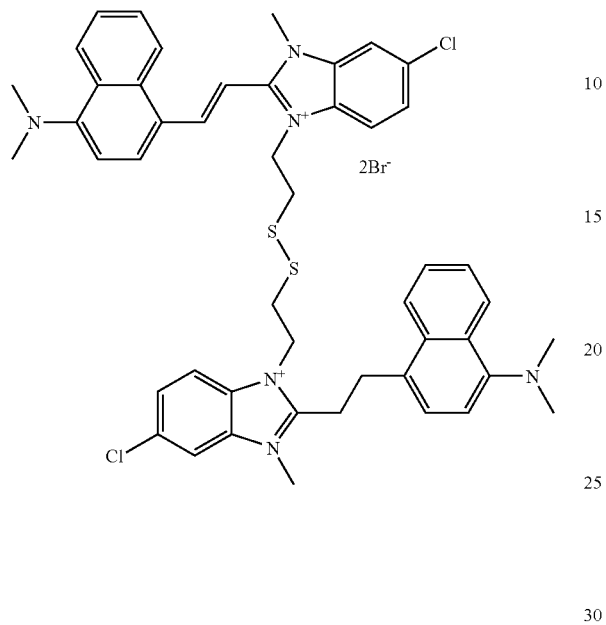

Procedure

Stage 1: Synthesis of 3,3'-(disulfanediyldiethane-2,1-diyl)bis(6-chloro-1,2-dimethyl-1H-benzimidazol-3-ium) dibromide 142 mg of chloro-1,2-dimethylbenzimidazole, 100 mg of bis(2-bromoethyl) disulfide, 54 mg of sodium iodide, and 0.4 ml of propionitrile were stirred at 100° C. for 17 h. After cooling, filtration and washing with 5 times 5 ml of acetonitrile, 125 mg of gray powder were recovered. The analyses showed that the product was in conformity with the expected structure.

Stage 2: Synthesis of 3,3'-(disulfanediyldiethane-2,1-diyl)bis(6-chloro-2-{-2-[4-(dimethylamino)-1-naphthyl]vinyl}-1-methyl-1H-benzimidazol-3-ium) dibromide 600 mg of 3,3'-(disulfanediyldiethane-2,1-diyl)bis(6-chloro-1,2-dimethyl-1H-benzimidazol-3-ium) dibromide, 370 mg of 4-dimethylaminonaphthaldehyde, 6 ml of methanol, and 42 µl of piperidine were stirred at ambient temperature for 24 h. The mixture obtained was poured dropwise into 200 ml of ethyl ether. After filtration and drying, 400 mg of orange solid were recovered. The analyses showed that the product was in conformity with the expected structure [3].

Example 4

Synthesis of 3,3'-(disulfanediyldiethane-2,1-diyl)bis(2-{-2-[4-(dimethylamino)phenyl]vinyl}-1-methyl-1H-benzimidazol-3-ium) dibromide [4]

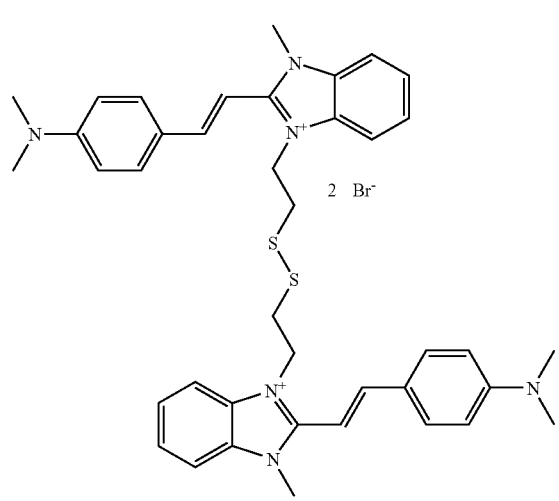

Synthesis Scheme:

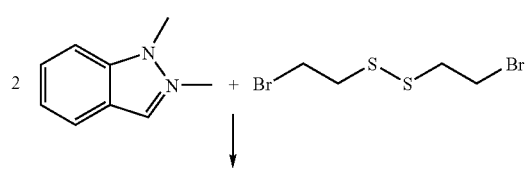

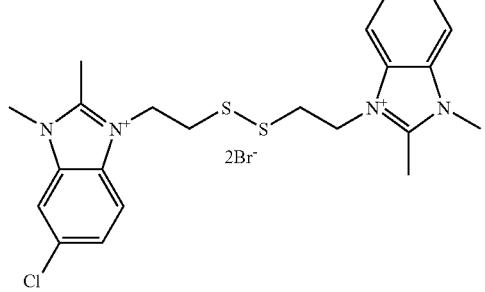

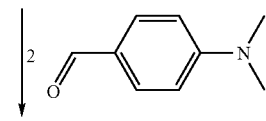

-continued

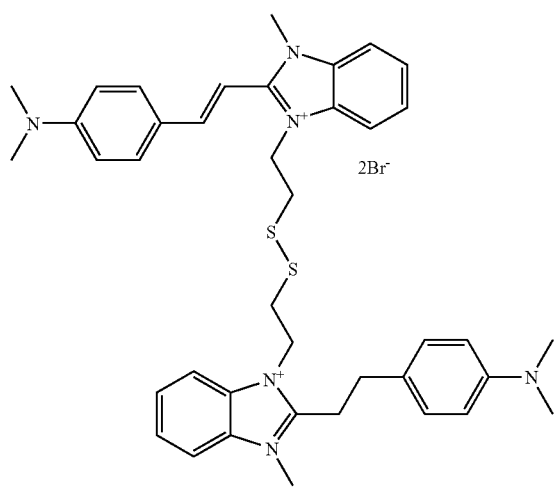

2Br⁻

Procedure

Stage 1: Synthesis of 3,3'-(disulfanediyldiethane-2,1-diyl)bis(1,2-dimethyl-1H-benzimidazol-3-ium) dibromide 2.4 g of 1,2-dimethylbenzimidazole, 2.1 g of bis(2-bromoethyl) disulfide and 6 ml of propionitrile were stirred at 100 C in a sealed 20 ml reactor for 8 h. After cooling, filtration, washing with 3 times 10 ml and drying under vacuum, 2.2 g of beige solid were recovered. The analyses showed that the product was in conformity with the expected structure.

Stage 2: Synthesis of 3,3'-(disulfanediyldiethane-2,1-diyl)bis(2-{-2-[4-(dimethylamino)phenyl]vinyl}-1-methyl-1H-benzimidazol-3-ium) dibromide 1.3 g of 3,3'-(disulfanediyldiethane-2,1-diyl)bis(1,2-dimethyl-1H-benzimidazol-3-ium) dibromide, 1 g of 4-dimethylaminobenzaldehyde, 26 ml of methanol, and 500 μl of piperidine were stirred at 60° C. for 1 h 30. 350 μl of piperidine were added and the stirring was maintained for 2 h 30. After cooling, the orange precipitate obtained was filtered off and washed with 3 times 5 ml of methanol at 4° C. The solid recovered was softened by kneading in hot ethanol, under ultrasound. The mixture was cooled, filtered and dried. 450 mg of orangey-red powder were obtained. The analyses showed that the product was pure and in conformity with the expected structure [4].

Example 5

Synthesis of 2,2'-{disulfanediylbis[ethane-2,1-diyl(methylimino)-4,1-phenyleneethene-2,1-diyl]}bis(3-ethyl-1,3-benzoxazol-3-ium) diiodide [5]

[5]

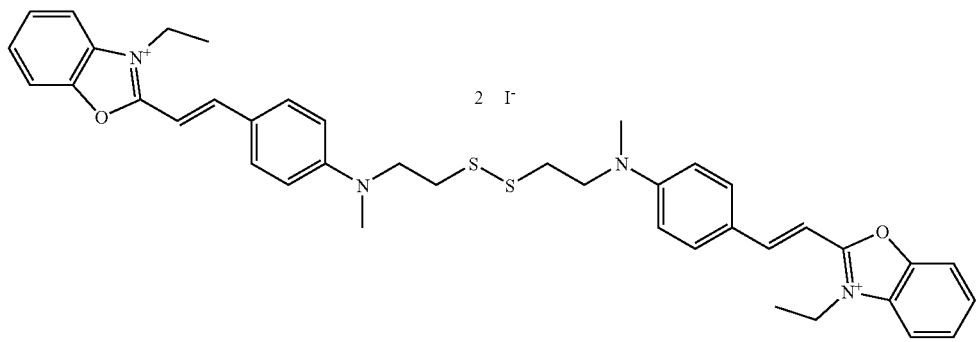

2 I⁻

Synthesis Scheme:

[5]

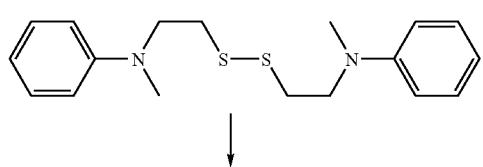

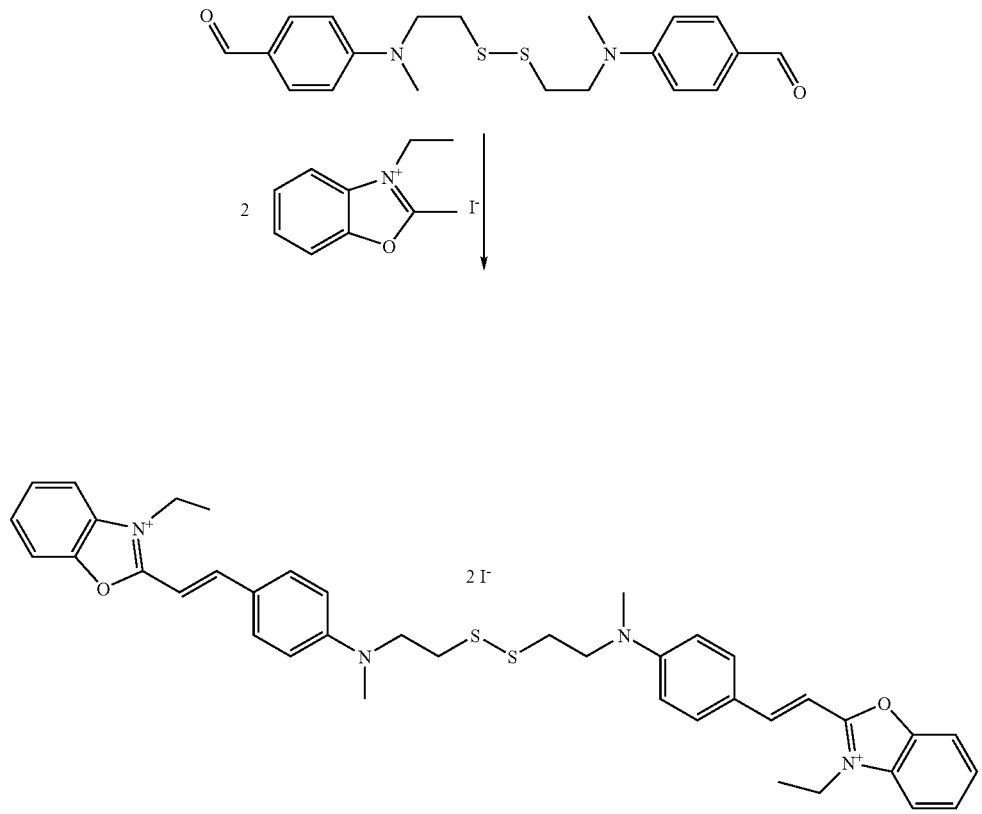

Procedure 6.56 g of 3-ethyl-2-methyl-1,3-benzoxazol-3-ium iodide in solution in 12 ml of a 60:40 isopropanol/N-methylpyrrolidinone mixture were added to 4.16 g of 4,4'-{disulfanediylbis[ethane-2,1-diyl(methylimino)]}dibenzaldehyde dispersed in 8 ml of a 60:40 isopropanol/N-methylpyrrolidinone mixture. The mixture was stirred at 80° C. for 27 h. After cooling, the solution is poured into 200 ml of ethyl acetate. The precipitate was filtered off, washed with three times 150 ml of ethyl acetate and dried. 6.83 g of red powder were recovered. The analyses showed that the product was in conformity with the expected structure [5].

Example 6

Synthesis of 2,2'-{disulfanediylbis[ethane-2,1-diyl (methylimino)-4,1-phenylene ethene-2,1-diyl]}bis(3-methyl-1,3-thiazol-3-ium) dimethyl sulfate [6]

[6]

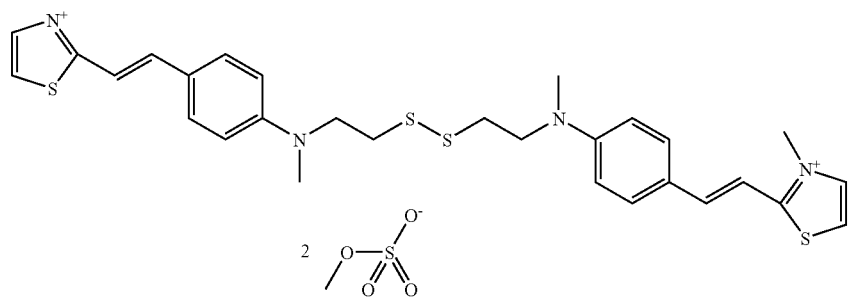

Synthesis Scheme:

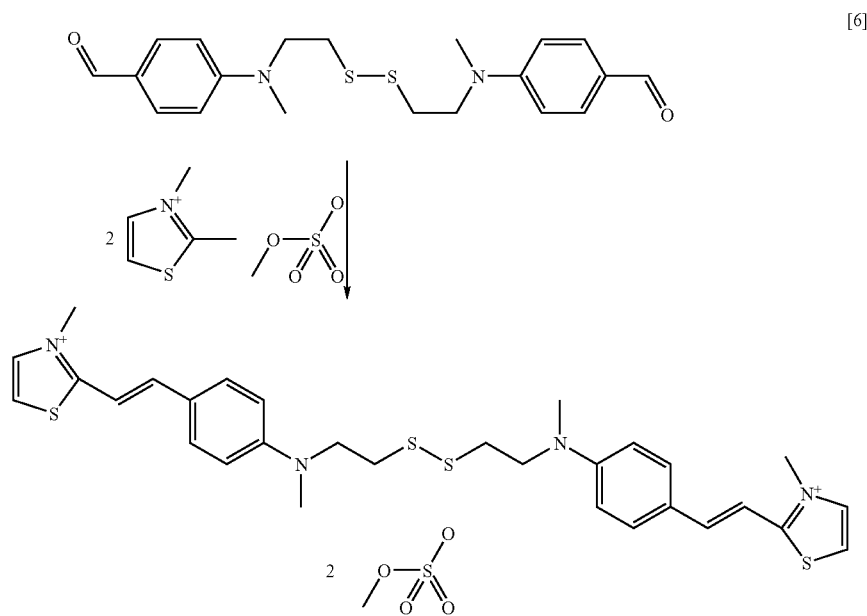

Procedure

Synthesis of 2,2'-{disulfanediylbis[ethane-2,1-diyl(methylimino)-4,1-phenylene ethene-2,1-diyl]}bis(3-methyl-1,3-thiazol-3-ium) dimethyl sulfate [6]

1.66 g of 2,3-dimethylthiazolium methyl sulfate in solution in 2 ml of a 60:40 isopropanol/N-methylpyrrolidinone mixture were added to 1.43 g of 4,4'-{disulfanediylbis[ethane-2,1-diyl(methylimino)]}dibenzaldehyde in suspension in 5 ml of a 60:40 isopropanol/N-methylpyrrolidinone mixture and 0.56 ml of pyrrolidine. The mixture was kept at 50° C. for 7 h with stirring, under argon in the dark. After cooling, the suspension was poured into 25 ml of cold ethyl acetate. The precipitate obtained was filtered off, washed with ethyl acetate and dried.

Example 7

Synthesis of 2-[2-(4-{[2-(acetylsulfanyl)-ethyl](methyl)amino}phenyl)ethenyl]-1,3-dimethyl-1H-benzimidazol-3-ium mesylate Synhesis Scheme:

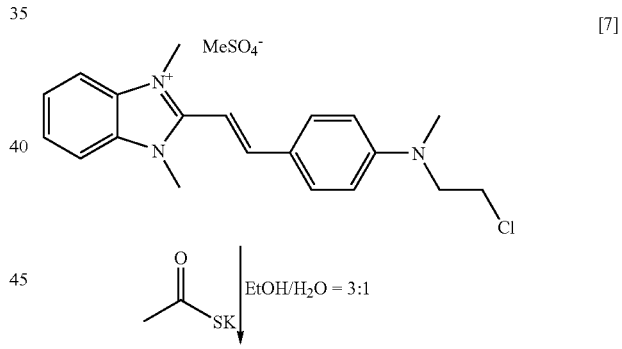

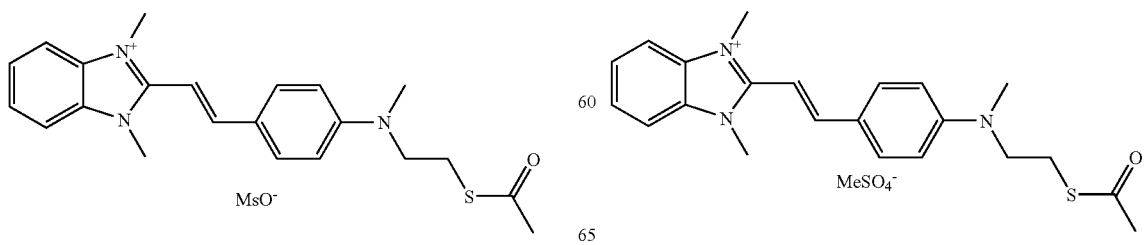

Procedure:

A mixture of 2-[2-{4-[(2-chloroethyl)(methyl)-amino]phenyl}-ethenyl]-1,3-dimethyl-1H-benzimidazol-3-ium mesylate (1.6 g, 3.5 mmol) and potassium thioacetate (0.6 g, 5.3 mmol) in 12 ml of ethanol and 4 ml of water was heated under reflux for 12 h. After cooling, the solvents were removed under vacuum. The resulting residue was subjected to chromatography on alumina eluting with a mixture of dichloromethane and methanol (500:3) to afford 0.8 g of crude product. Further purification was carried out by recrystallization from 2-propanol and ethyl acetate mixture solvents to give 0.7 g of an orange powder. Analyses were in accordance with the expected structure [7] and indicated a 69:31 E/Z ratio Example 8

Synthesis of S-{2-[{4-[2-(1,3-dimethyl-1H-benzimidazol-3-ium-2-yl)ethenyl]phenyl}(methyl)amino]-ethyl}thiosulfate [8]

Synthesis Scheme:

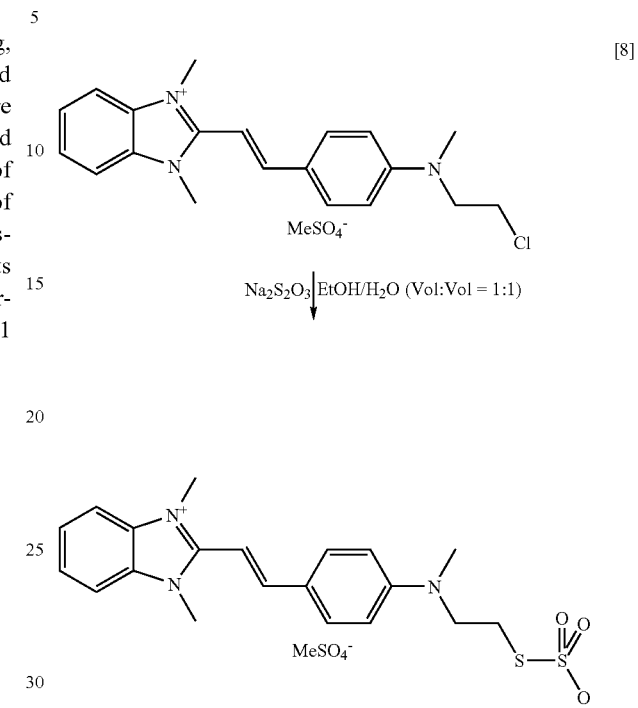

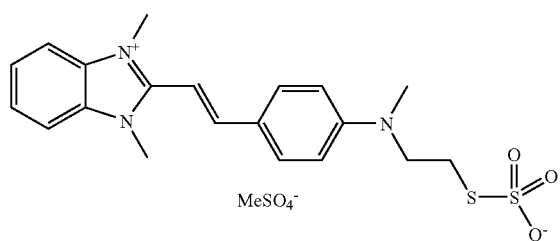

Procedure:

To a stirring solution of 2-[2-{4-[(2-chloroethyl)(methyl)-amino]phenyl}-ethenyl]-1,3-dimethyl-1H-benzimidazol-3-ium mesylate (1.0 g, 2.2 mmol) in 10 ml of ethanol and 10 ml of water, 1.4 g (8.9 mmol) of sodium thiosulfate was added. The mixture was heated under reflux for 48 h. The resulting solids were collected by filtration and washed with water three times and then ethanol twice. The drying afforded 0.8 g of yellow-orange powder. Analyses were in accordance with the expected structure of compound [8]

Example 9

Synthesis of 1,1'-{disulfanediylbis[ethane-2,1-diylimino(2-oxoethane-2,1-diyl)]}bis{2-[2-{4-[bis(2-hydroxyethyl)amino]phenyl}ethenyl]-3-methyl-1H-benzimidazol-3-ium}chloride [9]

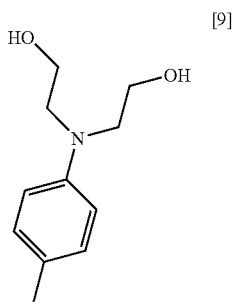

-continued
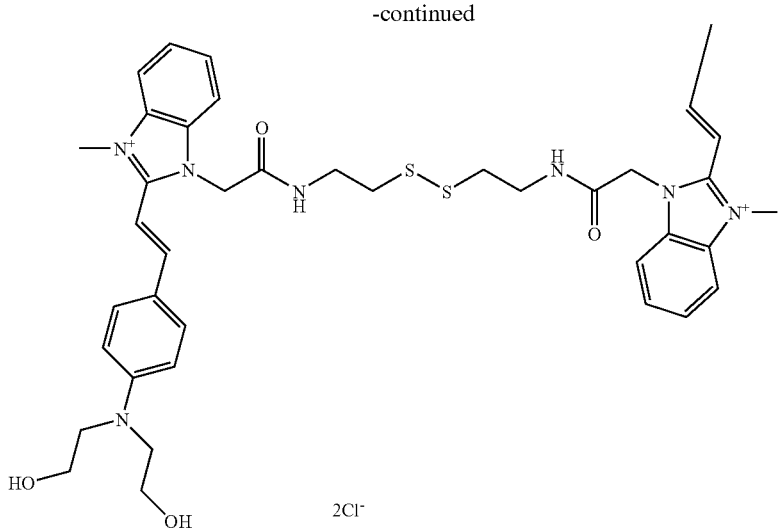
Reaction Scheme
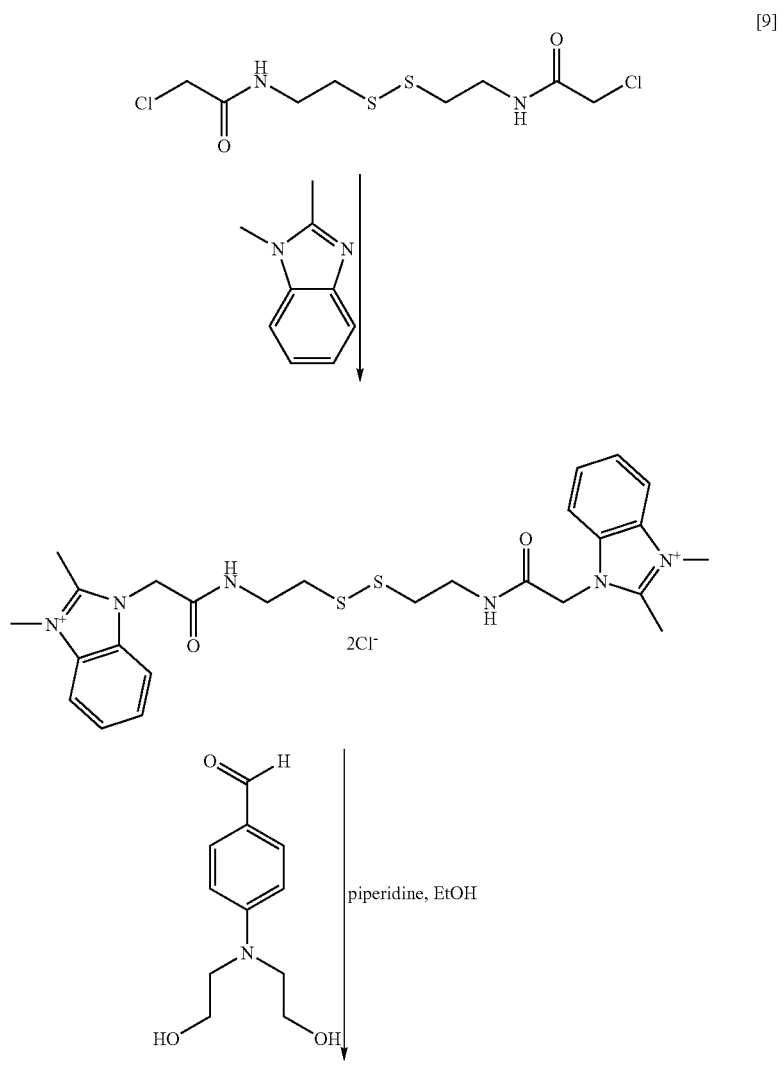

-continued

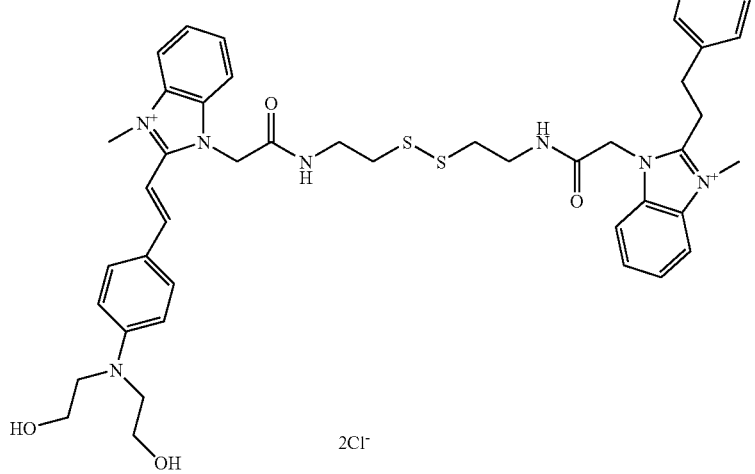

Step 1: synthesis of 1,1'-{disulfanediylbis[ethane-2,1-diylimino(2-oxoethane-2,1-diyl)]}bis(2,3-dimethyl-1H-benzimidazol-3-ium) chloride A mixture of compound 1,2-dimethyl-1H-benzimidazole (2.93 g, 20 mmol) and N,N'-(disulfanediyldiethane-2,1-diyl)bis(2-chloroacetamide) (1.53 g, 5 mmol) in 20 ml of acetonitrile was heated to reflux for 24 h. After cooling, the resulting white solids were collected by filtration and washed with ethyl acetate and dichloromethane to afford 1.94 g of a white powder. Analyses were in accordance with the expected structure.

Step 2: Synthesis of 1,1'-{disulfanediylbis[ethane-2,1-diylimino(2-oxoethane-2,1-diyl)]}bis{2-[2-{4-[bis(2-hydroxyethyl)amino]phenyl}ethenyl]-3-methyl-1H-benzimidazol-3-ium}chloride [9]

To a stirring solution of 4-[bis(2-hydroxyethyl)-amino]benzaldehyde (1.7 g, 8.1 mmol) and 1,1'-{disulfanediylbis[ethane-2,1-diylimino(2-oxoethane-2,1-diyl)]}bis(2,3-dimethyl-1H-benzimidazol-3-ium) chloride (1.2 g, 2 mmol) in 35 ml of ethanol, 0.5 ml of piperidine was added as a catalyst. The reaction mixture was heated to reflux for 7 h. After cooling, the resulting orange solids were collected by filtration and then washed with dichloromethane and methanol. The drying afforded 1.6 g of a orange solid. Analyses were in accordance with the expected structure.

Example 10

Synthesis of 1,1'-{disulfanediylbis[ethane-2,1-diylimino(2-oxoethane-2,1-diyl)]}bis{3-methyl-2-[2-(2,3,6,7-tetrahydro-1H,5H-pyrido[3,2,1-ij]quinolin-9-yl)ethenyl]-1H-benzimidazol-3-ium}chloride [10]

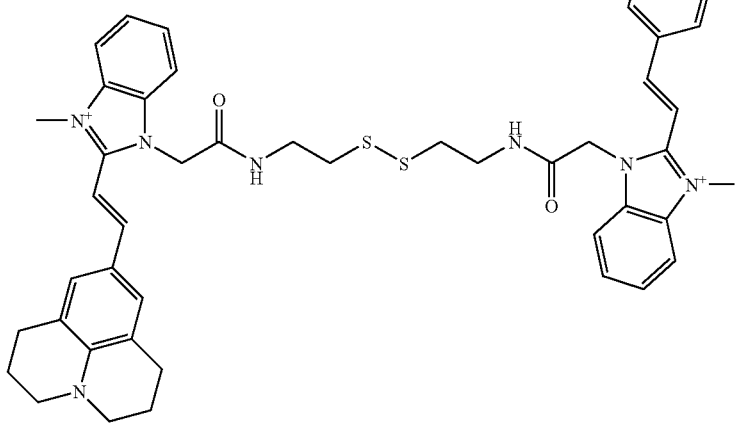

Reaction Scheme

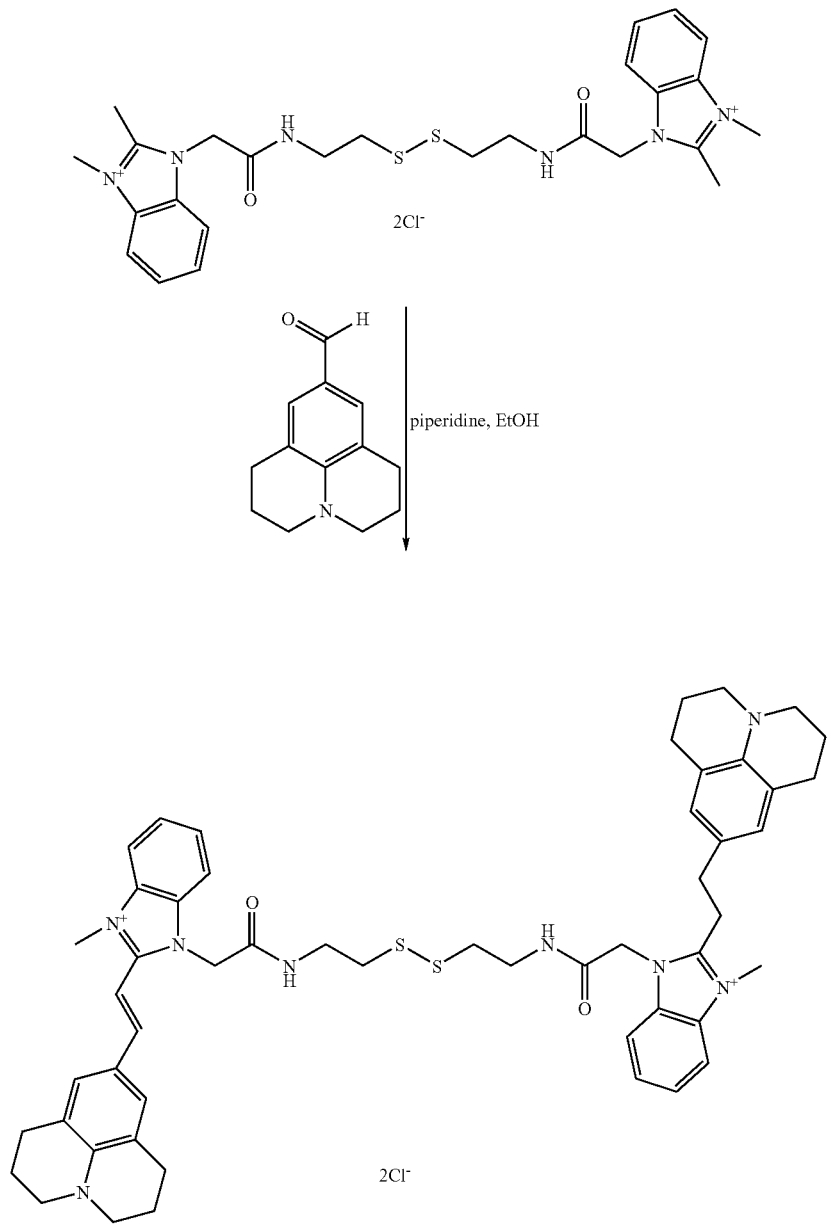

To a stirring solution of 2,3,6,7-tetrahydro-1H,5H-pyrido[3,2,1-ij]quinoline-9-carbaldehyde (julolidine carboxaldehyde, 12.01 10 mmol) and 1,1'-{disulfane-diylbis[ethane-2,1-diylimino(2-oxoethane-2,1-diyl)]}bis(2,3-dimethyl-1H-benzimidazol-3-ium) chloride (1.49 g, 2.5 mmol) in 15 ml of acetonitrile ethanol, 0.2 ml of piperidine was added as a catalyst. The reaction mixture was heated to reflux for 24 h. After cooling, the resulting solids were collected by filtration and then washed with acetonitrile three times to afford 1.45 of a red solid. Analyses (1H NMR, 13C NMR and MS) were in accordance with the expected structure [10].

DYEING EXAMPLES

Example 1

Dyeing Process—Compounds [1], [2] and [4]

Preparation of a Composition A

| | |
|---|---|
| Disulfide dye of [1][2] or [4] | $5 \times 10^{-4}$ mol % |
| Benzyl alcohol | 4 g |
| Polyethylene glycol 6 EO | 6 g |
| Hydroxyethylcellulose | 0.7 g |
| Alkylpolyglucoside in an aqueous solution containing 65% AM | 4.5 g |
| Demineralized water | qs 100 g |

Preparation of a Composition B

| | | |
|---|---|---|
| Thioglycolic acid | 1M | |
| Sodium hydroxide | qs pH 8.5 | |
| Demineralized water | qs 100 g | |

At the time of use, compositions A (22.5 ml) and B (2.5 ml) are mixed, then the mixture obtained is applied to two locks of 1 g of natural white hair (NW), two locks of 1 g of permanent-waved hair (PW) and one lock of 1 g of dark hair (tone height 4) for 20 minutes at ambient temperature (the locks are turned over and reimpregnated after 10 minutes).

After rinsing with running water, shampooing, and further rinsing followed by drying, lightening of the dark hair thus treated was observed: the lock of tone height 4 had become visually lighter than untreated control locks. The locks of white hair were colored with strong shades.

Visual Observations:

During the rinsing and shampooing of the examples [1], [2] and [4] there was no visible bleeding of the color; the shampoo foam and the rinsing water were virtually uncolored.

The color observed was conserved, and the lightening effect remained visible on the shampooed hair.

Reflectance Results:

The lightening effectiveness of the compositions in accordance with the present disclosure was expressed as a function of the reflectance of the hair. These reflectances are compared with the reflectance of a lock of untreated hair of tone height TH4.

The reflectance was measured by means of a KONIKA-MINOLTA®, CM 3600d spectrophotocolorimeter apparatus and after irradiation of the hair with visible light in the wavelength range of from 400 to 700 nanometers.

Figure 2:
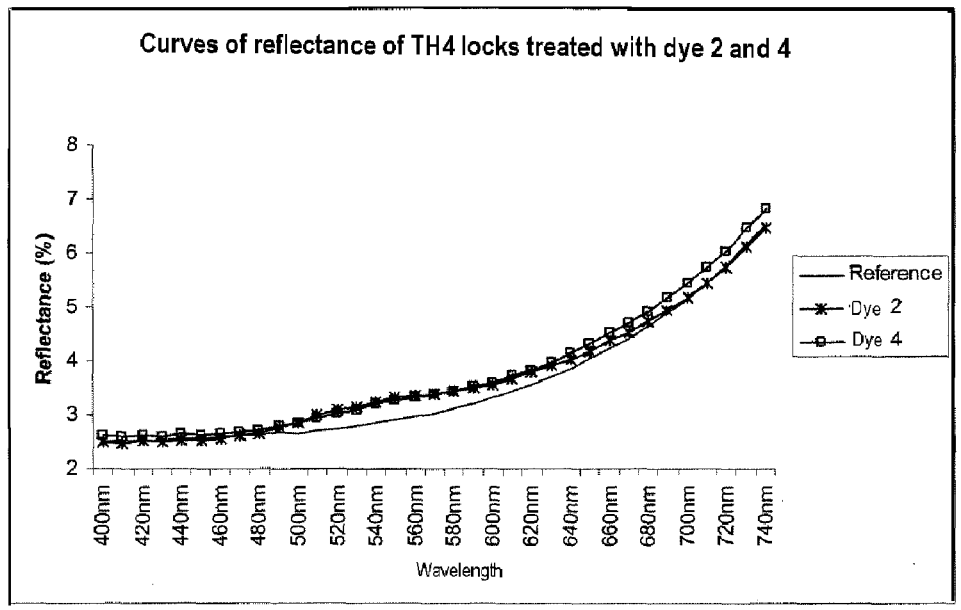
FIG. 2 shows the reflectance values of a reference lock (a lock of untreated hair of tone height TH4) and the reflectance values of TH4 locks treated with dyes [2] and [4].

The reflectance of a lock of hair treated with a composition according to the present disclosure was greater than that of untreated hair. For example, as shown in FIG. 1, the reflectance of the locks treated with dye [1] was much greater than that of the reference lock in the wavelength range above 560 nm. As shown in FIG. 2, for dyes [2] and [4], the reflectance was greater over a wider wavelength range, from 500 nm onward. The locks treated with these three compounds therefore appeared to be lighter.

Results in the L*a*b* System:

The color of the locks was evaluated in the L*a*b* system by means of a MINOLTA® CM 3600D spectrocolorimeter (Illuminant D65). In this L*a*b* system, L* is the lightness, a* indicates the green/red color axis and b* the blue/yellow color axis. The higher the value of L*, the lighter or weaker the color. Conversely, the lower the value of L*, the darker or much stronger the color. The higher the value of a*, the redder the shade, and the higher the value of b*, the more yellow the shade.

The variation in coloring between the TH4 dyed and washed locks of hair is measured by (ΔE) according to the following equation:

$$\Delta E = \sqrt{(L^* - L_o^*)^2 + (a^* - a_o^*)^2 + (b^* - b_o^*)^2}$$

In this equation, L*, a* and b* are the values measured after dyeing, and $L_o^*$, $a_o^*$ and $b_o^*$ are the values measured before dyeing (or shampooing).

The greater the value of ΔE, the greater the difference in color between the TH4 locks and the colored locks.

| Compound | L* (D65) | a* (D65) | b* (D65) | dE* ab (D65) |
|---|---|---|---|---|
| TH4 Reference | 20 | 2.69 | 3.02 | — |
| Compound 1 | 20.48 | 5.63 | 3.21 | 2.98 |
| Compound 2 | 21.14 | 1.6 | 4.96 | 2.49 |
| Reference | 60.45 | 1.49 | 16.08 | — |
| Compound 1 | 39.51 | 41.71 | 6.64 | 46.32 |
| Compound 2 | 60.53 | 7.75 | 65.3 | 49.62 |
| Compound 4 | 59.29 | 7.43 | 54.55 | 38.95 |

The values reported in the tables above show the observable effect of the coloring obtained even on dark hair (TH4) and a very strong coloring on white hair.

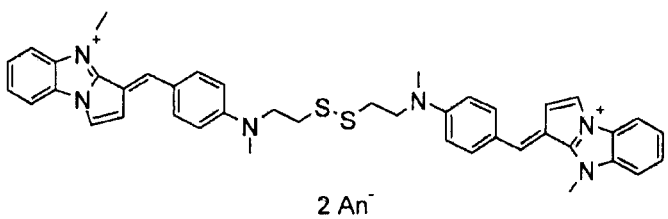

What is claimed is:
1. A fluorescent dye of formula (I) or (II):

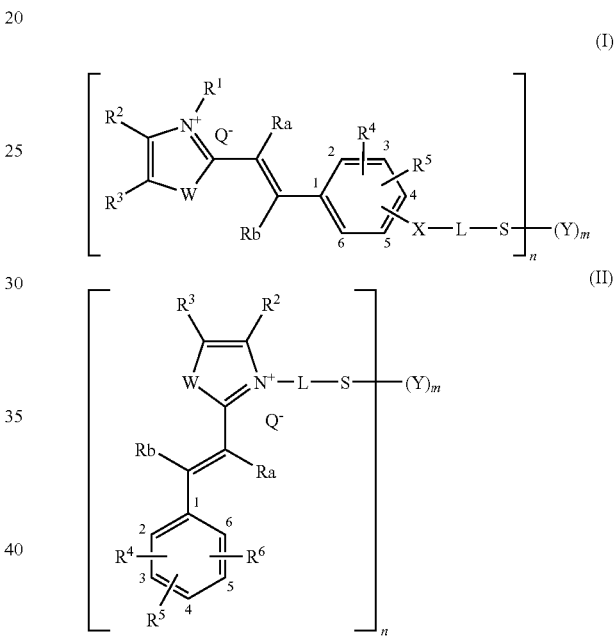

the organic or mineral acid salts thereof, optical isomers and geometric isomers thereof, and the solvates thereof:
wherein in formulae (I) and (II):
n is an integer ranging from 1 to 2;
m is an integer ranging from 0 to 1;
Ra and Rb, which may be identical or different, are chosen from a hydrogen atom and a $C_1$-$C_4$ alkyl group;
$R^1$ is chosen from a hydrogen atom and a ($C_1$-$C_6$)alkyl group, optionally substituted with a group chosen from halogen, $C_1$-$C_4$ alkoxy, $C_1$-$C_4$ (di)(alkyl)amino, phenyl, tolyl, and methoxyphenyl;
or else $R^1$ and Ra together form a ($C_3$-$C_6$)alkylene chain or a ($C_3$-$C_7$)alkenylene;
$R^2$ and $R^3$, which may be identical or different, are chosen from a hydrogen atom and a halogen atom, an optionally substituted ($C_1$-$C_6$)alkyl group, a ($C_1$-$C_6$) alkoxy group, or a ($C_1$-$C_6$)alkylthio group; or else $R^2$ and $R^3$ form, together with the carbon atoms which bear them, an optionally substituted benzo ring;
$R^4$, $R^5$ and $R^6$, which may be identical or different, are chosen from:

a hydrogen atom;

a $C_1$-$C_6$ alkyl radical optionally substituted with at least one radical chosen from the radicals hydroxyl, $C_1$-$C_2$ alkoxy, $C_2$-$C_4$ (poly)hydroxyalkoxy, acylamino, and amino substituted with two $C_1$-$C_4$ alkyl radicals, which may be identical or different;

a halogen atom such as chlorine, fluorine or bromine;

a hydroxyl group;

a $C_1$-$C_2$ alkoxy radical;

a $C_1$-$C_2$ alkylthio radical;

an amino radical;

a 5- or 6-membered heterocycloalkyl radical which may be substituted with 1 to 3 groups, which may be identical or different, chosen from hydroxyl, amino, (di)alkylamino, and $C_1$-$C_4$ hydroxyalkyl;

an amino radical substituted with one or two $C_1$-$C_6$ alkyl radicals, which may be identical or different, optionally bearing at least:
 i) a hydroxyl group,
 ii) an amino group optionally substituted with one or two $C_1$-$C_3$ alkyl radicals, it being possible for said alkyl radicals to form, with the nitrogen atom to which they are attached, a saturated or unsaturated, optionally substituted heterocycle comprising from 5 to 7 members, optionally comprising at least one other heteroatom which may or may not be different from nitrogen,
 —N(R)—C(O)—R' wherein the R radical is chosen from a hydrogen atom and a $C_1$-$C_4$ alkyl radical optionally bearing at least one hydroxyl group, and the R' radical is a $C_1$-$C_2$ alkyl radical;

a carboxylic radical in acid or salified form;

a polyhaloalkyl group comprising from 1 to 6 carbon atoms and from 1 to 6 halogen atoms, which may be identical or different;

or else two contiguous radicals $R^4$ with $R^5$ and/or $R^5$ with $R^6$ form, together with the carbon atoms which bear them, a benzo ring or a heterocycle, optionally substituted, fused to the phenyl group;

or else $R^4$, $R^5$ and $R^6$ form, together with the phenyl group of formula (II), a tricyclic unit of julolidine type:

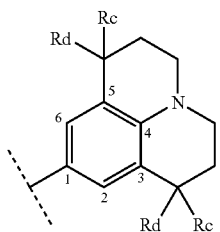

wherein Rc and Rd are chosen from a hydrogen atom and a $C_1$-$C_4$ alkyl group;

L is a $C_1$-$C_{20}$ divalent hydrocarbon-based chain, which is optionally substituted, optionally interrupted and/or optionally terminated at one or the other of its ends i) with at least one divalent group or combinations thereof chosen from: —N(R)—; —N$^+$(R)(R$^o$)—, An$^-$, —O—, —S—, —CO—, and —SO$_2$— with R and R$^o$, which may be identical or different, chosen from a hydrogen, and a $C_1$-$C_4$ alkyl, hydroxyalkyl or aminoalkyl radical, and An$^-$ is an anionic counterion, or ii) with a cationic heterocycle or cationic heteroaryl Het$^+$, An$^-$, wherein An$^-$ is defined as above and Het$^+$ is a saturated or unsaturated heterocycle comprising from 5 to 10 members, or a heteroaryl comprising from 5 to 10 members;

X is chosen from an oxygen atom, sulfur atom and an NR group wherein R is chosen from a hydrogen atom and a ($C_1$-$C_6$)alkyl group;

Y is chosen from: i) a hydrogen atom; ii) an alkali metal; iii) an alkaline earth metal; iv) an ammonium group: N$^+$R$^\alpha$R$^\beta$R$^\gamma$R$^\delta$, An$^{\prime\prime-}$ or a phosphonium group: P$^+$R$^\alpha$R$^\beta$R$^\gamma$R$^\delta$, An$^{\prime\prime-}$ with R$^\alpha$, R$^\beta$, R$^\gamma$ and R$^\delta$, which may be identical or different, chosen from a hydrogen atom and a ($C_1$-$C_4$)alkyl group and An$^{\prime\prime-}$ is an anionic counterion; or v) a thiol-function-protecting group;

W is chosen from an oxygen atom, sulfur atom, and an NR' group wherein R' is chosen from a hydrogen atom and a ($C_1$-$C_4$)alkyl group;

Q$^-$ is an anionic counterion;

it being understood that, when n is 2, then m is zero, and when n is 1, then m is 1.

2. The fluorescent dye according to claim 1, wherein m and n are 1 and Y is chosen from a hydrogen atom and an alkali metal.

3. The fluorescent dye of formula (I) or (II) as claimed in claim 1, wherein Y is a protecting group.

4. The fluorescent dye according to claim 1, wherein Y is a protecting group chosen from the following radicals:
 ($C_1$-$C_4$)alkylcarbonyl;
 ($C_1$-$C_4$)alkylthiocarbonyl;
 ($C_1$-$C_4$)alkoxycarbonyl;
 ($C_1$-$C_4$)alkoxythiocarbonyl;
 ($C_1$-$C_4$)alkylthiothiocarbonyl;
 (di)($C_1$-$C_4$)(alkyl)aminocarbonyl;
 (di)($C_1$-$C_4$)(alkyl)aminothiocarbonyl;
 arylcarbonyl;
 aryloxycarbonyl;
 aryl($C_1$-$C_4$)alkoxycarbonyl;
 (di)($C_1$-$C_4$)(alkyl)aminocarbonyl;
 ($C_1$-$C_4$)(alkyl)arylaminocarbonyl;
 carboxyl;
 SO$_3^-$; M$^+$ wherein M$^+$ is an alkali metal or else An$^-$ or An'$^-$ of formula (I) or (II) and M$^+$ are absent;
 optionally substituted aryl;
 optionally substituted heteroaryl;
 optionally cationic, optionally substituted heterocycloalkyl,
 the following group:

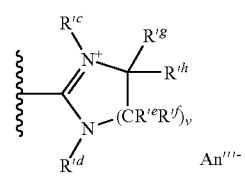

wherein R'$^c$, R'$^d$, R'$^e$, R'$^f$, R'$^g$ and R'$^h$, which may be identical or different, are chosen from a hydrogen atom and a ($C_1$-$C_4$) alkyl group, or else two groups R'$^g$ with R'$^h$, and/or R'$^e$ with R'$^f$ form an oxo or thioxo group, or else R'$^g$ with R'$^e$ together form a cycloalkyl; and v is an integer ranging from 1 to 3; and An$^{\prime\prime\prime-}$ is an anionic counterion;

isothiouronium —C(NR'$^c$R'$^d$)=N$^+$R'$^e$R'$^f$; An$^{\prime\prime\prime-}$ wherein R'$^c$, R'$^d$, R'$^e$ and R'$^f$, which may be identical or different, are chosen from a hydrogen atom and a $(C_1-C_4)$alkyl group and $An'''^-$ is defined as above;

isothiourea —$C(NR'^cR'^d)$=$NR'^e$; $An'^-$ wherein $R'^c$, $R'^d$, and $R'^e$ are defined as above;

optionally substituted (di)aryl$(C_1-C_4)$alkyl;

optionally substituted (di)heteroaryl$(C_1-C_4)$alkyl;

—$CR^1R^2R^3$ wherein $R^1$, $R^2$ and $R^3$, which may be identical or different, are chosen from a halogen atom and a group chosen from:

$(C_1-C_4)$alkyl;
$(C_1-C_4)$alkoxy;
optionally substituted aryl;
optionally substituted heteroaryl;
$P(Z^1)R'^1R'^2R'^3$ wherein $R'^1$ and $R'^2$, which may be identical or different, are chosen from a hydroxyl, a $(C_1-C_4)$alkoxy and an alkyl group, $R'^3$ is chosen from a hydroxyl and a $(C_1-C_4)$alkoxy group, and $Z^1$ is chosen from an oxygen atom and a sulfur atom;
a sterically hindered cyclic group; and
optionally substituted alkoxyalkyl.

5. The fluorescent dye according to claim 1, wherein Y is chosen from an alkali metal and a protecting group chosen from:

$(C_1-C_4)$alkylcarbonyl;
arylcarbonyl;
$(C_1-C_4)$alkoxycarbonyl;
aryloxycarbonyl;
aryl$(C_1-C_4)$alkoxycarbonyl;
(di)$(C_1-C_4)$(alkyl)aminocarbonyl;
$(C_1-C_4)$(alkyl)arylaminocarbonyl;
optionally aryl;
5- or 6-membered cationic monocyclic heteroaryl optionally substituted with at least one $(C_1-C_4)$alkyl group which may be identical or different;
8- to 11-membered cationic bicyclic heteroaryl optionally substituted with at least one $(C_1-C_4)$alkyl group which may be identical or different;
cationic heterocycle of the following formula:

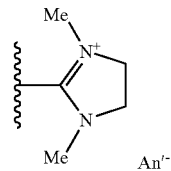

wherein $An'^-$ an anionic counterion
isothiouronium —$C(NH_2)$=$N^+H_2$; $An'''$; wherein $An'''^-$ is an anionic counterion,
isothiourea —$C(NH_2)$=NH; and
$SO_3^-$; $M^+$ wherein $M^+$ is an alkali metal or else $An^-$ or $An'^-$ of formula (I) or (II) and $M^+$ are absent.

6. The fluorescent dye according to claim 1, wherein n is 2 and m is 0.

7. The fluorescent dye according to claim 1, of formula $(I_a)$, $(II_a)$, $(I_b)$ and $(II_b)$:

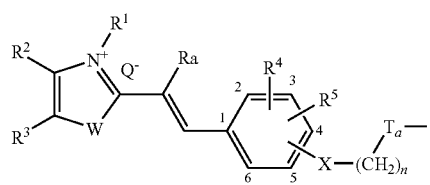 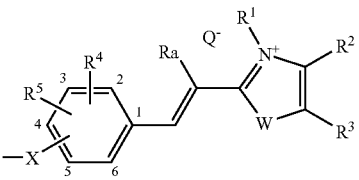

(I$_a$)

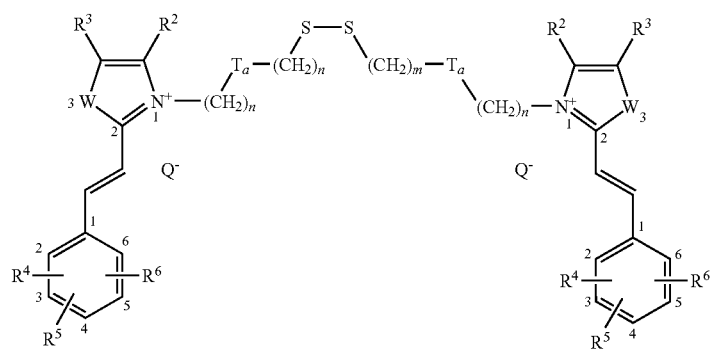

(II$_a$)

-continued

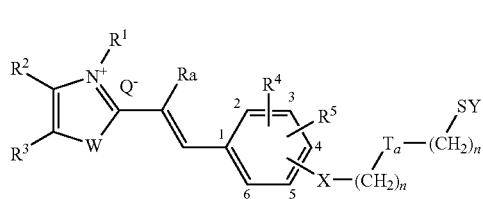
(I_b)

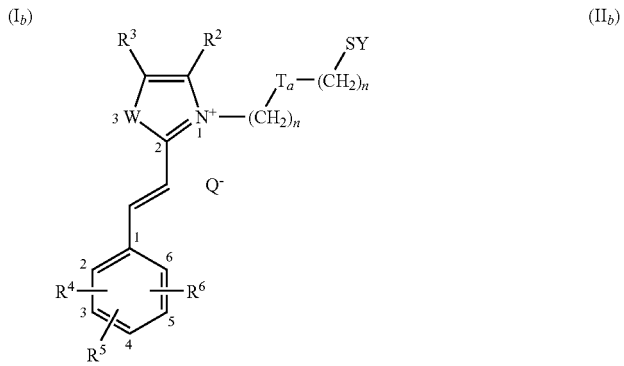
(II_b)

wherein:
  Ra, $R^1$ to $R^6$, B, Y and $Q^-$ are defined as in claim 1;
  n and m, which may be identical or different, are an integer ranging from 1 to 6, wherein the sum of n+m is an integer ranging from 2 to 4;
  X is a radical chosen from: -G-, -G'-C(G)-, and —C(G)-G'-, wherein G and G', which may be identical or different, are chosen from an oxygen atom, a sulfur atom, and NR, wherein R is chosen from a hydrogen atom and a $(C_1-C_6)$alkyl group;

$T_a$ is chosen from a σ covalent bond, a group —N(R'$_a$)—; —N$^+$(R'$_a$)(R'$_b$)—, An$^-$; —C(O)—N(R'$_a$)— or —N(R'$_a$)—C(O)—, and a divalent cationic heteroaryl comprising from 5 to 7 members, wherein R'$_a$, R'$_b$, which may be identical or different, are chosen from a hydrogen atom and a $(C_1-C_4)$alkyl radical, An$^-$ is an anionic counterion.

8. The fluorescent dye according to claim 1, chosen from the following dyes:

1

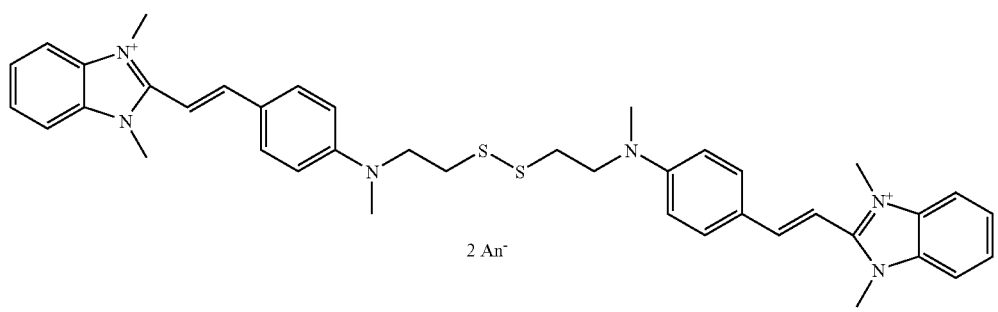

2

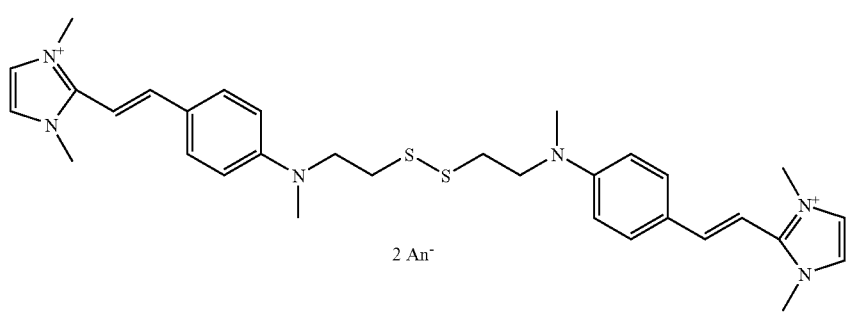

-continued
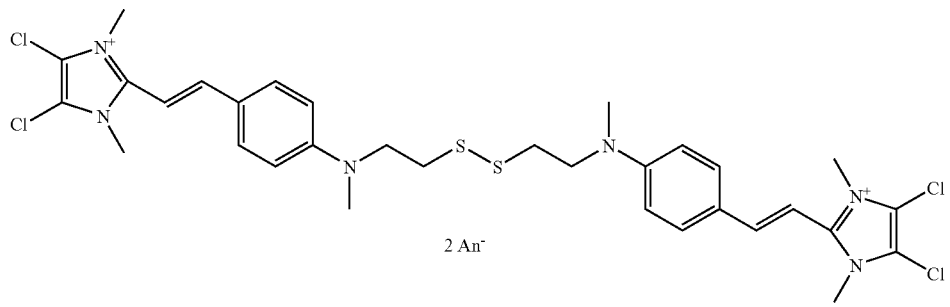
2 An⁻
3
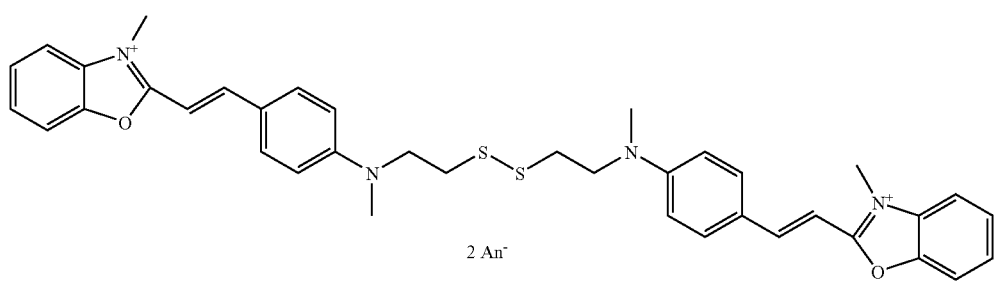
2 An⁻
4
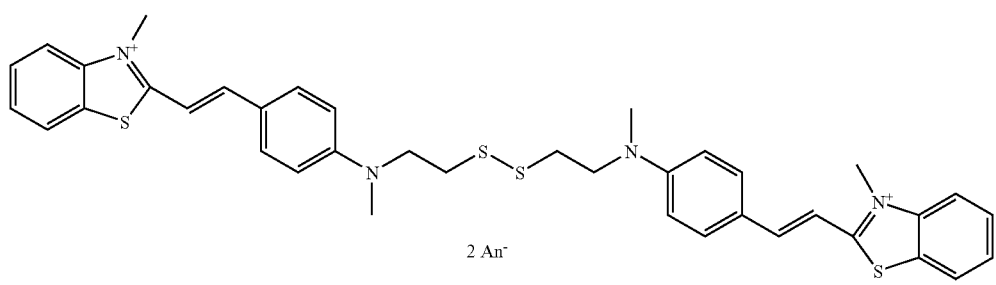
2 An⁻
5
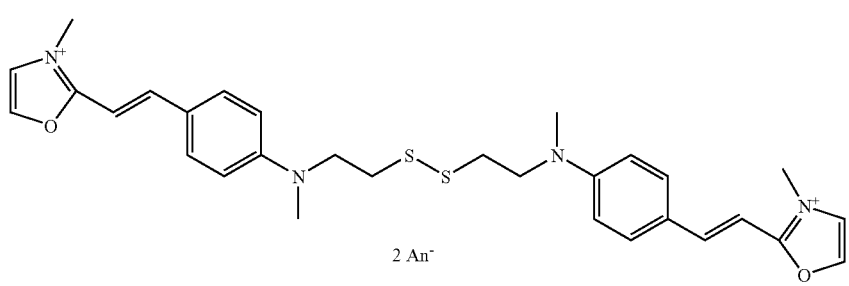
2 An⁻
6
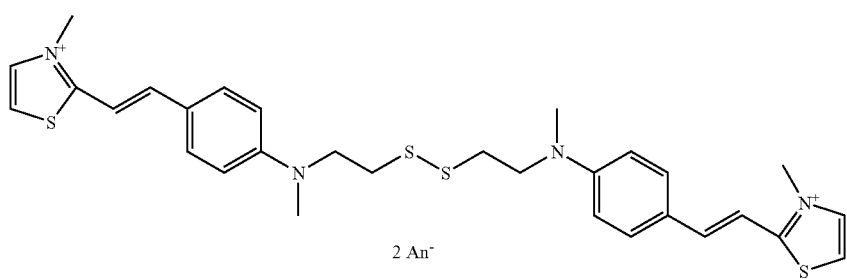
2 An⁻
7

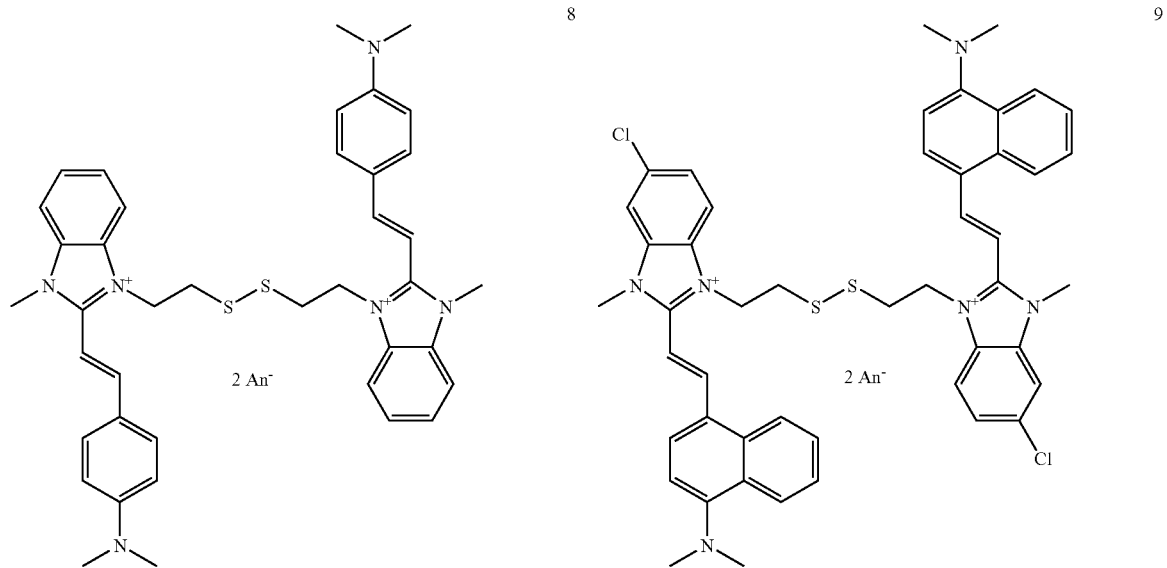
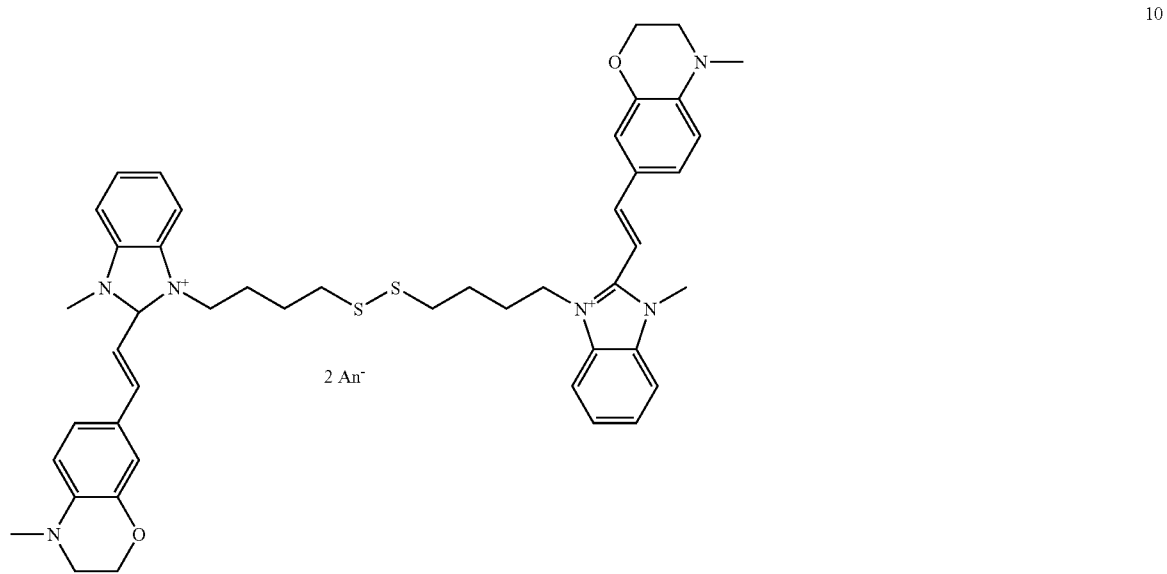

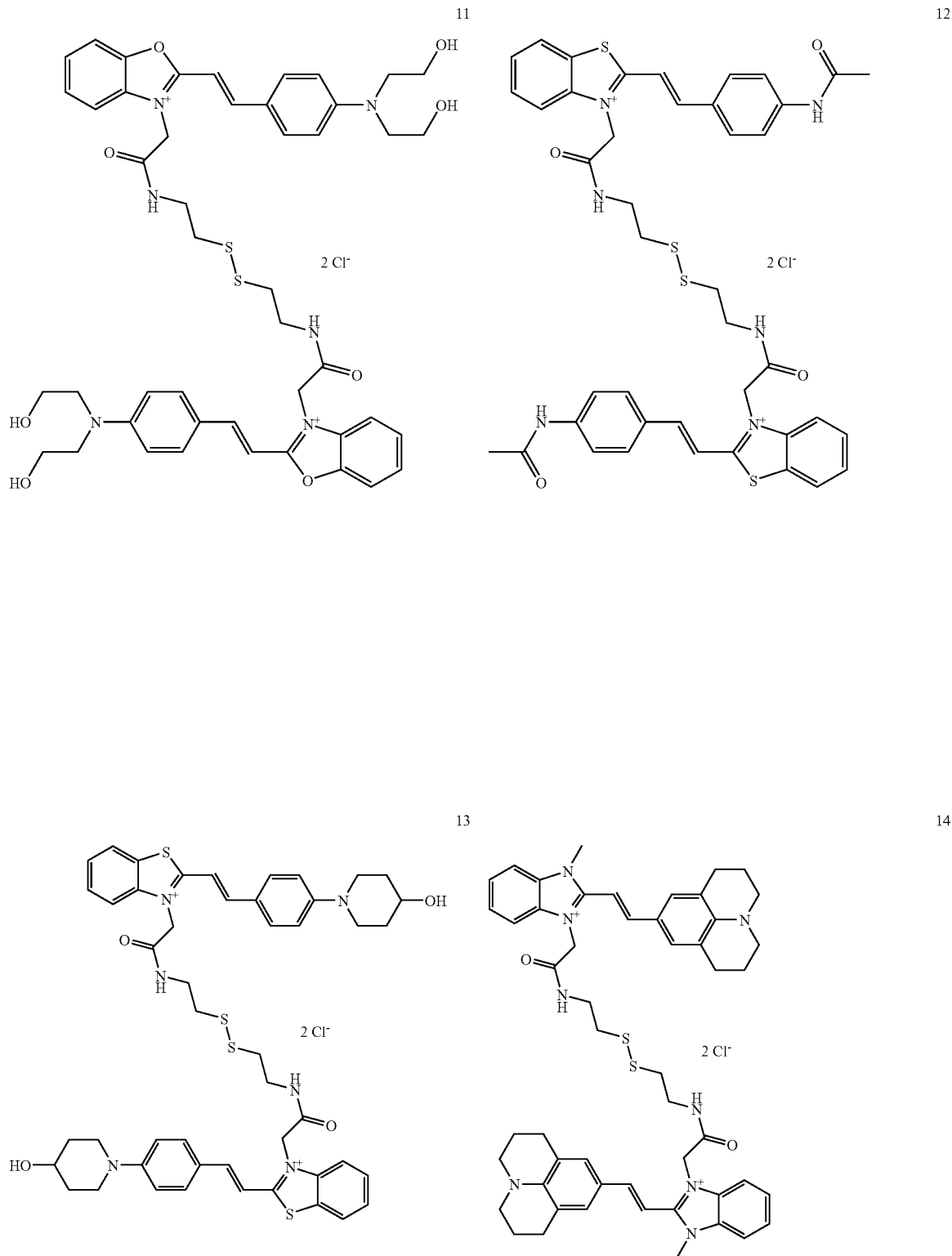

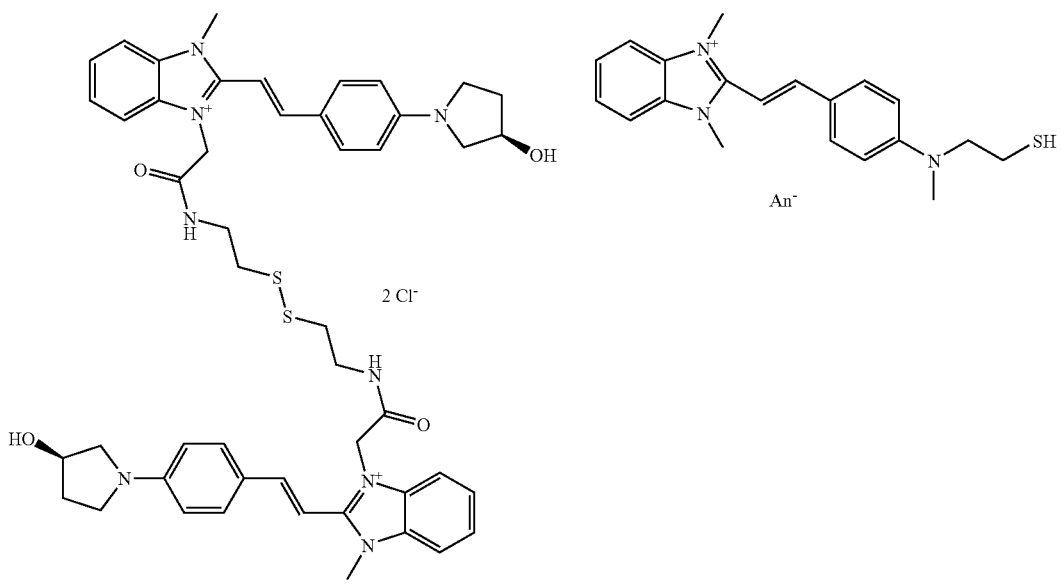
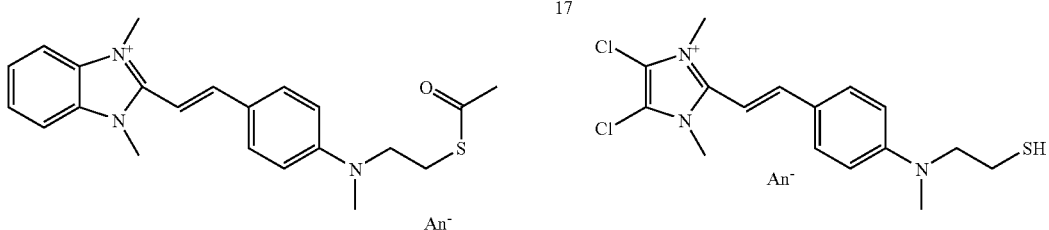
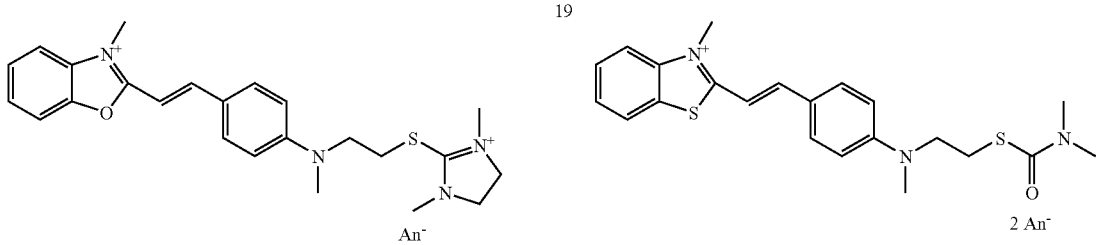
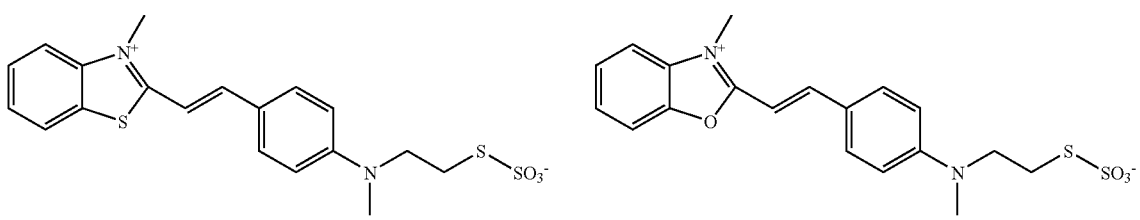

-continued
23
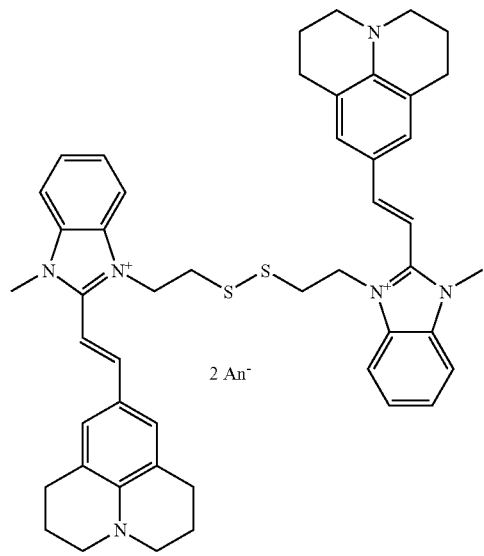
24
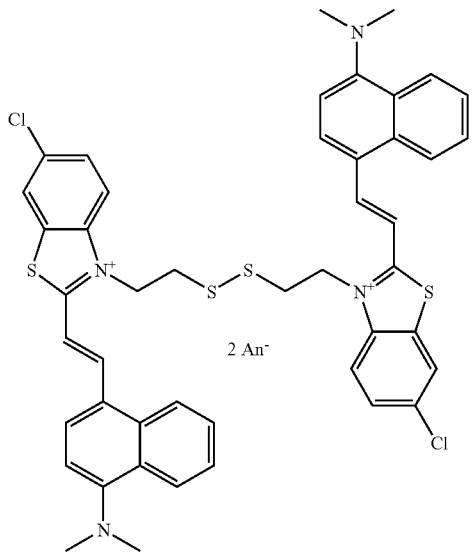
25
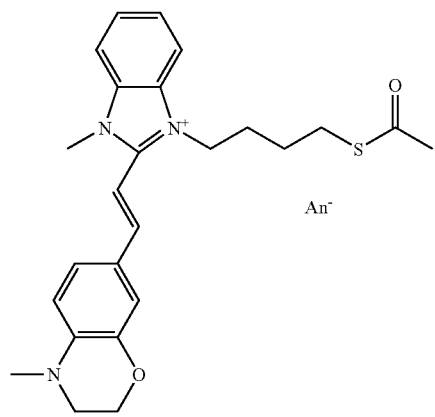
26
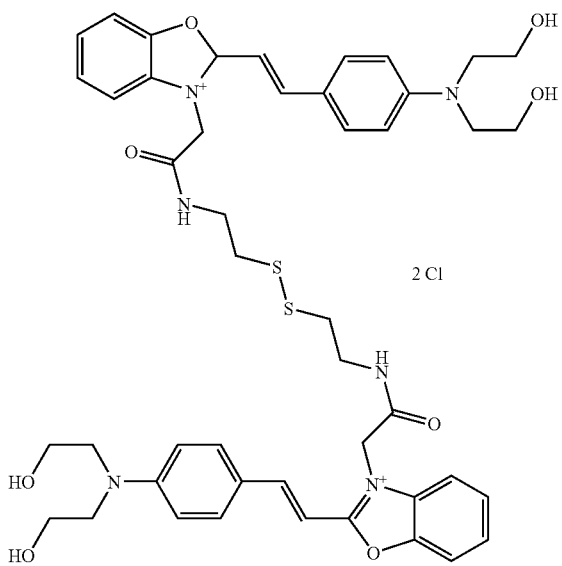
27
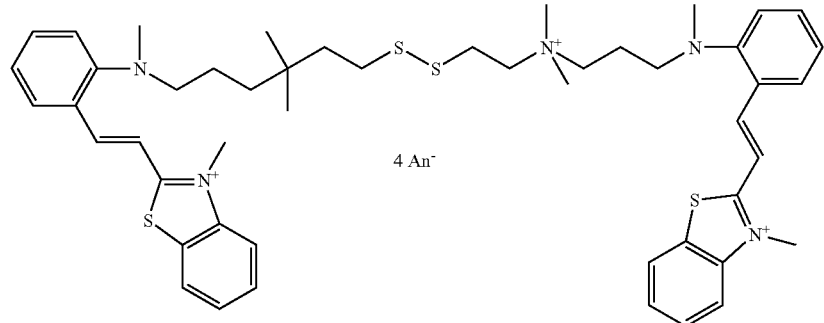

-continued
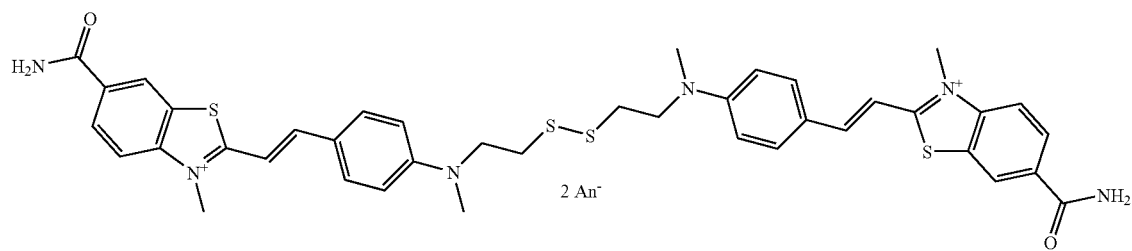
28
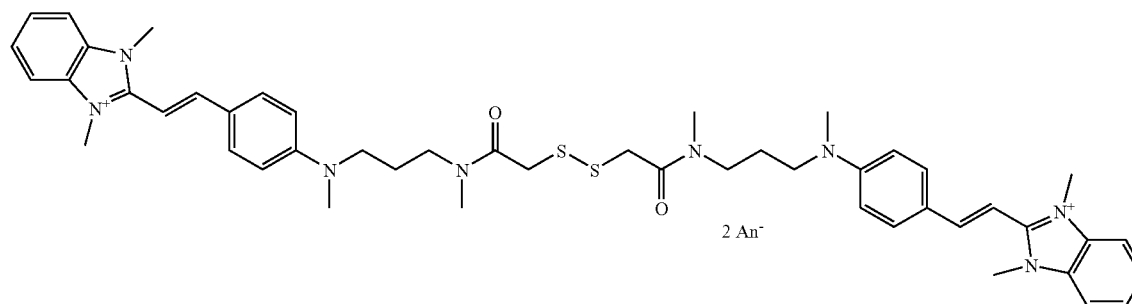
29
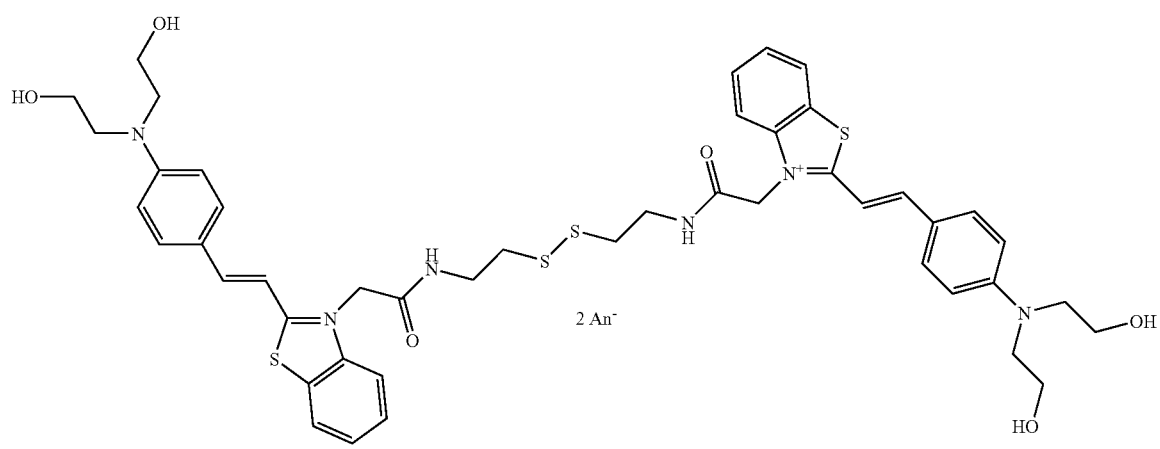
30
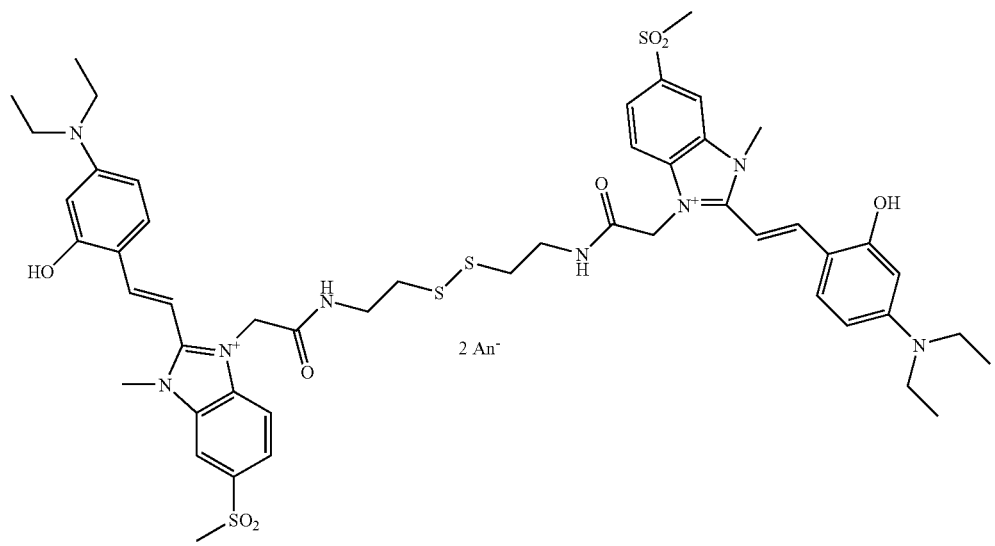
31

-continued
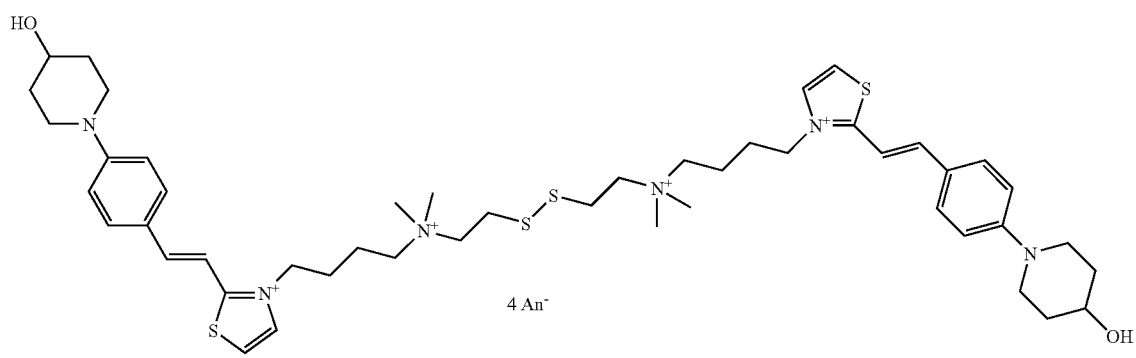
32
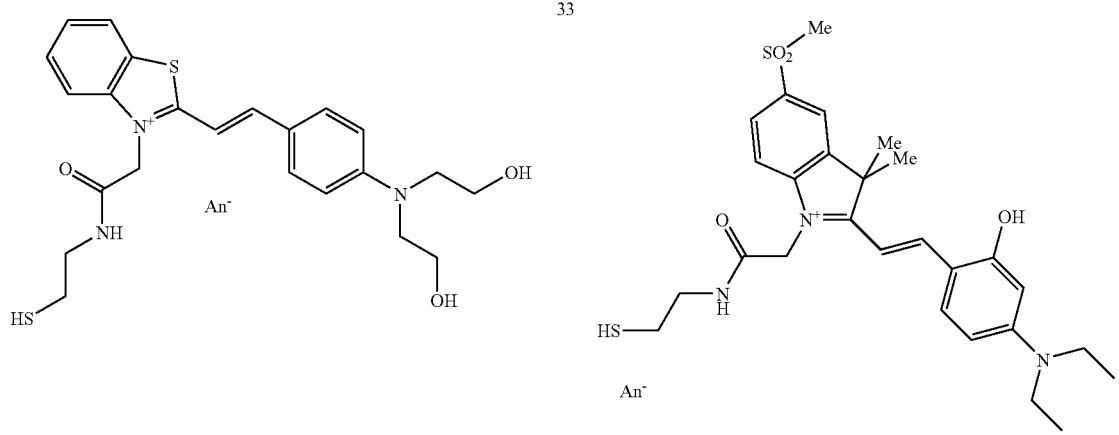
33
34
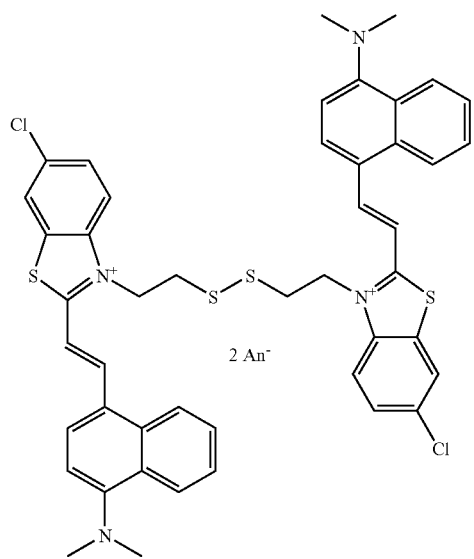
24

-continued
25
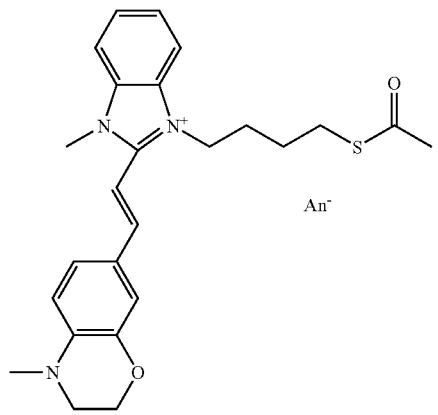
An⁻
26
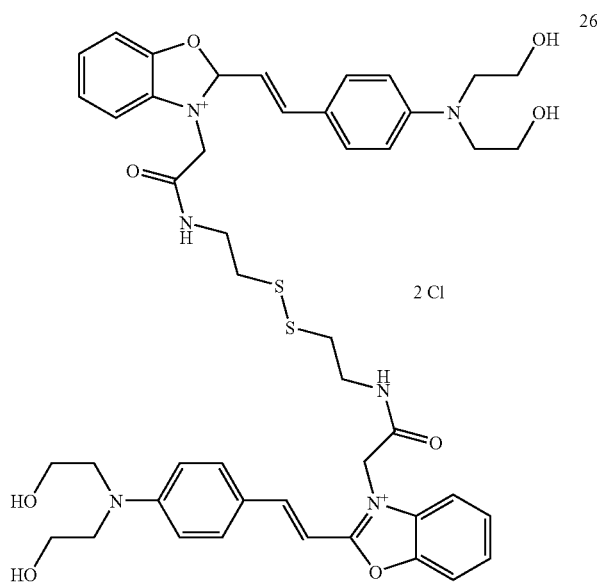
2 Cl⁻
41
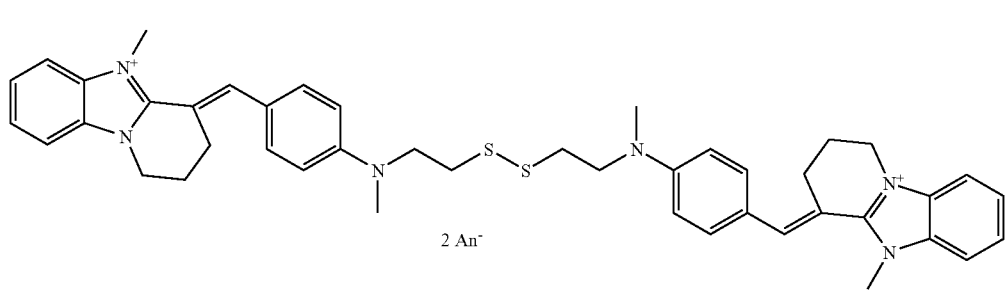
2 An⁻
42
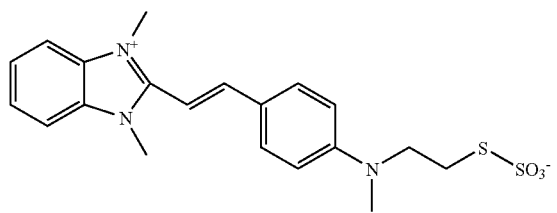

wherein An⁻, which may be identical or different, is an anionic counterion.

9. The dye composition according to claim 1, comprising, in a suitable cosmetic medium.

10. A process for dyeing keratin materials, comprising applying to keratin materials a dye composition in a cosmetically acceptable medium, wherein the dye comprises a fluorescent dye of formula (I) or (II):

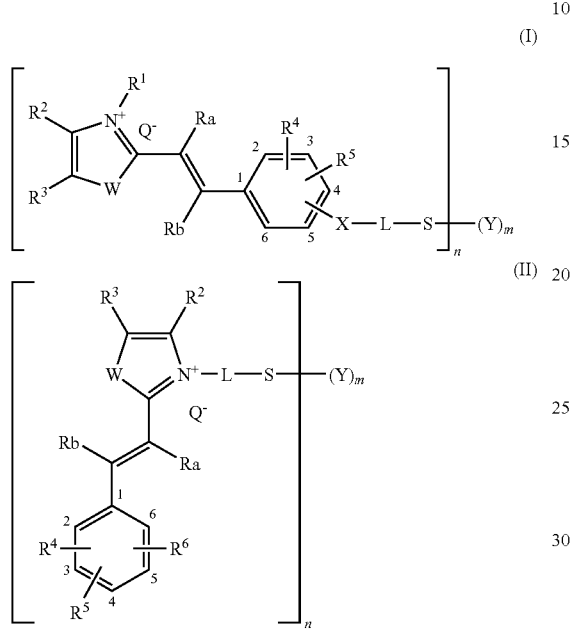

the organic or mineral acid salts thereof, optical isomers and geometric isomers thereof, and the solvates thereof: wherein in formulae (I) and (II):
n is an integer ranging from 1 to 2;
m is an integer ranging from 0 to 1;
Ra and Rb, which may be identical or different, are chosen from a hydrogen atom and a $C_1$-$C_4$ alkyl group;
$R^1$ is chosen from a hydrogen atom and a ($C_1$-$C_6$)alkyl group, optionally substituted with a group chosen from halogen, $C_1$-$C_4$ alkoxy, $C_1$-$C_4$ (di)(alkyl)amino, phenyl, tolyl, and methoxyphenyl;
or else $R^1$ and Ra together form a ($C_3$-$C_6$)alkylene chain or a ($C_3$-$C_7$)alkenylene;
$R^2$ and $R^3$, which may be identical or different, are chosen from a hydrogen atom and a halogen atom, an optionally substituted ($C_1$-$C_6$)alkyl group, a ($C_1$-$C_6$) alkoxy group, or a ($C_1$-$C_6$)alkylthio group; or else $R^2$ and $R^3$ form, together with the carbon atoms which bear them, an optionally substituted benzo ring;
$R^4$, $R^5$ and $R^6$, which may be identical or different, are chosen from:
a hydrogen atom;
a $C_1$-$C_6$ alkyl radical optionally substituted with at least one radical chosen from the radicals hydroxyl, $C_1$-$C_2$ alkoxy, $C_2$-$C_4$ (poly)hydroxyalkoxy, acylamino, and amino substituted with two $C_1$-$C_4$ alkyl radicals, which may be identical or different;
a halogen atom such as chlorine, fluorine or bromine;
a hydroxyl group;
a $C_1$-$C_2$ alkoxy radical;
a $C_1$-$C_2$ alkylthio radical;
an amino radical;
a 5- or 6-membered heterocycloalkyl radical which may be substituted with 1 to 3 groups, which may be identical or different, chosen from hydroxyl, amino, (di)alkylamino, and $C_1$-$C_4$ hydroxyalkyl;
an amino radical substituted with one or two $C_1$-$C_6$ alkyl radicals, which may be identical or different, optionally bearing at least:
i) a hydroxyl group,
ii) an amino group optionally substituted with one or two $C_1$-$C_3$ alkyl radicals, it being possible for said alkyl radicals to form, with the nitrogen atom to which they are attached, a saturated or unsaturated, optionally substituted heterocycle comprising from 5 to 7 members, optionally comprising at least one other heteroatom which may or may not be different from nitrogen,
—N(R)—C(O)—R' wherein the R radical is chosen from a hydrogen atom and a $C_1$-$C_4$ alkyl radical optionally bearing at least one hydroxyl group, and the R' radical is a $C_1$-$C_2$ alkyl radical;
a carboxylic radical in acid or salified form;
a polyhaloalkyl group comprising from 1 to 6 carbon atoms and from 1 to 6 halogen atoms, which may be identical or different;
or else two contiguous radicals $R^4$ with $R^5$ and/or $R^5$ with $R^6$ form, together with the carbon atoms which bear them, a benzo ring or a heterocycle, optionally substituted, fused to the phenyl group;
or else $R^4$, $R^5$ and $R^6$ form, together with the phenyl group of formula (II), a tricyclic unit of julolidine type:

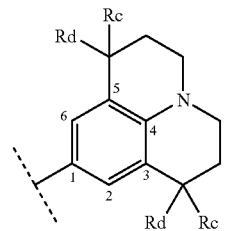

wherein Rc and Rd are chosen from a hydrogen atom and a $C_1$-$C_4$ alkyl group;
L is a $C_1$-$C_{20}$ divalent hydrocarbon-based chain, which is optionally substituted, optionally interrupted and/or optionally terminated at one or the other of its ends
i) with at least one divalent group or combinations thereof chosen from: —N(R)—; —N⁺(R)(R°)—, An⁻, —O—, —S—, —CO—, and —SO₂— with R and R°, which may be identical or different, chosen from a hydrogen, and a $C_1$-$C_4$ alkyl, hydroxyalkyl or aminoalkyl radical, and An⁻ is an anionic counterion, or ii) with a cationic heterocycle or cationic heteroaryl Het⁺, An⁻, wherein An⁻ is defined as above and Het⁺ is a saturated or unsaturated heterocycle comprising from 5 to 10 members, or a heteroaryl comprising from 5 to 10 members;
X is chosen from an oxygen atom, a sulfur atom and an NR group wherein R is chosen from a hydrogen atom and a ($C_1$-$C_6$)alkyl group;
Y is chosen from: i) a hydrogen atom; ii) an alkali metal; iii) an alkaline earth metal; iv) an ammonium group: $N^+R^\alpha R^\beta R^\gamma R^\delta$, An''⁻ or a phosphonium group:

$P^+R^\alpha R^\beta R^\gamma R^\delta$, $An'''^-$ with $R^\alpha$, $R^\beta$, $R^\gamma$ and $R^\delta$, which may be identical or different, chosen from a hydrogen atom and a $(C_1-C_4)$alkyl group and $An'''^-$ is an anionic counterion; or v) a thiol-function-protecting group;

W is chosen from an oxygen atom, sulfur atom, and an NR' group wherein R' is chosen from a hydrogen atom and a $(C_1-C_4)$alkyl group; and $Q^-$ is an anionic counterion;

it being understood that, when n is 2, then m is zero, and when n is 1, then m is 1.

11. The process for dyeing keratin materials according to claim 10, wherein the keratin materials are dark keratin fibers having a tone height of less than or equal to 6.

12. The process according to claim 10, wherein the dyeing composition further comprises a reducing agent wherein the reducing agent is applied before or after the application of the fluorescent dye of formula (I) or (II).

13. The process according to claim 10, wherein the composition comprises an oxidizing agent.

14. A multicompartment device wherein a first compartment contains a dye composition comprising a fluorescent dye of formula (I) or (II) as defined in claim 1, and a second compartment contains a reducing agent.

15. The dyeing process according to claim 13, wherein the keratin fibers are dark keratin fibers.

* * * * *

UNITED STATES PATENT AND TRADEMARK OFFICE
CERTIFICATE OF CORRECTION

PATENT NO. : 7,727,287 B2  Page 1 of 5
APPLICATION NO. : 12/233955
DATED : June 1, 2010
INVENTOR(S) : Andrew Greaves et al.

It is certified that error appears in the above-identified patent and that said Letters Patent is hereby corrected as shown below:

In claim 8, col. 91, formula 11,

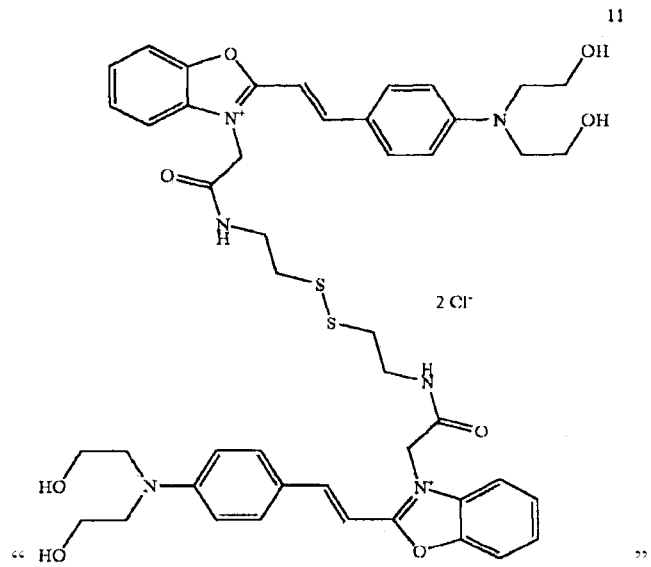

should read

Signed and Sealed this

Twenty-fourth Day of August, 2010

David J. Kappos
*Director of the United States Patent and Trademark Office*

CERTIFICATE OF CORRECTION (continued)
U.S. Pat. No. 7,727,287 B2

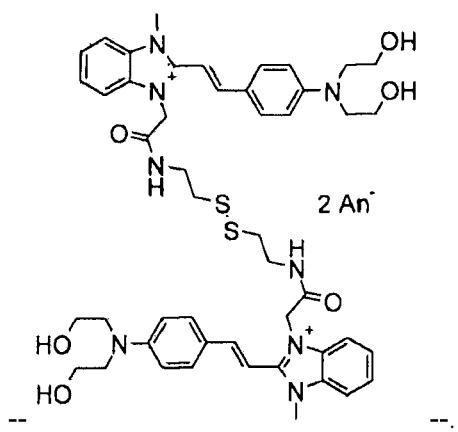

In claim 8, cols. 91, 92 and 93, in formulas 12, 13, 14, and 15, "2 Cl⁻" should read --2 An⁻--.

In claim 8, col. 96, in formula 26, "2 Cl⁻" should read --2 An⁻--.

In claim 8, cols. 95-96, formula 27,

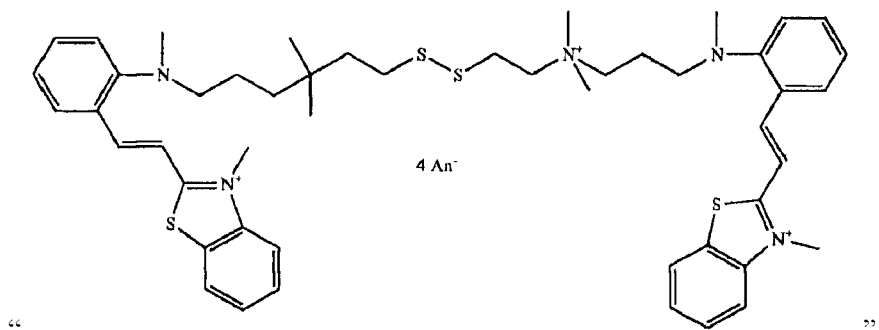

should read

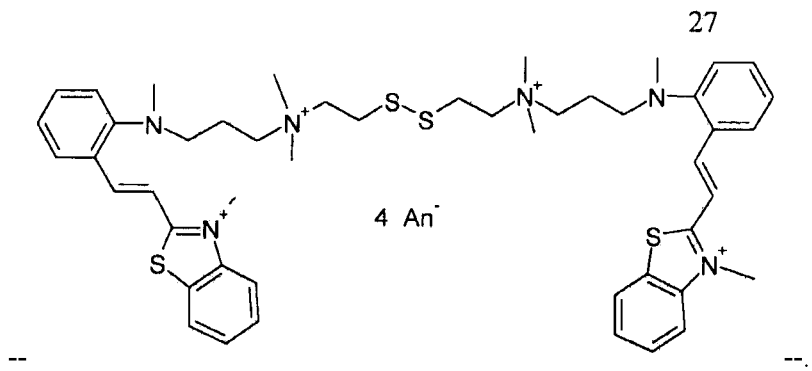

CERTIFICATE OF CORRECTION (continued)
U.S. Pat. No. 7,727,287 B2

Claim 8, cols. 99-102, in place of formulas 24, 25, and 26,

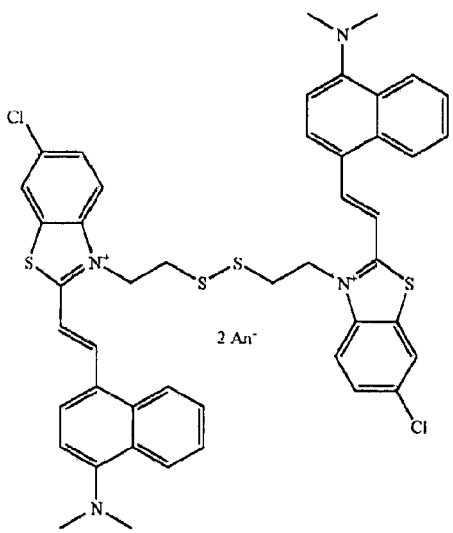

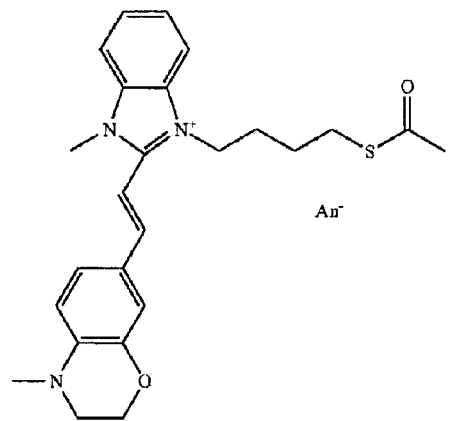

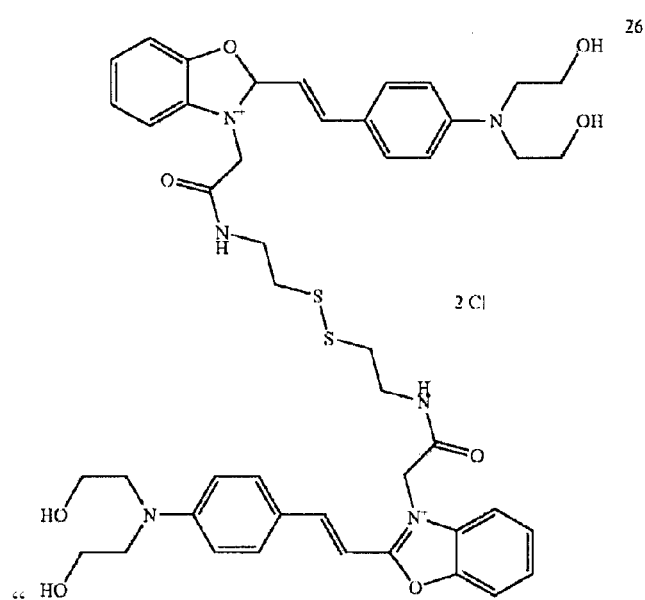

should read
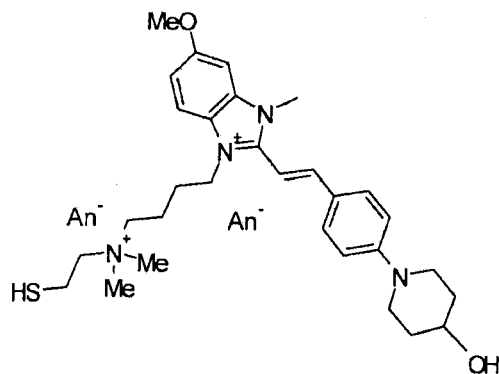
35
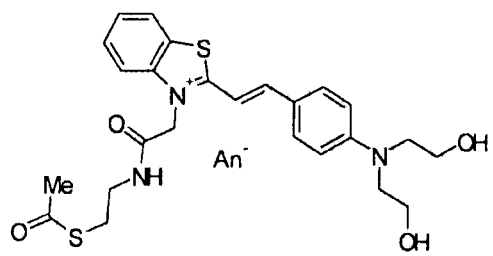
36
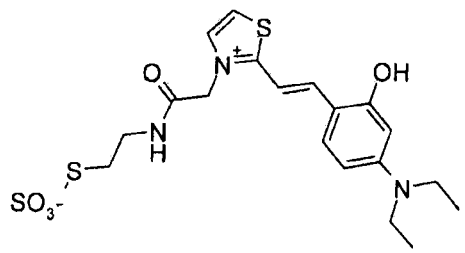
37
38

CERTIFICATE OF CORRECTION (continued)
U.S. Pat. No. 7,727,287 B2

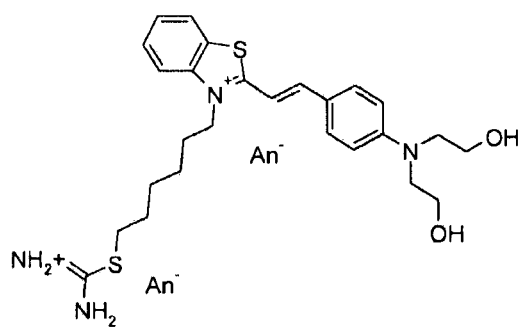

39

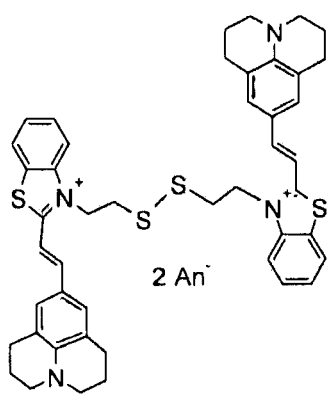

40